US010730932B2

(12) United States Patent
Pazgier et al.

(10) Patent No.: US 10,730,932 B2
(45) Date of Patent: Aug. 4, 2020

(54) STABLE IMMUNOGEN BASED ON INNER DOMAIN OF HIV-1 GP120 FOR INDUCING IMMUNITY AGAINST HIV

(71) Applicants: Marzena Pazgier, Mt. Airy, MD (US); George Lewis, Baltimore, MD (US); William Tolbert, Baltimore, MD (US); Neelakshi Gohain, Baltimore, MD (US)

(72) Inventors: Marzena Pazgier, Mt. Airy, MD (US); George Lewis, Baltimore, MD (US); William Tolbert, Baltimore, MD (US); Neelakshi Gohain, Baltimore, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 0 days.

(21) Appl. No.: 15/504,770

(22) PCT Filed: Aug. 19, 2015

(86) PCT No.: PCT/US2015/045940
§ 371 (c)(1),
(2) Date: Feb. 17, 2017

(87) PCT Pub. No.: WO2016/028917
PCT Pub. Date: Feb. 25, 2016

(65) Prior Publication Data
US 2017/0283486 A1  Oct. 5, 2017

Related U.S. Application Data

(60) Provisional application No. 62/039,625, filed on Aug. 20, 2014.

(51) Int. Cl.
C07K 16/10 (2006.01)
A61K 39/12 (2006.01)
A61K 39/21 (2006.01)
A61K 39/385 (2006.01)
C07K 14/005 (2006.01)
G01N 33/53 (2006.01)
A61K 39/00 (2006.01)

(52) U.S. Cl.
CPC .......... *C07K 16/1063* (2013.01); *A61K 39/12* (2013.01); *A61K 39/21* (2013.01); *A61K 39/385* (2013.01); *C07K 14/005* (2013.01); *G01N 33/53* (2013.01); *A61K 39/00* (2013.01); *A61K 2039/575* (2013.01); *C07K 2317/21* (2013.01); *C07K 2317/34* (2013.01); *C07K 2317/55* (2013.01); *C07K 2317/565* (2013.01); *C07K 2317/732* (2013.01); *C07K 2317/92* (2013.01); *C12N 2740/16034* (2013.01); *C12N 2740/16122* (2013.01); *C12N 2740/16134* (2013.01)

(58) Field of Classification Search
CPC .. C07K 16/1063; C07K 14/005; A61K 39/21; C12N 2740/16134; C12N 2740/16122
See application file for complete search history.

(56) References Cited

FOREIGN PATENT DOCUMENTS

WO  2013/006688  1/2013

OTHER PUBLICATIONS

Pantophlet, R., et al., Jan. 2003, Fine Mapping of the Interaction of Neutralizing and Nonneutralizing Monoclonal Antibodies with the CD4 Binding Site of Human Immunodeficiency Virus Type 1 gp120, J. Virol. 77(1):642-658.*
Yang, X., et al., 2003, Role of the gp120 Inner Domain Beta-Sandwich in the Interaction Between the Human Immunodeficiency Virus Envelope Glycoprotein Subunits, Virol. 313:117-125.*
Pietzsch, J., et al., Aug. 2010, Human Anti-HIV-Neutralizing Antibodies Frequently Target a Conserved Epitope Essential for Viral Fitness, J. Exp. Med. 207(9):1995-2002.*
Ding, S., et al., Oct. 2016, A Highly Conserved gp120 Inner Domain Residue Modulates Env Conformation and Trimer Stability, J. Virol. 90(19):8395-8409.*
Kassa et al., "Stabilizing Exposure of Conserved Epitopes by Structure Guided Insertion of Disulfide Bond in HIV-1 Envelope Glycoprotein", PLOS One, 8(10): e76139, pp. 1-13 (2013).
Kassa et al., "Transitions to and from the CD4-Bound Conformation Are Modulated by a Single-Residue Change in the Human Immunodeficiency Virus Type 1 gp120 Inner Domain", Journal of Virology 83(17): 8364-8378 (2009).
International Search Report and Written Opinion of the International Searching Authority, dated Feb. 1, 2016, in corresponding International application No. PCT/US15/45940.

(Continued)

Primary Examiner — Jeffrey S Parkin
(74) Attorney, Agent, or Firm — Wenderoth, Lind & Ponack, L.L.P.

(57) ABSTRACT

Stable immunogens comprising portions of the inner domain (ID) of the Human Immunodeficiency Virus (HIV-1) gp120 protein are provided. These ID immunogens selectively present the gp120 C1/C2 region in its CD4-bound state within a minimal structure. These ID immunogens can be used to vaccinate subjects against infection with HIV, the causative agent of Acquired Immunodeficiency Syndrome (AIDS). The immunogens can also be used as targets in screening to identify small molecule or peptide inhibitors that block HIV-1 viral entry and attachment steps, and as probes for identifying gp120 C1/C2 region-specific antibodies.

15 Claims, 32 Drawing Sheets
Specification includes a Sequence Listing.

(56) References Cited

OTHER PUBLICATIONS

Alam et al., "Antigenicity and Immunogenicity of RV144 vaccine AIDSVAX clade E envelope Immunogen is Enhanced by a gp120 N-Terminal Deletion", (2013), Journal of Virology 87(3):1554-1568.

Ampol et al. "Comprehensive Investigation of Common Antibody-Dependent Cell-Mediated Cytotoxicity Antibody Epitopes of HIV1 CRF01_AE gp120", (2012), AIDS Res Hum Retroviruses 28:1250-1258.

Desormeaux et al., "The Highly Conserved Layer3 Component of the HIV1 gp120 Inner Domain Is Critical for CD4-Required Conformational Transitions", (2013), Journal of Virology, 87(5):2549-2562.

Dey et al., "Structure-Based Stabilization of HIV-1 gp120 Enhances Humoral Immune Responses to the Induced Co-Receptor Binding Site", 2009, PLoS Pathog 5:e1000445.

Ferrari et al., "An HIV-1 gp120 Envelope Human Monoclonal Antibody That Recognizes a C1 Conformational Epitope Mediates Potent Antibody-Dependent Cellular Cytotoxicity (ADCC) Activity and Defines a Common ADCC Epitope in Human HIV-1 Serum", 2011, Journal of Virology. 85:7029-7036.

Finzi A, et al., "Topological Layers in the HIV1 Gp120 Inner Domain Regulate Gp41 Interaction and CD4-Triggered Conformational Transitions", (2010), Mol. Cell, 37(5):656-667.

Finzi et al., "Lineage-Specific Differences Between Human and Simian Immunodeficiency Virus Regulation of Gp120 Trimer Association and CD4 Binding", (2012), Journal of Virology, 86(17):8974-8986.

Guan et al., "Diverse Specificity and Effector Function Among Human Antibodies to HIV1 Envelope Glycoprotein Epitopes Exposed by CD4 Binding", Proc. Natl. Acad. Sci., (2013), U S A 110(1):E69-78.

Kwon et al., "Unliganded HIV-1 gp120 core structures assume the CD4-bound conformation with regulation by quaternary interactions and variable loops", 2012, Proc. Natl. Acad. Sci., U S A 109:5663-5668.

Lewis et al., "Epitope Target Structures of Fc-mediated Effector Function During HIV1 Acquisition" (2014), Curr. Opin. HIV AIDS, 9(3):263-270.

Pollara et al., "Epitope Specificity of Human Immunodeficiency Virus1 Antibody Dependent Cellular Cytotoxicity [ADCC] Responses", (2013), Curr. HIV Res., 11(5):378-387.

Veillette et al., "Interaction with Cellular CD4 Exposes HIV1 Envelope Epitopes Targeted by Antibody-Dependent Cell-Mediated Cytotoxicity", (2014), Journal of Virology, 88(5):2633-2644.

Veillette et al., "The HIV-1 Gp120 CD4-Bound Conformation Is Preferentially Targeted by Antibody-Dependent Cellular Cytotoxicity-Mediating Antibodies in Sera from HIV-1-Infected Individuals", 2015, Journal of Virology, 89:545-551.

\* cited by examiner

FIG. 1 – Alignment of ID immunogens retaining V1V2 region (clades)

```
A1_V1V2           VPVWKDAETTLFCASDAKAYETECHNVWATHACVPTDPNPQEIHLENVTE
A2_V1V2           VPVWKDADTTLFCASDAKAYDTECHNVWATHACVPTDPNPQEVNLENVTE
B_V1V2            VPVWKEATTTLFCASDAKAYDTECHNVWATHACVPTDPNPQEVVLENVTE
C_V1V2            VPVWKEAKTTLFCASDAKAYEKECHNVWATHACVPTDPNPQEIVLENVTE
D_V1V2            VPVWKEATTTLFCASDAKSYKTECHNIWATHACVPTDPNPQEIELENVTE
F1_V1V2           VPVWKEATTTLFCASDAKSYEKECHNVWATHACVPTDPNPQEVVLENVTE
F2_V1V2           VPVWKEATTTLFCASDAKAYERECHNVWATYACVPTDPSPQELVLGNVTE
G_V1V2            VPVWEDADTTLFCASDAKAYSTECHNVWATHACVPTDPNPQEITLENVTE
H_V1V2            VPVWKEAKTTLFCASDAKAYETECHNVWATHACVPTDPNPQEMVLENVTE
01_AE_V1V2        VPVWRDADTTLFCASDAKAHETECHNVWATHACVPTDPNPQEIHLENVTE
02_AG_V1V2        VPVWRDAETTLFCASDAKAYDTECHNVWATHACVPTDPNPQEIHLENVTE
03_AB_V1V2        VPVWKEATTTLFCASDAKAYSKECHNVWATYACVPTDPSPQEIPLENVTE
04_CPX_V1V2       VPVWRDAETTPFCASDAKAYDKECHNIWATHACVPTDPNPQEIALKNVTE
06_CPX_V1V2       VPAWEDADTILFCASDAKAYSAECHNVWATHACVPTDPNPQEIALENVTE
08_BC_V1V2        VPVWKEAKTTLFCASDAKAYETECHNVWATHACVPTDPNPQEIVMENVTE
10_CD_V1V2        VPVWKETTTTLFCASDAKAYKAECHNIWATHACVPTDPNPQEIVLENVTE
11_CPX_V1V2       VPVWKDADTTLFCASDAKAYSTECHNVWATHACVPTDPNPQEIPLENVTE
12_BF_V1V2        VPVWKEATTTLFCASDAKSYERECHNVWATHACVPTDPNPQEVDLENVTE
14_BG_V1V2        VPVWKEATTTLFCASDAKAYDAECHNVWATHACVPTDPNPQEVALENVTE
CON_OF_CONS_V1V2  VPVWKEANTTLFCASDAKAYDTECHNVWATHACVPTDPNPQEIVLENVTE
                  **.*.::  *    *******::. ****:***:*******.***: : ****

A1_V1V2           EFNMWKNNMVEQMHTDIISLWDQCLKPCVKLTPLCVTLNCSNVNVTN--N
A2_V1V2           DFNMWKNNMVEQMHEDIISLWDQCLKPCVKLTPLCVTLNCSNANTTN--N
B_V1V2            NFNMWKNNMVEQMHEDIISLWDQCLKPCVKLTPLCVTLNCTDLMNAT-NT
C_V1V2            NFNMWKNDMVDQMHEDIISLWDQCLKPCVKLTPLCVTLNCTNAT----NA
D_V1V2            NFNMWKNNMVEQMHEDIISLWDQCLKPCVKLTPLCVTLNCTDVKRNN--T
F1_V1V2           NFDMWKNNMVEQMHTDIISLWDQCLKPCVKLTPLCVTLNCTDVNATN--N
F2_V1V2           NFNMWKNNMVDQMHEDIISLWDQCLKPCVKLTPLCVTLNCTDVNVTI--N
G_V1V2            NFNMWKNNMVEQMHEDIISLWDECLKPCVKLTPLCVTLNCTDVNVTN--N
H_V1V2            NFNMWENDMVEQMHTDIISLWDQCLKPCVKLTPLCVTLDCSNVNTTN--A
01_AE_V1V2        NFNMWKNNMVEQMQEDVISLWDQCLKPCVKLTPLCVTLNCTNANLTNVNN
02_AG_V1V2        NFNMWKNNMVEQMHEDIISLWDQCLKPCVKLTPLCVTLDCHNNITNS--N
03_AB_V1V2        NFNMGKNNMVEQMHEDIISLWDQCLKPCVKLTPLCVTLNCTDLKKNV--T
04_CPX_V1V2       NFNMWKNNMVEQMHEDIISLWDECLKPCVKLTPLCVALNCSNATINN--S
06_CPX_V1V2       NFNMWKNHMVEQMHEDIISLWDECLKPCVKLTPLCVTLNCTNVTKNN--N
08_BC_V1V2        NFNMWNNDMVNQMHEDVISLWDQCLKPCVKLTPLCVTLECTNVSSNG-NG
10_CD_V1V2        NFNMWKNGMVDQMHEDIISLWDQCLKPCVKLTPLCVTLNCSDVNATN--S
11_CPX_V1V2       NFNMWKNNMVEQMHEDIISLWDECLKPCVKLTPLCVTLNCTDVKNAT--N
12_BF_V1V2        NFDMWKNNMVEQMHTDIISLWDQCLKPCVKLTPLCVTLNCTDANATA--N
14_BG_V1V2        NFNMWENNMVDQMQEDIISLWDQCLKPCVELTPLCVTLNCTDFNNTT-NN
CON_OF_CONS_V1V2  NFNMWKNNMVEQMHEDIISLWDQCLKPCVKLTPLCVTLNCTDVNATN--N
                  :*:* :* **:**: *:*****:******:******:*:* :
```

FIG. 1 (continued)

```
A1_V1V2             TTN------THEEEIKNCSFNMTTELRDKKQKVYSLFYRLDVVQINEN--
A2_V1V2             ST---------MEEIKNCSYNITTELRDKTQKVYSLFYKLDVVQLDES--
B_V1V2              NTTII---YRWRGEIKNCSFNITTSIRDKVQKEYALFYKLDVVPIDND--
C_V1V2              T-NT-------MGEIKNCSFNITTELRDKKQKVYALFYRLDIVPLNEN--
D_V1V2              SNDT------NEGEMKNCSFNITTEIRDKKKQVHALFYKLDVVPIDDN--
F1_V1V2             DTNDN-----KTGAIQNCSFNMTTEVRDKKLKVHALFYKLDIVPISNN--
F2_V1V2             TT---N---VTLGEIKNCSFNITTEIKDKKKKEYALFYRLDVVPINN---
G_V1V2              NT---N---NTKKEIKNCSFNITTEIRDKKKKEYALFYRLDVVPINDN--
H_V1V2              T-NSRF---NMQEELTNCSFNVTTVIRDKQQKVHALFYRLDVVPIDDN--
01_AE_V1V2          ITNVSNIIGNITNEVRNCSFNMTTELRDKKQKVHALFYKLDIVQIEDN--
02_AG_V1V2          TTN------NNAGEIKNCSFNMTTELRDKKQKVYALFYRLDVVQINKN--
03_AB_V1V2          STNTSS---IKMMEMKNCSFNITTDLRDKVKKEYALFYKLDVVQIDN---
04_CPX_V1V2         TK---T---NSTEEIKNCSFNITTEIRDKKKKEYALFYRLDIVPINDSAN
06_CPX_V1V2         TK---I---MGREEIKNCSFNVTTEIRDKKKKEYALFYRLDVVPIDDN--
08_BC_V1V2          TYNETY--NESVKEIKNCSFNATTLLRDRKKTVYALFYRLDIVPLNDE--
10_CD_V1V2          ATNT------VVAGMKNCSFNITTEIRDKKKQEYALFYKLDVVQIDGS--
11_CPX_V1V2         TT-------VEAAEIKNCSFNITTEIKDKKKKEYALFYKLDVVPINDN--
12_BF_V1V2          ATKEHP--EGRAGAIQNCSFNMTTEVRDKQMKVQALFYRLDIVPISDN--
14_BG_V1V2          TTNTR---NDGEGEIKNCSFNITTSLRDKIKKEYALFYNLDVVQMDND--
CON_OF_CONS_V1V2    TTN--------NEEIKNCSFNITTEIRDKKKKVYALFYKLDVVPIDDN--
                      : ***:* ** ::*:     :***.**:* :.

A1_V1V2             NS----NSSYRLINCNTSAITQACPKVSFEPIPIHYCAPAGFAILKCKDK
A2_V1V2             NK--S-EYYYRLINCNTSAITQACPKVSFEPIPIHYCAPAGFAILKCKDP
B_V1V2              N------TSYRLISCNTSVITQACPKVSFEPIPIHYCAPAGFAILKCNDK
C_V1V2              N-------SYRLINCNTSAITQACPKVSFDPIPIHYCAPAGYAILKCNNK
D_V1V2              NS----NTSYRLINCNTSAITQACPKVTFEPIPIHYCAPAGFAILKCKDK
F1_V1V2             NS------KYRLINCNTSTITQACPKVSWDPIPIHYCAPAGYAILKCNDK
F2_V1V2             ------SIVYRLISCNTSTVTQACPKVSFEPIPIHYCAPAGFAILKCNDK
G_V1V2              GN----SSIYRLINCNVSTIKQACPKVTFDPIPIHYCAPAGFAILKCRDK
H_V1V2              NS-----YQYRLINCNTSVITQACPKVSFEPIPIHYCAPAGFAILKCNNK
01_AE_V1V2          N-------SYRLINCNTSVIKQACPKISFDPIPIHYCTPAGYAILKCNDK
02_AG_V1V2          N------SQYRLINCNTSAITQACPKVSFEPIPIHYCAPAGFAILKCNDK
03_AB_V1V2          -------DSYRLISCNTSVVTQACPKISFEPIPIHYCAPAGFAILKCNDK
04_CPX_V1V2         NN--SINSEYMLINCNASTIKQACPKVTFEPIPIHYCAPAGFAILKCNDK
06_CPX_V1V2         N------NSYRLINCNASTIKQACPKVSFEPIPIHYCAPAGFAILKCRDK
08_BC_V1V2          NSGKNSSEYYRLINCNTSAITQACPKVTFDPIPIHYCTPAGYAILKCNDK
10_CD_V1V2          N------TSYRLINCNTSAITQACPKVTFEPIPIHYCAPAGFAILKCNDK
11_CPX_V1V2         N-----NSIYRLINCNVSTVKQACPKVTFEPIPIHYCAPAGFAILKCNDK
12_BF_V1V2          NS-----NEYRLINCNTSTITQACPKVSWDPIPIHYCAPAGYAILKCNDK
14_BG_V1V2          N------SSYRLTSCNTSIITQACPKVSFTPIPIHYCAPAGFVILKCNNK
CON_OF_CONS_V1V2    N-------SYRLINCNTSAITQACPKVSFEPIPIHYCAPAGFAILKCNDK
                     * *  .**.* :.*****:::  ******:***:.****.:
```

FIG. 1 (continued)

```
A1_V1V2             EFNGTGPCKNVSTVQCTHGIKPVVSTGGGDMRDNWRSELYKYKVVKIEPL
A2_V1V2             RFNGTGSCNNVSSVQCTHGIKPVASTGGGDMRDNWRSELYKYKVVKIEPL
B_V1V2              KFNGTGPCTNVSTVQCTHGIRPVVSTGGGDMRDNWRSELYKYKVVKIEPL
C_V1V2              TFNGTGPCNNVSTVQCTHGIKPVVSTGGGDMRDNWRSELYKYKVVEIKPL
D_V1V2              KFNGTGPCKNVSTVQCTHGIRPVVSTGGGDMRDNWRSELYKYKVVKIEPL
F1_V1V2             RFNGTGPCKNVSTVQCTHGIKPVVSTGGGNMKDNWRSELYKYKVVEIEPL
F2_V1V2             KFNGTGLCRNVSTVQCTHGIRPVVSTGGGDMRDNWRSELYKYKVVKIEPL
G_V1V2              KFNGTGPCKNVSTVQCTHGIKPVVSTGGGDMRDNWRSELYKYKIVKIKPL
H_V1V2              TFNGTGPCTNVSTVQCTHGIRPVVSTGGGDMRDNWRSELYKYKVVKIEPL
01_AE_V1V2          NFNGTGPCKNVSSVQCTHGIKPVVSTGGGNIKDNWRSELYKYKVVQIEPL
02_AG_V1V2          EFNGTGPCKNVSTVQCTHGIKPVVSTGGGDMRDNWRSELYKYKVVKIEPL
03_AB_V1V2          KFNGTGPCTNVSTVQCTHGIKPVVSTGGGDMRDNWRSELYKYKVVKIEPL
04_CPX_V1V2         NFTGLGPCTNVSSVQCTHGIKPVVSTGGGDMRDNWRSELYKYKVVKIEPV
06_CPX_V1V2         NFNGTGPCKNVSTVQCTHGIKPVVSTGGGDMRDNWRSELYKYKVVKIKPL
08_BC_V1V2          KFNGTGQCHNVSTVQCTHGIKPVVSTGGGDMRNNWRNELYKYKVVEIKPL
10_CD_V1V2          KFNGTGPCKNVSTVQCTHGIKPVVSTGGGDMRDNWRSELYKYKVVKIEPL
11_CPX_V1V2         KFNGTGPCKNVSTVQCTHGIKPVVSTTGGDMRDNWRSELYKYKVVEIKPL
12_BF_V1V2          KFNGTGPCKNVSTVQCTHGIKPVVSTGGGNMKDNWRSELYKYKVVEIEPL
14_BG_V1V2          TFNGTGPCTNVSTVQCTHGIRPVVSTGGGNMKDNWRSELYKYKVVKIEPL
CON_OF_CONS_V1V2    KFNGTGPCKNVSTVQCTHGIKPVVSTGGGDMRDNWRSELYKYKVVKIEPL
                     *.*  *  *  ***:*******:**.**  **:::***.*******:*:*:

A1_V1V2             GVAPTRAKRRVVEREKR
A2_V1V2             GVAPTRAKRRVVEREKR
B_V1V2              GVAPTKAKRRVVQREKR
C_V1V2              GIAPTKAKRRVVEREKR
D_V1V2              GVAPTRAKRRVVEREKR
F1_V1V2             GVAPTKAKRQVVKRERR
F2_V1V2             GVAPTKAKRQVVQREKR
G_V1V2              GVAPTRARRRVVEREKR
H_V1V2              GVAPTEARRRVVEREKR
01_AE_V1V2          GIAPTRAKRRVVEREKR
02_AG_V1V2          GVAPTRAKRRVVEREKR
03_AB_V1V2          GVAPTKAKRRVVQREKR
04_CPX_V1V2         GVAPTRARRRVVQREKR
06_CPX_V1V2         GIAPTRARRRVVGREKR
08_BC_V1V2          GVAPTAAKRRVVEREKR
10_CD_V1V2          GLAPTKAKRRVVEREKR
11_CPX_V1V2         GVAPTRAKRRVVEREKR
12_BF_V1V2          GVAPTRAKRQVVKREKR
14_BG_V1V2          GVAPTRAKRRVVQREKR
CON_OF_CONS_V1V2    GVAPTKAKRRVVEREKR
                    *:***  *:*:** **:*
```

FIG. 2 – Alignment of ID immunogens retaining V1V2 region (strains)

```
AB097872_V1V2    VPVWRDAETTLFCASDAKAHVGECHNVWATHACVPTDPNPQEIHLENVTE
AB052867_V1V2    VPVWKDAETTLFCASDAKAYDAECHNVWATHACVPTDPNPQEISLENVTE
yu2gp120_V1V2    VPVWKEATTTLFCASDAKAYDTECHNVWATHACVPTDPNPQEVKLENVTE
HXB2_V1V2        VPVWKEATTTLFCASDAKAYDTECHNVWATHACVPTDPNPQEVVLVNVTE
HM623558_V1V2    VPVWKEAKTTLFCASDAKAYERECHNVWATHACVPTDPNPQEIALENVTE
DQ404010_V1V2    VPVWKEAKTTLFCASDAKAYEKECHNVWATHACVPTDPNPQEMVLENVTE
                 ****::.* **********:  ********************:.* ****

AB097872_V1V2    NFNMWKNKMADQMQEDVISLWDQCLKPCVKLTPLCVTLNCTDAQVNQTWN
AB052867_V1V2    DFNMWKNKMVEQMHVDIISLWDQCLKPCVKLTPLCVTLDCHDNITTSG--
yu2gp120_V1V2    NFNMWKNNMVEQMHEDIISLWDQCLKPCVKLTPLCVTLNCTDLRN-ATNT
HXB2_V1V2        NFNMWKNDMVEQMHEDIISLWDQCLKPCVKLTPLCVSLKCTDLKN-DTNT
HM623558_V1V2    NFNMWKNNMVDQMHEDIISLWDQCLKPCVKLTPLCVTLNCTNVTKNDTNA
DQ404010_V1V2    NFNMWKNDMVNQMHEDVISLWDQCLKPCVKLTPLCVTLECGNVTQNGTY-
                 :******.*.:**: *:*******************:*.*  :

AB097872_V1V2    NVTKADNITNLENITNEVKNCSFNMTTEIRDKQQRVQALFYKLDIVPIGN
AB052867_V1V2    ------NRNISVEMKGEIKNCSFNMTTVLRDKKEKVTALFYRLDVVQINN
yu2gp120_V1V2    TSSSW-----ETMEKGEIKNCSFNITTSIRDKVQKEYALFYNLDVVPIDN
HXB2_V1V2        NSSSG----RMIMEKGEIKNCSFNISTSIRGKVQKEYAFFYKLDIIPIDN
HM623558_V1V2    NNT--------AEGKEERKNCSFNATTELRDKNRKVYALFYKLDIVPLNP
DQ404010_V1V2    N---------DESNKEITNCTFNTTTEIRGRKQKVYALFYKLDIVPISE
                       .  *  .**:** :*  :*.:  .:    *:**.**:: :.

AB097872_V1V2    NN-NKTSGEYRLINCNTSVIKQACPKVSFDPIPIHYCTPAGFAILKCNDK
AB052867_V1V2    NS-S-NSSLYRLINCNTSTTTQACPKVTFEPIPIHYCAPAGFAILKCNDK
yu2gp120_V1V2    -----A--SYRLISCNTSVITQACPKVSFEPIPIHYCAPAGFAILKCNDK
HXB2_V1V2        -----DTTSYKLTSCNTSVITQACPKVSFEPIPIHYCAPAGFAILKCNNK
HM623558_V1V2    SNNSNSSGQYRLITCNTSVITQACPKIIFDPIPIHYCAPAGYAILKCNNK
DQ404010_V1V2    -----TSNQSRLISCNTSVITQACPKVSFDPIPIHYCTPAGYAILKCNDK
                 :*  .****. .*****: *:*******:***:***:*

AB097872_V1V2    KFNGTGPCKNVSSVQCTHGIKPVVSTGGGNIKDNWRSELYKYKVVEIEPL
AB052867_V1V2    KFNGTGPCKNVSSVQCTHGIRPVVSTGGGDMRDNWRSELYKYKVVKLEPL
yu2gp120_V1V2    KFNGTGPCTNVSTVQCTHGIRPVVSTGGGDMRDNWRSELYKYKVVKIEPL
HXB2_V1V2        TFNGTGPCTNVSTVQCTHGIRPVVSTGGGDMRDNWRSELYKYKVVKIEPL
HM623558_V1V2    TFNGTGPCNNVSTVQCTHGIKPVVSTGGGDMRDNWRSELYKYKVVQIEPL
DQ404010_V1V2    TFNGTGPCRNVSTVQCTHGIKPVVSTGGGDMRDNWRSELYKYKVVEIKPL
                 .****** ***:*******:*******:::**************:::**

AB097872_V1V2    GIAPTRAKRRVVERQKR
AB052867_V1V2    GVAPTRARRRVVTREKR
yu2gp120_V1V2    GVAPTKAKRRVVQREKR
HXB2_V1V2        GVAPTKAKRRVVQREKR
HM623558_V1V2    GVAPTKAKRRVVQREKR
DQ404010_V1V2    GVAPTTAKRRVVEREKR
                 *:*** *:****  *:**
```

FIG. 3 – Alignment of ID immunogens retaining V1V2 region (clades and strains)

```
A1_V1V2              VPVWKDAETTLFCASDAKAYETECHNVWATHACVPTDPNPQEIHLENVTE
A2_V1V2              VPVWKDADTTLFCASDAKAYDTECHNVWATHACVPTDPNPQEVNLENVTE
B_V1V2               VPVWKEATTTLFCASDAKAYDTECHNVWATHACVPTDPNPQEVVLENVTE
C_V1V2               VPVWKEAKTTLFCASDAKAYEKECHNVWATHACVPTDPNPQEIVLENVTE
D_V1V2               VPVWKEATTTLFCASDAKSYKTECHNIWATHACVPTDPNPQEIELENVTE
F1_V1V2              VPVWKEATTTLFCASDAKSYEKECHNVWATHACVPTDPNPQEVVLENVTE
F2_V1V2              VPVWKEATTTLFCASDAKAYERECHNVWATYACVPTDPSPQELVLGNVTE
G_V1V2               VPVWEDADTTLFCASDAKAYSTECHNVWATHACVPTDPNPQEITLENVTE
H_V1V2               VPVWKEAKTTLFCASDAKAYETECHNVWATHACVPTDPNPQEMVLENVTE
01_AE_V1V2           VPVWRDADTTLFCASDAKAHETECHNVWATHACVPTDPNPQEIHLENVTE
02_AG_V1V2           VPVWRDAETTLFCASDAKAYDTECHNVWATHACVPTDPNPQEIHLENVTE
03_AB_V1V2           VPVWKEATTTLFCASDAKAYSKECHNVWATYACVPTDPSPQEIPLENVTE
04_CPX_V1V2          VPVWRDAETTPFCASDAKAYDKECHNIWATHACVPTDPNPQEIALKNVTE
06_CPX_V1V2          VPAWEDADTILFCASDAKAYSAECHNVWATHACVPTDPNPQEIALENVTE
08_BC_V1V2           VPVWKEAKTTLFCASDAKAYETECHNVWATHACVPTDPNPQEIVMENVTE
10_CD_V1V2           VPVWKETTTTLFCASDAKAYKAECHNIWATHACVPTDPNPQEIVLENVTE
11_CPX_V1V2          VPVWKDADTTLFCASDAKAYSTECHNVWATHACVPTDPNPQEIPLENVTE
12_BF_V1V2           VPVWKEATTTLFCASDAKSYERECHNVWATHACVPTDPNPQEVDLENVTE
14_BG_V1V2           VPVWKEATTTLFCASDAKAYDAECHNVWATHACVPTDPNPQEVALENVTE
CON_OF_CONS_V1V2     VPVWKEANTTLFCASDAKAYDTECHNVWATHACVPTDPNPQEIVLENVTE
AB097872_V1V2        VPVWRDAETTLFCASDAKAHVGECHNVWATHACVPTDPNPQEIHLENVTE
AB052867_V1V2        VPVWKDAETTLFCASDAKAYDAECHNVWATHACVPTDPNPQEISLENVTE
yu2gp120_V1V2        VPVWKEATTTLFCASDAKAYDTECHNVWATHACVPTDPNPQEVKLENVTE
HXB2_V1V2            VPVWKEATTTLFCASDAKAYDTECHNVWATHACVPTDPNPQEVVLVNVTE
HM623558_V1V2        VPVWKEAKTTLFCASDAKAYERECHNVWATHACVPTDPNPQEIALENVTE
DQ404010_V1V2        VPVWKEAKTTLFCASDAKAYEKECHNVWATHACVPTDPNPQEMVLENVTE
                     **.*.::  *  *******::    ****:***:*******.***:  : ****

A1_V1V2              EFNMWKNNMVEQMHTDIISLWDQCLKPCVKLTPLCVTLNCSNVNVTN---
A2_V1V2              DFNMWKNNMVEQMHEDIISLWDQCLKPCVKLTPLCVTLNCSNANTTN---
B_V1V2               NFNMWKNNMVEQMHEDIISLWDQCLKPCVKLTPLCVTLNCTDLMNAT--N
C_V1V2               NFNMWKNDMVDQMHEDIISLWDQCLKPCVKLTPLCVTLNCTNATN-A--T
D_V1V2               NFNMWKNNMVEQMHEDIISLWDQCLKPCVKLTPLCVTLNCTDVKRNN---
F1_V1V2              NFDMWKNNMVEQMHTDIISLWDQCLKPCVKLTPLCVTLNCTDVNATN---
F2_V1V2              NFNMWKNNMVDQMHEDIISLWDQCLKPCVKLTPLCVTLNCTDVNVTI---
G_V1V2               NFNMWKNNMVEQMHEDIISLWDECLKPCVKLTPLCVTLNCTDVNVTN---
H_V1V2               NFNMWENDMVEQMHTDIISLWDQCLKPCVKLTPLCVTLDCSNVNT-T--N
01_AE_V1V2           NFNMWKNNMVEQMQEDVISLWDQCLKPCVKLTPLCVTLNCTNANLTNV-N
02_AG_V1V2           NFNMWKNNMVEQMHEDIISLWDQCLKPCVKLTPLCVTLDCHNNITNS---
03_AB_V1V2           NFNMGKNNMVEQMHEDIISLWDQCLKPCVKLTPLCVTLNCTDLKKNV---
04_CPX_V1V2          NFNMWKNNMVEQMHEDIISLWDECLKPCVKLTPLCVALNCSNATINN---
06_CPX_V1V2          NFNMWKNHMVEQMHEDIISLWDECLKPCVKLTPLCVTLNCTNVTKNN---
08_BC_V1V2           NFNMWNNDMVNQMHEDVISLWDQCLKPCVKLTPLCVTLECTNVSSNG--N
10_CD_V1V2           NFNMWKNGMVDQMHEDIISLWDQCLKPCVKLTPLCVTLNCSDVNATN---
11_CPX_V1V2          NFNMWKNNMVEQMHEDIISLWDECLKPCVKLTPLCVTLNCTDVKNAT---
12_BF_V1V2           NFDMWKNNMVEQMHTDIISLWDQCLKPCVKLTPLCVTLNCTDANATA---
14_BG_V1V2           NFNMWENNMVDQMQEDIISLWDQCLKPCVELTPLCVTLNCTDFNNTT--N
CON_OF_CONS_V1V2     NFNMWKNNMVEQMHEDIISLWDQCLKPCVKLTPLCVTLNCTDVNATN---
AB097872_V1V2        NFNMWKNKMADQMQEDVISLWDQCLKPCVKLTPLCVTLNCTDAQVNQTWN
AB052867_V1V2        DFNMWKNKMVEQMHVDIISLWDQCLKPCVKLTPLCVTLDCHDNITTS---
yu2gp120_V1V2        NFNMWKNNMVEQMHEDIISLWDQCLKPCVKLTPLCVTLNCTDLRNAT--N
HXB2_V1V2            NFNMWKNDMVEQMHEDIISLWDQCLKPCVKLTPLCVSLKCTDLKNDT--N
HM623558_V1V2        NFNMWKNNMVDQMHEDIISLWDQCLKPCVKLTPLCVTLNCTNVTKND--T
DQ404010_V1V2        NFNMWKNDMVNQMHEDVISLWDQCLKPCVKLTPLCVTLECGNVTQNG--T
                     :*:*  :*  *.:**: *:*****:*******:******:*.* :
```

FIG. 3 (continued)

```
A1_V1V2          NTT---N------THEEEIKNCSFNMTTELRDKKQKVYSLFYRLDVVQIN
A2_V1V2          NST-----------MEEIKNCSYNITTELRDKTQKVYSLFYKLDVVQLD
B_V1V2           TNT---TI--I-YRWRGEIKNCSFNITTSIRDKVQKEYALFYKLDVVPID
C_V1V2           ------N-------TMGEIKNCSFNITTELRDKKQKVYALFYRLDIVPLN
D_V1V2           TSN---D------TNEGEMKNCSFNITTEIRDKKKQVHALFYKLDVVPID
F1_V1V2          NDT---ND-N----KTGAIQNCSFNMTTEVRDKKLKVHALFYKLDIVPIS
F2_V1V2          NTT---N------VTLGEIKNCSFNITTEIKDKKKKEYALFYRLDVVPIN
G_V1V2           NNT---N------NTKKEIKNCSFNITTEIRDKKKKEYALFYRLDVVPIN
H_V1V2           ATN---SR----FNMQEELTNCSFNVTTVIRDKQQKVHALFYRLDVVPID
01_AE_V1V2       NIT---NVSNIIGNITNEVRNCSFNMTTELRDKKQKVHALFYKLDIVQIE
02_AG_V1V2       NTT---N------NNAGEIKNCSFNMTTELRDKKQKVYALFYRLDVVQIN
03_AB_V1V2       TST---NT-S--SIKMMEMKNCSFNITTDLRDKVKKEYALFYKLDVVQID
04_CPX_V1V2      STK---T------NSTEEIKNCSFNITTEIRDKKKKEYALFYRLDIVPIN
06_CPX_V1V2      NTK---I------MGREEIKNCSFNVTTEIRDKKKKEYALFYRLDVVPID
08_BC_V1V2       GTY---NE-TY-NESVKEIKNCSFNATTLLRDRKKTVYALFYRLDIVPLN
10_CD_V1V2       SAT---N------TVVAGMKNCSFNITTEIRDKKKQEYALFYKLDVVQID
11_CPX_V1V2      NT----T------VEAAEIKNCSFNITTEIKDKKKKEYALFYRLDVVPIN
12_BF_V1V2       NAT---KE-HP-EGRAGAIQNCSFNMTTEVRDKQMKVQALFYRLDIVPIS
14_BG_V1V2       NTT---NT--R-NDGEGEIKNCSFNITTSLRDKIKKEYALFYNLDVVQMD
CON_OF_CONS_V1V2 NTT---N--------NEEIKNCSFNITTEIRDKKKKVYALFYKLDVVPID
AB097872_V1V2    NVTKADNITNL-ENITNEVKNCSFNMTTEIRDKQQRVQALFYKLDIVPIG
AB052867_V1V2    GNR---NI-S--VEMKGEIKNCSFNMTTVLRDKKEKVTALFYRLDVVQIN
yu2gp120_V1V2    TTS---SS-WE-TMEKGEIKNCSFNITTSIRDKVQKEYALFYNLDVVPID
HXB2_V1V2        TNS---SS-GRMIMEKGEIKNCSFNISTSIRGKVQKEYAFFYKLDIIPID
HM623558_V1V2    NA----NN-T--AEGKEERKNCSFNATTELRDKNRKVYALFYKLDIVPLN
DQ404010_V1V2    Y-----ND-----ESNKEITNCFNTTTEIRGRKQKVYALFYKLDIVPIS
                             **::* :*  ::.:        ::**.**:: :

A1_V1V2          EN--NS----NSSYRLINCNTSAITQACPKVSFEPIPIHYCAPAGFAILK
A2_V1V2          ES--NKS---EYYYRLINCNTSAITQACPKVSFEPIPIHYCAPAGFAILK
B_V1V2           ND--N------TSYRLISCNTSVITQACPKVSFEPIPIHYCAPAGFAILK
C_V1V2           EN---N------SYRLINCNTSAITQACPKVSFDPIPIHYCAPAGYAILK
D_V1V2           DN--NS----NTSYRLINCNTSAITQACPKVTFEPIPIHYCAPAGFAILK
F1_V1V2          NN--N------SKYRLINCNTSTITQACPKVSWDPIPIHYCAPAGYAILK
F2_V1V2          NS--------IVYRLISCNTSTVTQACPKVSFEPIPIHYCAPAGFAILK
G_V1V2           DN--GN----SSIYRLINCNVSTIKQACPKVTFDPIPIHYCAPAGFAILK
H_V1V2           DN--NS-----YQYRLINCNTSVITQACPKVSFEPIPIHYCAPAGFAILK
01_AE_V1V2       DN--N-------SYRLINCNTSVIKQACPKISFDPIPIHYCTPAGYAILK
02_AG_V1V2       KN--N------SQYRLINCNTSAITQACPKVSFEPIPIHYCAPAGFAILK
03_AB_V1V2       ND---------SYRLISCNTSVVTQACPKISFEPIPIHYCAPAGFAILK
04_CPX_V1V2      DSANNNS--INSEYMLINCNASTIKQACPKVTFEPIPIHYCAPAGFAILK
06_CPX_V1V2      DN--N------NSYRLINCNASTIKQACPKVSFEPIPIHYCAPAGFAILK
08_BC_V1V2       DE--NSGKNSSEYYRLINCNTSAITQACPKVTFDPIPIHYCTPAGYAILK
10_CD_V1V2       GS--N------TSYRLINCNTSAITQACPKVTFEPIPIHYCAPAGFAILK
11_CPX_V1V2      DN--N-----NSIYRLINCNVSTVKQACPKVTFEPIPIHYCAPAGFAILK
12_BF_V1V2       DN--NS-----NEYRLINCNTSTITQACPKVSWDPIPIHYCAPAGYAILK
14_BG_V1V2       ND--N------SSYRLTSCNTSIITQACPKVSFTPIPIHYCAPAGFVILK
CON_OF_CONS_V1V2 DN--N-------SYRLINCNTSAITQACPKVSFEPIPIHYCAPAGFAILK
AB097872_V1V2    NN--NNK--TSGEYRLINCNTSVIKQACPKVSFDPIPIHYCTPAGFAILK
AB052867_V1V2    NN--SSN---SSLYRLINCNTSTTQACPKVTFEPIPIHYCAPAGFAILK
yu2gp120_V1V2    N---------ASYRLISCNTSVITQACPKVSFEPIPIHYCAPAGFAILK
HXB2_V1V2        ND--T------TSYKLTSCNTSVITQACPKVSFEPIPIHYCAPAGFAILK
HM623558_V1V2    PS--NNS-NSSGQYRLITCNTSVITQACPKIIFDPIPIHYCAPAGYAILK
DQ404010_V1V2    ET--SN------QSRLISCNTSVITQACPKVSFDPIPIHYCTPAGYAILK
                 *  .**.*   .*****:  : ********:***:.***
```

FIG. 3 (continued)

```
A1_V1V2              CKDKEFNGTGPCKNVSTVQCTHGIKPVVSTGGGDMRDNWRSELYKYKVVK
A2_V1V2              CKDPRFNGTGSCNNVSSVQCTHGIKPVASTGGGDMRDNWRSELYKYKVVK
B_V1V2               CNDKKFNGTGPCTNVSTVQCTHGIRPVVSTGGGDMRDNWRSELYKYKVVK
C_V1V2               CNNKTFNGTGPCNNVSTVQCTHGIKPVVSTGGGDMRDNWRSELYKYKVVE
D_V1V2               CKDKKFNGTGPCKNVSTVQCTHGIRPVVSTGGGDMRDNWRSELYKYKVVK
F1_V1V2              CNDKRFNGTGPCKNVSTVQCTHGIKPVVSTGGGNMKDNWRSELYKYKVVE
F2_V1V2              CNDKKFNGTGLCRNVSTVQCTHGIRPVVSTGGGDMRDNWRSELYKYKVVK
G_V1V2               CRDKKFNGTGPCKNVSTVQCTHGIKPVVSTGGGDMRDNWRSELYKYKIVK
H_V1V2               CNNKTFNGTGPCTNVSTVQCTHGIRPVVSTGGGDMRDNWRSELYKYKVVK
01_AE_V1V2           CNDKNFNGTGPCKNVSSVQCTHGIKPVVSTGGGNIKDNWRSELYKYKVVQ
02_AG_V1V2           CNDKEFNGTGPCKNVSTVQCTHGIKPVVSTGGGDMRDNWRSELYKYKVVK
03_AB_V1V2           CNDKKFNGTGPCTNVSTVQCTHGIKPVVSTGGGDMRDNWRSELYKYKVVK
04_CPX_V1V2          CNDKNFTGLGPCTNVSSVQCTHGIKPVVSTGGGDMRDNWRSELYKYKVVK
06_CPX_V1V2          CRDKNFNGTGPCKNVSTVQCTHGIKPVVSTGGGDMRDNWRSELYKYKVVK
08_BC_V1V2           CNDKKFNGTGQCHNVSTVQCTHGIKPVVSTGGGDMRNNWRNELYKYKVVE
10_CD_V1V2           CNDKKFNGTGPCKNVSTVQCTHGIKPVVSTGGGDMRDNWRSELYKYKVVK
11_CPX_V1V2          CNDKKFNGTGPCKNVSTVQCTHGIKPVVSTTGGDMRDNWRSELYKYKVVE
12_BF_V1V2           CNDKKFNGTGPCKNVSTVQCTHGIKPVVSTGGGNMKDNWRSELYKYKVVE
14_BG_V1V2           CNNKTFNGTGPCTNVSTVQCTHGIRPVVSTGGGNMKDNWRSELYKYKVVK
CON_OF_CONS_V1V2     CNDKKFNGTGPCKNVSTVQCTHGIKPVVSTGGGDMRDNWRSELYKYKVVK
AB097872_V1V2        CNDKKFNGTGPCKNVSSVQCTHGIKPVVSTGGGNIKDNWRSELYKYKVVE
AB052867_V1V2        CNDKKFNGTGPCKNVSSVQCTHGIRPVVSTGGGDMRDNWRSELYKYKVVK
yu2gp120_V1V2        CNDKKFNGTGPCTNVSTVQCTHGIRPVVSTGGGDMRDNWRSELYKYKVVK
HXB2_V1V2            CNNKTFNGTGPCTNVSTVQCTHGIRPVVSTGGGDMRDNWRSELYKYKVVK
HM623558_V1V2        CNNKTFNGTGPCNNVSTVQCTHGIKPVVSTGGGDMRDNWRSELYKYKVVQ
DQ404010_V1V2        CNDKTFNGTGPCRNVSTVQCTHGIKPVVSTGGGDMRDNWRSELYKYKVVE
                     *.:  *.* * * ***:*******:**.** **:::***.******:*:

A1_V1V2              IEPLGVAPTRAKRRVVEREKR
A2_V1V2              IEPLGVAPTRAKRRVVEREKR
B_V1V2               IEPLGVAPTKAKRRVVQREKR
C_V1V2               IKPLGIAPTKAKRRVVEREKR
D_V1V2               IEPLGVAPTRAKRRVVEREKR
F1_V1V2              IEPLGVAPTKAKRQVVKRERR
F2_V1V2              IEPLGVAPTKAKRQVVQREKR
G_V1V2               IKPLGVAPTRARRRVVEREKR
H_V1V2               IEPLGVAPTEARRRVVEREKR
01_AE_V1V2           IEPLGIAPTRAKRRVVEREKR
02_AG_V1V2           IEPLGVAPTRAKRRVVEREKR
03_AB_V1V2           IEPLGVAPTKAKRRVVQREKR
04_CPX_V1V2          IEPVGVAPTRARRRVVQREKR
06_CPX_V1V2          IKPLGIAPTRARRRVVGREKR
08_BC_V1V2           IKPLGVAPTAAKRRVVEREKR
10_CD_V1V2           IEPLGLAPTKAKRRVVEREKR
11_CPX_V1V2          IKPLGVAPTRAKRRVVEREKR
12_BF_V1V2           IEPLGVAPTRAKRQVVKREKR
14_BG_V1V2           IEPLGVAPTRAKRRVVQREKR
CON_OF_CONS_V1V2     IEPLGVAPTKAKRRVVEREKR
AB097872_V1V2        IEPLGIAPTRAKRRVVERQKR
AB052867_V1V2        LEPLGVAPTRARRRVVTREKR
yu2gp120_V1V2        IEPLGVAPTKAKRRVVQREKR
HXB2_V1V2            IEPLGVAPTKAKRRVVQREKR
HM623558_V1V2        IEPLGVAPTKAKRRVVQREKR
DQ404010_V1V2        IKPLGVAPTTAKRRVVEREKR
                     ::*:*:*** *:*:** *::*
```

FIG. 4 – Alignment of ID immunogens lacking V1V2 region (clades)

```
A1              VPVWKDAETTLFCASDAKAYETECHNVWATHACVPTDPNPQEIHLENVTE
A2              VPVWKDADTTLFCASDAKAYDTECHNVWATHACVPTDPNPQEVNLENVTE
B               VPVWKEATTTLFCASDAKAYDTECHNVWATHACVPTDPNPQEVVLENVTE
C               VPVWKEAKTTLFCASDAKAYEKECHNVWATHACVPTDPNPQEIVLENVTE
D               VPVWKEATTTLFCASDAKSYKTECHNIWATHACVPTDPNPQEIELENVTE
F1              VPVWKEATTTLFCASDAKSYEKECHNVWATHACVPTDPNPQEVVLENVTE
F2              VPVWKEATTTLFCASDAKAYERECHNVWATYACVPTDPSPQELVLGNVTE
G               VPVWEDADTTLFCASDAKAYSTECHNVWATHACVPTDPNPQEITLENVTE
H               VPVWKEAKTTLFCASDAKAYETECHNVWATHACVPTDPNPQEMVLENVTE
01_AE           VPVWRDADTTLFCASDAKAHETECHNVWATHACVPTDPNPQEIHLENVTE
02_AG           VPVWRDAETTLFCASDAKAYDTECHNVWATHACVPTDPNPQEIHLENVTE
03_AB           VPVWKEATTTLFCASDAKAYSKECHNVWATYACVPTDPSPQEIPLENVTE
04_CPX          VPVWRDAETTPFCASDAKAYDKECHNIWATHACVPTDPNPQEIALKNVTE
06_CPX          VPAWEDADTILFCASDAKAYSAECHNVWATHACVPTDPNPQEIALENVTE
08_BC           VPVWKEAKTTLFCASDAKAYETECHNVWATHACVPTDPNPQEIVMENVTE
10_CD           VPVWKETTTTLFCASDAKAYKAECHNIWATHACVPTDPNPQEIVLENVTE
11_CPX          VPVWKDADTTLFCASDAKAYSTECHNVWATHACVPTDPNPQEIPLENVTE
12_BF           VPVWKEATTTLFCASDAKSYERECHNVWATHACVPTDPNPQEVDLENVTE
14_BG           VPVWKEATTTLFCASDAKAYDAECHNVWATHACVPTDPNPQEVALENVTE
CON_OF_CONS     VPVWKEANTTLFCASDAKAYDTECHNVWATHACVPTDPNPQEIVLENVTE
                **.*.:: *   ******::. ****:***:*******.***: : ****

A1              EFNMWKNNMVEQMHTDIISLWDQCLKPGGAPKVSFEPIPIHYCAPAGFAI
A2              DFNMWKNNMVEQMHEDIISLWDQCLKPGGAPKVSFEPIPIHYCAPAGFAI
B               NFNMWKNNMVEQMHEDIISLWDQCLKPGGAPKVSFEPIPIHYCAPAGFAI
C               NFNMWKNDMVDQMHEDIISLWDQCLKPGGAPKVSFDPIPIHYCAPAGYAI
D               NFNMWKNNMVEQMHEDIISLWDQCLKPGGAPKVTFEPIPIHYCAPAGFAI
F1              NFDMWKNNMVEQMHTDIISLWDQCLKPGGAPKVSWDPIPIHYCAPAGYAI
F2              NFNMWKNNMVDQMHEDIISLWDQCLKPGGAPKVSFEPIPIHYCAPAGFAI
G               NFNMWKNNMVEQMHEDIISLWDECLKPGGAPKVTFDPIPIHYCAPAGFAI
H               NFNMWENDMVEQMHTDIISLWDQCLKPGGAPKVSFEPIPIHYCAPAGFAI
01_AE           NFNMWKNNMVEQMQEDVISLWDQCLKPGGAPKISFDPIPIHYCTPAGYAI
02_AG           NFNMWKNNMVEQMHEDIISLWDQCLKPGGAPKVSFEPIPIHYCAPAGFAI
03_AB           NFNMGKNNMVEQMHEDIISLWDQCLKPGGAPKISFEPIPIHYCAPAGFAI
04_CPX          NFNMWKNNMVEQMHEDIISLWDECLKPGGAPKVTFEPIPIHYCAPAGFAI
06_CPX          NFNMWKNHMVEQMHEDIISLWDECLKPGGAPKVSFEPIPIHYCAPAGFAI
08_BC           NFNMWNNDMVNQMHEDVISLWDQCLKPGGAPKVTFDPIPIHYCTPAGYAI
10_CD           NFNMWKNGMVDQMHEDIISLWDQCLKPGGAPKVTFEPIPIHYCAPAGFAI
11_CPX          NFNMWKNNMVEQMHEDIISLWDECLKPGGAPKVTFEPIPIHYCAPAGFAI
12_BF           NFDMWKNNMVEQMHTDIISLWDQCLKPGGAPKVSWDPIPIHYCAPAGYAI
14_BG           NFNMWENNMVDQMQEDIISLWDQCLKPGGAPKVSFTPIPIHYCAPAGFVI
CON_OF_CONS     NFNMWKNNMVEQMHEDIISLWDQCLKPGGAPKVSFEPIPIHYCAPAGFAI
                :*:*  :*  **:**: *:****:*******::: *******:***:.*
```

FIG. 4 (continued)

```
A1           LKCKDKEFNGTGPCKNVSTVQCTHGIKPVVSTGGGDMRDNWRSELYKYKV
A2           LKCKDPRFNGTGSCNNVSSVQCTHGIKPVASTGGGDMRDNWRSELYKYKV
B            LKCNDKKFNGTGPCTNVSTVQCTHGIRPVVSTGGGDMRDNWRSELYKYKV
C            LKCNNKTFNGTGPCNNVSTVQCTHGIKPVVSTGGGDMRDNWRSELYKYKV
D            LKCKDKKFNGTGPCKNVSTVQCTHGIRPVVSTGGGDMRDNWRSELYKYKV
F1           LKCNDKRFNGTGPCKNVSTVQCTHGIKPVVSTGGGNMKDNWRSELYKYKV
F2           LKCNDKKFNGTGLCRNVSTVQCTHGIRPVVSTGGGDMRDNWRSELYKYKV
G            LKCRDKKFNGTGPCKNVSTVQCTHGIKPVVSTGGGDMRDNWRSELYKYKI
H            LKCNNKTFNGTGPCTNVSTVQCTHGIRPVVSTGGGDMRDNWRSELYKYKV
01_AE        LKCNDKNFNGTGPCKNVSSVQCTHGIKPVVSTGGGNIKDNWRSELYKYKV
02_AG        LKCNDKEFNGTGPCKNVSTVQCTHGIKPVVSTGGGDMRDNWRSELYKYKV
03_AB        LKCNDKKFNGTGPCTNVSTVQCTHGIKPVVSTGGGDMRDNWRSELYKYKV
04_CPX       LKCNDKNFTGLGPCTNVSSVQCTHGIKPVVSTGGGDMRDNWRSELYKYKV
06_CPX       LKCRDKNFNGTGPCKNVSTVQCTHGIKPVVSTGGGDMRDNWRSELYKYKV
08_BC        LKCNDKKFNGTGQCHNVSTVQCTHGIKPVVSTGGGDMRNNWRNELYKYKV
10_CD        LKCNDKKFNGTGPCKNVSTVQCTHGIKPVVSTGGGDMRDNWRSELYKYKV
11_CPX       LKCNDKKFNGTGPCKNVSTVQCTHGIKPVVSTTGGDMRDNWRSELYKYKV
12_BF        LKCNDKKFNGTGPCKNVSTVQCTHGIKPVVSTGGGNMKDNWRSELYKYKV
14_BG        LKCNNKTFNGTGPCTNVSTVQCTHGIRPVVSTGGGNMKDNWRSELYKYKV
CON_OF_CONS  LKCNDKKFNGTGPCKNVSTVQCTHGIKPVVSTGGGDMRDNWRSELYKYKV
             ***.:   *.* * * ***:*******:**.** **:::.***.******:

A1           VKIEPLGVAPTRAKRRVVEREKR
A2           VKIEPLGVAPTRAKRRVVEREKR
B            VKIEPLGVAPTKAKRRVVQREKR
C            VEIKPLGIAPTKAKRRVVEREKR
D            VKIEPLGVAPTRAKRRVVEREKR
F1           VEIEPLGVAPTKAKRQVVKRERR
F2           VKIEPLGVAPTKAKRQVVQREKR
G            VKIKPLGVAPTRARRRVVEREKR
H            VKIEPLGVAPTEARRRVVEREKR
01_AE        VQIEPLGIAPTRAKRRVVEREKR
02_AG        VKIEPLGVAPTRAKRRVVEREKR
03_AB        VKIEPLGVAPTKAKRRVVQREKR
04_CPX       VKIEPVGVAPTRARRRVVQREKR
06_CPX       VKIKPLGIAPTRARRRVVGREKR
08_BC        VEIKPLGVAPTAAKRRVVEREKR
10_CD        VKIEPLGLAPTKAKRRVVEREKR
11_CPX       VEIKPLGVAPTRAKRRVVEREKR
12_BF        VEIEPLGVAPTRAKRQVVKREKR
14_BG        VKIEPLGVAPTRAKRRVVQREKR
CON_OF_CONS  VKIEPLGVAPTKAKRRVVEREKR
             *:*:*:*:*** *:*:** **:*
```

FIG. 5 – Alignment of ID immunogens lacking V1V2 region (strains)

```
AB097872     VPVWRDAETTLFCASDAKAHVGECHNVWATHACVPTDPNPQEIHLENVTE
AB052867     VPVWKDAETTLFCASDAKAYDAECHNVWATHACVPTDPNPQEISLENVTE
yu2gp120     VPVWKEATTTLFCASDAKAYDTECHNVWATHACVPTDPNPQEVKLENVTE
HXB2         VPVWKEATTTLFCASDAKAYDTECHNVWATHACVPTDPNPQEVVLVNVTE
HM623558     VPVWKEAKTTLFCASDAKAYERECHNVWATHACVPTDPNPQEIALENVTE
DQ404010     VPVWKEAKTTLFCASDAKAYEKECHNVWATHACVPTDPNPQEMVLENVTE
             ****::* **********:  ******************: * ****

AB097872     NFNMWKNKMADQMQEDVISLWDQCLKPGGAPKVSFDPIPIHYCTPAGFAI
AB052867     DFNMWKNKMVEQMHVDIISLWDQCLKPGGAPKVTFEPIPIHYCAPAGFAI
yu2gp120     NFNMWKNNMVEQMHEDIISLWDQCLKPGGAPKVSFEPIPIHYCAPAGFAI
HXB2         NFNMWKNDMVEQMHEDIISLWDQCLKPGGAPKVSFEPIPIHYCAPAGFAI
HM623558     NFNMWKNNMVDQMHEDIISLWDQCLKPGGAPKIIFDPIPIHYCAPAGYAI
DQ404010     NFNMWKNDMVNQMHEDVISLWDQCLKPGGAPKVSFDPIPIHYCTPAGYAI
             :*****.*.:**: *:**************: *:*******:***.**

AB097872     LKCNDKKFNGTGPCKNVSSVQCTHGIKPVVSTGGGNIKDNWRSELYKYKV
AB052867     LKCNDKKFNGTGPCKNVSSVQCTHGIRPVVSTGGGDMRDNWRSELYKYKV
yu2gp120     LKCNDKKFNGTGPCTNVSTVQCTHGIRPVVSTGGGDMRDNWRSELYKYKV
HXB2         LKCNNKTFNGTGPCTNVSTVQCTHGIRPVVSTGGGDMRDNWRSELYKYKV
HM623558     LKCNNKTFNGTGPCNNVSTVQCTHGIKPVVSTGGGDMRDNWRSELYKYKV
DQ404010     LKCNDKTFNGTGPCRNVSTVQCTHGIKPVVSTGGGDMRDNWRSELYKYKV
             ****:*.******* ***:******:*******:::************

AB097872     VEIEPLGIAPTRAKRRVVERQKR
AB052867     VKLEPLGVAPTRARRRVVTREKR
yu2gp120     VKIEPLGVAPTKAKRRVVQREKR
HXB2         VKIEPLGVAPTKAKRRVVQREKR
HM623558     VQIEPLGVAPTKAKRRVVQREKR
DQ404010     VEIKPLGVAPTTAKRRVVEREKR
             *:::***:*** *:**** *:**
```

FIG. 6 – Alignment of ID immunogens lacking V1V2 region (clades and strains)

```
A1              VPVWKDAETTLFCASDAKAYETECHNVWATHACVPTDPNPQEIHLENVTE
A2              VPVWKDADTTLFCASDAKAYDTECHNVWATHACVPTDPNPQEVNLENVTE
B               VPVWKEATTTLFCASDAKAYDTECHNVWATHACVPTDPNPQEVVLENVTE
C               VPVWKEAKTTLFCASDAKAYEKECHNVWATHACVPTDPNPQEIVLENVTE
D               VPVWKEATTTLFCASDAKSYKTECHNIWATHACVPTDPNPQEIELENVTE
F1              VPVWKEATTTLFCASDAKSYEKECHNVWATHACVPTDPNPQEVVLENVTE
F2              VPVWKEATTTLFCASDAKAYERECHNVWATYACVPTDPSPQELVLGNVTE
G               VPVWEDADTTLFCASDAKAYSTECHNVWATHACVPTDPNPQEITLENVTE
H               VPVWKEAKTTLFCASDAKAYETECHNVWATHACVPTDPNPQEMVLENVTE
01_AE           VPVWRDADTTLFCASDAKAHETECHNVWATHACVPTDPNPQEIHLENVTE
02_AG           VPVWRDAETTLFCASDAKAYDTECHNVWATHACVPTDPNPQEIHLENVTE
03_AB           VPVWKEATTTLFCASDAKAYSKECHNVWATYACVPTDPSPQEIPLENVTE
04_CPX          VPVWRDAETTPFCASDAKAYDKECHNIWATHACVPTDPNPQEIALKNVTE
06_CPX          VPAWEDADTILFCASDAKAYSAECHNVWATHACVPTDPNPQEIALENVTE
08_BC           VPVWKEAKTTLFCASDAKAYETECHNVWATHACVPTDPNPQEIVMENVTE
10_CD           VPVWKETTTTLFCASDAKAYKAECHNIWATHACVPTDPNPQEIVLENVTE
11_CPX          VPVWKDADTTLFCASDAKAYSTECHNVWATHACVPTDPNPQEIPLENVTE
12_BF           VPVWKEATTTLFCASDAKSYERECHNVWATHACVPTDPNPQEVDLENVTE
14_BG           VPVWKEATTTLFCASDAKAYDAECHNVWATHACVPTDPNPQEVALENVTE
CON_OF_CONS     VPVWKEANTTLFCASDAKAYDTECHNVWATHACVPTDPNPQEIVLENVTE
AB097872        VPVWRDAETTLFCASDAKAHVGECHNVWATHACVPTDPNPQEIHLENVTE
AB052867        VPVWKDAETTLFCASDAKAYDAECHNVWATHACVPTDPNPQEISLENVTE
yu2gp120        VPVWKEATTTLFCASDAKAYDTECHNVWATHACVPTDPNPQEVKLENVTE
HXB2            VPVWKEATTTLFCASDAKAYDTECHNVWATHACVPTDPNPQEVVLVNVTE
HM623558        VPVWKEAKTTLFCASDAKAYERECHNVWATHACVPTDPNPQEIALENVTE
DQ404010        VPVWKEAKTTLFCASDAKAYEKECHNVWATHACVPTDPNPQEMVLENVTE
                **.*.::  *   *******::   ****:***:******.***: : ****

A1              EFNMWKNNMVEQMHTDIISLWDQCLKPGGAPKVSFEPIPIHYCAPAGFAI
A2              DFNMWKNNMVEQMHEDIISLWDQCLKPGGAPKVSFEPIPIHYCAPAGFAI
B               NFNMWKNNMVEQMHEDIISLWDQCLKPGGAPKVSFEPIPIHYCAPAGFAI
C               NFNMWKNDMVDQMHEDIISLWDQCLKPGGAPKVSFDPIPIHYCAPAGYAI
D               NFNMWKNNMVEQMHEDIISLWDQCLKPGGAPKVTFEPIPIHYCAPAGFAI
F1              NFDMWKNNMVEQMHTDIISLWDQCLKPGGAPKVSWDPIPIHYCAPAGYAI
F2              NFNMWKNNMVDQMHEDIISLWDQCLKPGGAPKVSFEPIPIHYCAPAGFAI
G               NFNMWKNNMVEQMHEDIISLWDECLKPGGAPKVTFDPIPIHYCAPAGFAI
H               NFNMWENDMVEQMHTDIISLWDQCLKPGGAPKVSFEPIPIHYCAPAGFAI
01_AE           NFNMWKNNMVEQMQEDVISLWDQCLKPGGAPKISFDPIPIHYCTPAGYAI
02_AG           NFNMWKNNMVEQMHEDIISLWDQCLKPGGAPKVSFEPIPIHYCAPAGFAI
03_AB           NFNMGKNNMVEQMHEDIISLWDQCLKPGGAPKISFEPIPIHYCAPAGFAI
04_CPX          NFNMWKNNMVEQMHEDIISLWDECLKPGGAPKVTFEPIPIHYCAPAGFAI
06_CPX          NFNMWKNHMVEQMHEDIISLWDECLKPGGAPKVSFEPIPIHYCAPAGFAI
08_BC           NFNMWNNDMVNQMHEDVISLWDQCLKPGGAPKVTFDPIPIHYCTPAGYAI
10_CD           NFNMWKNGMVDQMHEDIISLWDQCLKPGGAPKVTFEPIPIHYCAPAGFAI
11_CPX          NFNMWKNNMVEQMHEDIISLWDECLKPGGAPKVTFEPIPIHYCAPAGFAI
12_BF           NFDMWKNNMVEQMHTDIISLWDQCLKPGGAPKVSWDPIPIHYCAPAGYAI
14_BG           NFNMWENNMVDQMQEDIISLWDQCLKPGGAPKVSFTPIPIHYCAPAGFVI
CON_OF_CONS     NFNMWKNNMVEQMHEDIISLWDQCLKPGGAPKVSFEPIPIHYCAPAGFAI
AB097872        NFNMWKNKMADQMQEDVISLWDQCLKPGGAPKVSFDPIPIHYCTPAGFAI
AB052867        DFNMWKNKMVEQMHVDIISLWDQCLKPGGAPKVTFEPIPIHYCAPAGFAI
yu2gp120        NFNMWKNNMVEQMHEDIISLWDQCLKPGGAPKVSFEPIPIHYCAPAGFAI
HXB2            NFNMWKNDMVEQMHEDIISLWDQCLKPGGAPKVSFEPIPIHYCAPAGFAI
HM623558        NFNMWKNNMVDQMHEDIISLWDQCLKPGGAPKIIFDPIPIHYCAPAGYAI
DQ404010        NFNMWKNDMVNQMHEDVISLWDQCLKPGGAPKVSFDPIPIHYCTPAGYAI
                :*:*  :*  *.:**: *:*****:*********: : *******:***:.*
```

FIG. 6 (continued)

```
A1          LKCKDKEFNGTGPCKNVSTVQCTHGIKPVVSTGGGDMRDNWRSELYKYKV
A2          LKCKDPRFNGTGSCNNVSSVQCTHGIKPVASTGGGDMRDNWRSELYKYKV
B           LKCNDKKFNGTGPCTNVSTVQCTHGIRPVVSTGGGDMRDNWRSELYKYKV
C           LKCNNKTFNGTGPCNNVSTVQCTHGIKPVVSTGGGDMRDNWRSELYKYKV
D           LKCKDKKFNGTGPCKNVSTVQCTHGIRPVVSTGGGDMRDNWRSELYKYKV
F1          LKCNDKRFNGTGPCKNVSTVQCTHGIKPVVSTGGGNMKDNWRSELYKYKV
F2          LKCNDKKFNGTGLCRNVSTVQCTHGIRPVVSTGGGDMRDNWRSELYKYKV
G           LKCRDKKFNGTGPCKNVSTVQCTHGIKPVVSTGGGDMRDNWRSELYKYKI
H           LKCNNKTFNGTGPCTNVSTVQCTHGIRPVVSTGGGDMRDNWRSELYKYKV
01_AE       LKCNDKNFNGTGPCKNVSSVQCTHGIKPVVSTGGGNIKDNWRSELYKYKV
02_AG       LKCNDKEFNGTGPCKNVSTVQCTHGIKPVVSTGGGDMRDNWRSELYKYKV
03_AB       LKCNDKKFNGTGPCTNVSTVQCTHGIKPVVSTGGGDMRDNWRSELYKYKV
04_CPX      LKCNDKNFTGLGPCTNVSSVQCTHGIKPVVSTGGGDMRDNWRSELYKYKV
06_CPX      LKCRDKNFNGTGPCKNVSTVQCTHGIKPVVSTGGGDMRDNWRSELYKYKV
08_BC       LKCNDKKFNGTGQCHNVSTVQCTHGIKPVVSTGGGDMRNNWRNELYKYKV
10_CD       LKCNDKKFNGTGPCKNVSTVQCTHGIKPVVSTGGGDMRDNWRSELYKYKV
11_CPX      LKCNDKKFNGTGPCKNVSTVQCTHGIKPVVSTTGGDMRDNWRSELYKYKV
12_BF       LKCNDKKFNGTGPCKNVSTVQCTHGIKPVVSTGGGNMKDNWRSELYKYKV
14_BG       LKCNNKTFNGTGPCTNVSTVQCTHGIRPVVSTGGGNMKDNWRSELYKYKV
CON_OF_CONS LKCNDKKFNGTGPCKNVSTVQCTHGIKPVVSTGGGDMRDNWRSELYKYKV
AB097872    LKCNDKKFNGTGPCKNVSSVQCTHGIKPVVSTGGGNIKDNWRSELYKYKV
AB052867    LKCNDKKFNGTGPCKNVSSVQCTHGIRPVVSTGGGDMRDNWRSELYKYKV
yu2gp120    LKCNDKKFNGTGPCTNVSTVQCTHGIRPVVSTGGGDMRDNWRSELYKYKV
HXB2        LKCNNKTFNGTGPCTNVSTVQCTHGIRPVVSTGGGDMRDNWRSELYKYKV
HM623558    LKCNNKTFNGTGPCNNVSTVQCTHGIKPVVSTGGGDMRDNWRSELYKYKV
DQ404010    LKCNDKTFNGTGPCRNVSTVQCTHGIKPVVSTGGGDMRDNWRSELYKYKV
            ***.:  *.* * * ***:*******:**.** **:::***.******:

A1          VKIEPLGVAPTRAKRRVVEREKR
A2          VKIEPLGVAPTRAKRRVVEREKR
B           VKIEPLGVAPTKAKRRVVQREKR
C           VEIKPLGIAPTKAKRRVVEREKR
D           VKIEPLGVAPTRAKRRVVEREKR
F1          VEIEPLGVAPTKAKRQVVKRERR
F2          VKIEPLGVAPTKAKRQVVQREKR
G           VKIKPLGVAPTRARRRVVEREKR
H           VKIEPLGVAPTEARRRVVEREKR
01_AE       VQIEPLGIAPTRAKRRVVEREKR
02_AG       VKIEPLGVAPTRAKRRVVEREKR
03_AB       VKIEPLGVAPTKAKRRVVQREKR
04_CPX      VKIEPVGVAPTRARRRVVQREKR
06_CPX      VKIKPLGIAPTRARRRVVGREKR
08_BC       VEIKPLGVAPTAAKRRVVEREKR
10_CD       VKIEPLGLAPTKAKRRVVEREKR
11_CPX      VEIKPLGVAPTRAKRRVVEREKR
12_BF       VEIEPLGVAPTRAKRQVVKREKR
14_BG       VKIEPLGVAPTRAKRRVVQREKR
CON_OF_CONS VKIEPLGVAPTKAKRRVVEREKR
AB097872    VEIEPLGIAPTRAKRRVVERQKR
AB052867    VKLEPLGVAPTRARRRVVTREKR
yu2gp120    VKIEPLGVAPTKAKRRVVQREKR
HXB2        VKIEPLGVAPTKAKRRVVQREKR
HM623558    VQIEPLGVAPTKAKRRVVQREKR
DQ404010    VEIKPLGVAPTTAKRRVVEREKR
            *:::*:*:*** *:*:** *:::*
```

FIG. 11A
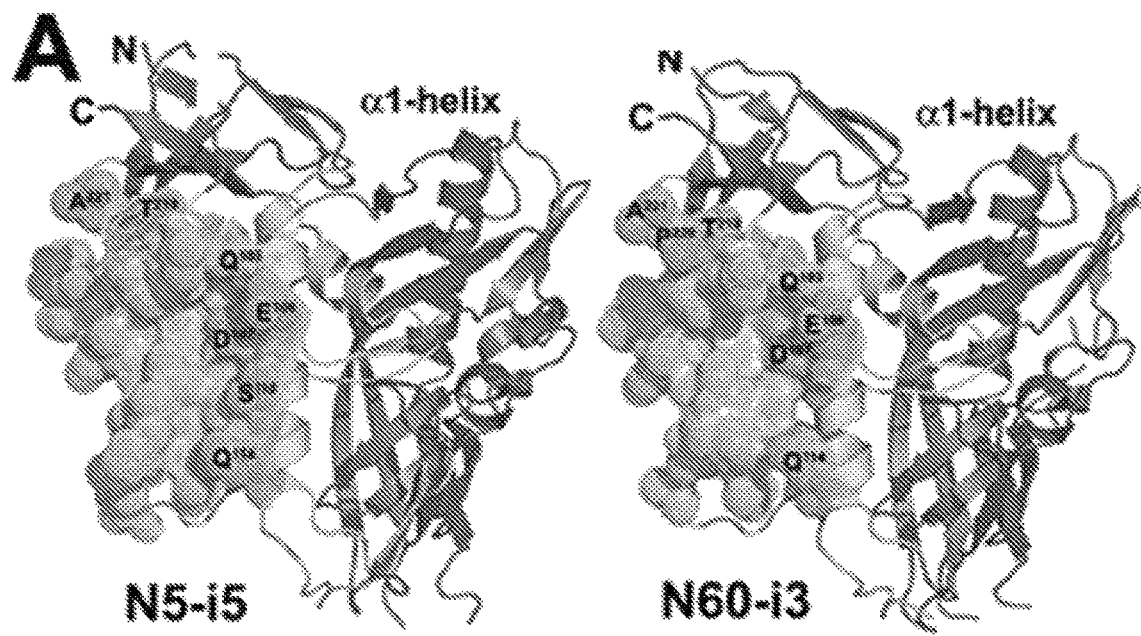
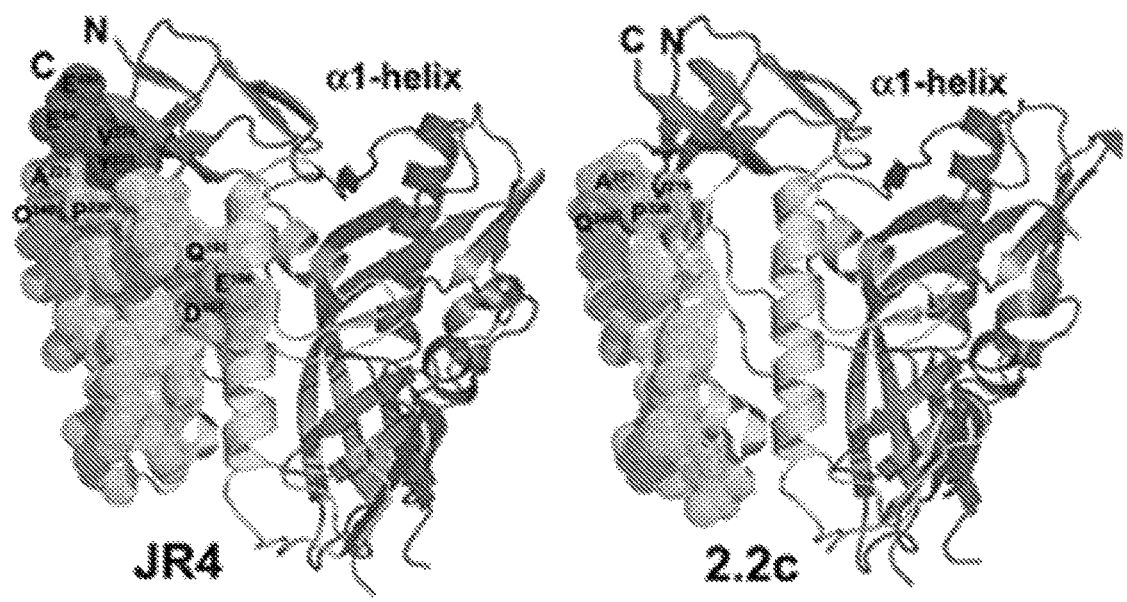

SEQUENCE LISTING

```
<160> NUMBER OF SEQ ID NOS: 61

<210> SEQ ID NO 1
<211> LENGTH: 481
<212> TYPE: PRT
<213> ORGANISM: Human immunodeficiency virus type 1
<220> FEATURE:
<221> NAME/KEY: misc_feature
<223> OTHER INFORMATION: mature gp120 from HIV-1 isolate HXBc2

<400> SEQUENCE: 1

Thr Glu Lys Leu Trp Val Thr Val Tyr Tyr Gly Val Pro Val Trp Lys
1               5                   10                  15

Glu Ala Thr Thr Thr Leu Phe Cys Ala Ser Asp Ala Lys Ala Tyr Asp
            20                  25                  30

Thr Glu Val His Asn Val Trp Ala Thr His Ala Cys Val Pro Thr Asp
        35                  40                  45

Pro Asn Pro Gln Glu Val Val Leu Val Asn Val Thr Glu Asn Phe Asn
    50                  55                  60

Met Trp Lys Asn Asp Met Val Glu Gln Met His Glu Asp Ile Ile Ser
65                  70                  75                  80

Leu Trp Asp Gln Ser Leu Lys Pro Cys Val Lys Leu Thr Pro Leu Cys
                85                  90                  95

Val Ser Leu Lys Cys Thr Asp Leu Lys Asn Asp Thr Asn Thr Asn Ser
            100                 105                 110

Ser Ser Gly Arg Met Ile Met Glu Lys Gly Glu Ile Lys Asn Cys Ser
        115                 120                 125

Phe Asn Ile Ser Thr Ser Ile Arg Gly Lys Val Gln Lys Glu Tyr Ala
    130                 135                 140

Phe Phe Tyr Lys Leu Asp Ile Ile Pro Ile Asp Asn Asp Thr Thr Ser
145                 150                 155                 160

Tyr Lys Leu Thr Ser Cys Asn Thr Ser Val Ile Thr Gln Ala Cys Pro
                165                 170                 175

Lys Val Ser Phe Glu Pro Ile Pro Ile His Tyr Cys Ala Pro Ala Gly
            180                 185                 190

Phe Ala Ile Leu Lys Cys Asn Asn Lys Thr Phe Asn Gly Thr Gly Pro
        195                 200                 205

Cys Thr Asn Val Ser Thr Val Gln Cys Thr His Gly Ile Arg Pro Val
    210                 215                 220
```

```
Val Ser Thr Gln Leu Leu Asn Gly Ser Leu Ala Glu Glu Val
225                 230                 235                 240

Val Ile Arg Ser Val Asn Phe Thr Asp Asn Ala Lys Thr Ile Ile Val
            245                 250                 255

Gln Leu Asn Thr Ser Val Glu Ile Asn Cys Thr Arg Pro Asn Asn Asn
                260                 265                 270

Thr Arg Lys Arg Ile Arg Ile Gln Arg Gly Pro Gly Arg Ala Phe Val
            275                 280                 285

Thr Ile Gly Lys Ile Gly Asn Met Arg Gln Ala His Cys Asn Ile Ser
            290                 295                 300

Arg Ala Lys Trp Asn Asn Thr Leu Lys Gln Ile Ala Ser Lys Leu Arg
305                 310                 315                 320

Glu Gln Phe Gly Asn Asn Lys Thr Ile Ile Phe Lys Gln Ser Ser Gly
                325                 330                 335

Gly Asp Pro Glu Ile Val Thr His Ser Phe Asn Cys Gly Gly Glu Phe
            340                 345                 350

Phe Tyr Cys Asn Ser Thr Gln Leu Phe Asn Ser Thr Trp Phe Asn Ser
            355                 360                 365

Thr Trp Ser Thr Glu Gly Ser Asn Asn Thr Glu Gly Ser Asp Thr Ile
370                 375                 380

Thr Leu Pro Cys Arg Ile Lys Gln Ile Ile Asn Met Trp Gln Lys Val
385                 390                 395                 400

Gly Lys Ala Met Tyr Ala Pro Pro Ile Ser Gly Gln Ile Arg Cys Ser
                405                 410                 415

Ser Asn Ile Thr Gly Leu Leu Leu Thr Arg Asp Gly Gly Asn Ser Asn
            420                 425                 430

Asn Glu Ser Glu Ile Phe Arg Pro Gly Gly Gly Asp Met Arg Asp Asn
                435                 440                 445

Trp Arg Ser Glu Leu Tyr Lys Tyr Lys Val Val Lys Ile Glu Pro Leu
            450                 455                 460

Gly Val Ala Pro Thr Lys Ala Lys Arg Arg Val Val Gln Arg Glu Lys
465                 470                 475                 480

Arg

<210> SEQ ID NO 2
<211> LENGTH: 511
<212> TYPE: PRT
<213> ORGANISM: Human immunodeficiency virus type 1
<220> FEATURE:
<221> NAME/KEY: misc_feature
<223> OTHER INFORMATION: full-length gp120 from HIV-1 isolate HXBc2

<400> SEQUENCE: 2

Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
                20                  25                  30

Lys Leu Trp Val Thr Val Tyr Tyr Gly Val Pro Val Trp Lys Glu Ala
            35                  40                  45

Thr Thr Thr Leu Phe Cys Ala Ser Asp Ala Lys Ala Tyr Asp Thr Glu
        50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95
```

```
Lys Asn Asp Met Val Glu Gln Met His Glu Asp Ile Ile Ser Leu Trp
                100                 105                 110

Asp Gln Ser Leu Lys Pro Cys Val Lys Leu Thr Pro Leu Cys Val Ser
            115                 120                 125

Leu Lys Cys Thr Asp Leu Lys Asn Asp Thr Asn Thr Asn Ser Ser Ser
        130                 135                 140

Gly Arg Met Ile Met Glu Lys Gly Glu Ile Lys Asn Cys Ser Phe Asn
145                 150                 155                 160

Ile Ser Thr Ser Ile Arg Gly Lys Val Gln Lys Glu Tyr Ala Phe Phe
                165                 170                 175

Tyr Lys Leu Asp Ile Ile Pro Ile Asp Asn Asp Thr Thr Ser Tyr Lys
            180                 185                 190

Leu Thr Ser Cys Asn Thr Ser Val Ile Thr Gln Ala Cys Pro Lys Val
        195                 200                 205

Ser Phe Glu Pro Ile Pro Ile His Tyr Cys Ala Pro Ala Gly Phe Ala
    210                 215                 220

Ile Leu Lys Cys Asn Asn Lys Thr Phe Asn Gly Thr Gly Pro Cys Thr
225                 230                 235                 240

Asn Val Ser Thr Val Gln Cys Thr His Gly Ile Arg Pro Val Val Ser
                245                 250                 255

Thr Gln Leu Leu Leu Asn Gly Ser Leu Ala Glu Glu Val Val Ile
            260                 265                 270

Arg Ser Val Asn Phe Thr Asp Asn Ala Lys Thr Ile Ile Val Gln Leu
        275                 280                 285

Asn Thr Ser Val Glu Ile Asn Cys Thr Arg Pro Asn Asn Thr Arg
    290                 295                 300

Lys Arg Ile Arg Ile Gln Arg Gly Pro Gly Arg Ala Phe Val Thr Ile
305                 310                 315                 320

Gly Lys Ile Gly Asn Met Arg Gln Ala His Cys Asn Ile Ser Arg Ala
                325                 330                 335

Lys Trp Asn Asn Thr Leu Lys Gln Ile Ala Ser Lys Leu Arg Glu Gln
            340                 345                 350

Phe Gly Asn Asn Lys Thr Ile Ile Phe Lys Gln Ser Ser Gly Gly Asp
        355                 360                 365

Pro Glu Ile Val Thr His Ser Phe Asn Cys Gly Gly Glu Phe Phe Tyr
    370                 375                 380

Cys Asn Ser Thr Gln Leu Phe Asn Ser Thr Trp Phe Asn Ser Thr Trp
385                 390                 395                 400

Ser Thr Glu Gly Ser Asn Asn Thr Glu Gly Ser Asp Thr Ile Thr Leu
                405                 410                 415

Pro Cys Arg Ile Lys Gln Ile Ile Asn Met Trp Gln Lys Val Gly Lys
            420                 425                 430

Ala Met Tyr Ala Pro Pro Ile Ser Gly Gln Ile Arg Cys Ser Ser Asn
        435                 440                 445

Ile Thr Gly Leu Leu Leu Thr Arg Asp Gly Gly Asn Ser Asn Asn Glu
    450                 455                 460

Ser Glu Ile Phe Arg Pro Gly Gly Gly Asp Met Arg Asp Asn Trp Arg
465                 470                 475                 480

Ser Glu Leu Tyr Lys Tyr Lys Val Val Lys Ile Glu Pro Leu Gly Val
                485                 490                 495

Ala Pro Thr Lys Ala Lys Arg Arg Val Val Gln Arg Glu Lys Arg
            500                 505                 510
```

<210> SEQ ID NO 3
<211> LENGTH: 253
<212> TYPE: PRT
<213> ORGANISM: Artificial Sequence
<220> FEATURE:
<223> OTHER INFORMATION: ID immunogen A1_V1V2

<400> SEQUENCE: 3

| Val | Pro | Val | Trp | Lys | Asp | Ala | Glu | Thr | Thr | Leu | Phe | Cys | Ala | Ser | Asp |
|---|---|---|---|---|---|---|---|---|---|---|---|---|---|---|---|
| 1 | | | | 5 | | | | | 10 | | | | | 15 | |

| Ala | Lys | Ala | Tyr | Glu | Thr | Glu | Cys | His | Asn | Val | Trp | Ala | Thr | His | Ala |
|---|---|---|---|---|---|---|---|---|---|---|---|---|---|---|---|
| | | | 20 | | | | | 25 | | | | | 30 | | |

| Cys | Val | Pro | Thr | Asp | Pro | Asn | Pro | Gln | Glu | Ile | His | Leu | Glu | Asn | Val |
|---|---|---|---|---|---|---|---|---|---|---|---|---|---|---|---|
| | | | 35 | | | | | 40 | | | | | 45 | | |

| Thr | Glu | Glu | Phe | Asn | Met | Trp | Lys | Asn | Asn | Met | Val | Glu | Gln | Met | His |
|---|---|---|---|---|---|---|---|---|---|---|---|---|---|---|---|
| | 50 | | | | | 55 | | | | | 60 | | | | |

| Thr | Asp | Ile | Ile | Ser | Leu | Trp | Asp | Gln | Cys | Leu | Lys | Pro | Cys | Val | Lys |
|---|---|---|---|---|---|---|---|---|---|---|---|---|---|---|---|
| 65 | | | | | 70 | | | | | 75 | | | | | 80 |

| Leu | Thr | Pro | Leu | Cys | Val | Thr | Leu | Asn | Cys | Ser | Asn | Val | Asn | Val | Thr |
|---|---|---|---|---|---|---|---|---|---|---|---|---|---|---|---|
| | | | | 85 | | | | | 90 | | | | | 95 | |

| Asn | Asn | Thr | Thr | Asn | Thr | His | Glu | Glu | Glu | Ile | Lys | Asn | Cys | Ser | Phe |
|---|---|---|---|---|---|---|---|---|---|---|---|---|---|---|---|
| | | | 100 | | | | | 105 | | | | | 110 | | |

| Asn | Met | Thr | Thr | Glu | Leu | Arg | Asp | Lys | Lys | Gln | Lys | Val | Tyr | Ser | Leu |
|---|---|---|---|---|---|---|---|---|---|---|---|---|---|---|---|
| | | | 115 | | | | | 120 | | | | | 125 | | |

| Phe | Tyr | Arg | Leu | Asp | Val | Val | Gln | Ile | Asn | Glu | Asn | Ser | Asn | Ser |
|---|---|---|---|---|---|---|---|---|---|---|---|---|---|---|
| | | 130 | | | | | 135 | | | | | 140 | | |

| Ser | Tyr | Arg | Leu | Ile | Asn | Cys | Asn | Thr | Ser | Ala | Ile | Thr | Gln | Ala | Cys |
|---|---|---|---|---|---|---|---|---|---|---|---|---|---|---|---|
| 145 | | | | | 150 | | | | | 155 | | | | | 160 |

| Pro | Lys | Val | Ser | Phe | Glu | Pro | Ile | Pro | Ile | His | Tyr | Cys | Ala | Pro | Ala |
|---|---|---|---|---|---|---|---|---|---|---|---|---|---|---|---|
| | | | | 165 | | | | | 170 | | | | | 175 | |

| Gly | Phe | Ala | Ile | Leu | Lys | Cys | Lys | Asp | Lys | Glu | Phe | Asn | Gly | Thr | Gly |
|---|---|---|---|---|---|---|---|---|---|---|---|---|---|---|---|
| | | | 180 | | | | | 185 | | | | | 190 | | |

| Pro | Cys | Lys | Asn | Val | Ser | Thr | Val | Gln | Cys | Thr | His | Gly | Ile | Lys | Pro |
|---|---|---|---|---|---|---|---|---|---|---|---|---|---|---|---|
| | | 195 | | | | | 200 | | | | | 205 | | | |

| Val | Val | Ser | Thr | Gly | Gly | Gly | Asp | Met | Arg | Asp | Asn | Trp | Arg | Ser | Glu |
|---|---|---|---|---|---|---|---|---|---|---|---|---|---|---|---|
| | 210 | | | | | 215 | | | | | 220 | | | | |

| Leu | Tyr | Lys | Tyr | Lys | Val | Val | Lys | Ile | Glu | Pro | Leu | Gly | Val | Ala | Pro |
|---|---|---|---|---|---|---|---|---|---|---|---|---|---|---|---|
| 225 | | | | | 230 | | | | | 235 | | | | | 240 |

| Thr | Arg | Ala | Lys | Arg | Arg | Val | Val | Glu | Arg | Glu | Lys | Arg |
|---|---|---|---|---|---|---|---|---|---|---|---|---|
| | | | | 245 | | | | | 250 | | | |

<210> SEQ ID NO 4
<211> LENGTH: 251
<212> TYPE: PRT
<213> ORGANISM: Artificial Sequence
<220> FEATURE:
<223> OTHER INFORMATION: ID immunogen A2_V1V2

<400> SEQUENCE: 4

| Val | Pro | Val | Trp | Lys | Asp | Ala | Asp | Thr | Thr | Leu | Phe | Cys | Ala | Ser | Asp |
|---|---|---|---|---|---|---|---|---|---|---|---|---|---|---|---|
| 1 | | | | 5 | | | | | 10 | | | | | 15 | |

| Ala | Lys | Ala | Tyr | Asp | Thr | Glu | Cys | His | Asn | Val | Trp | Ala | Thr | His | Ala |
|---|---|---|---|---|---|---|---|---|---|---|---|---|---|---|---|
| | | | 20 | | | | | 25 | | | | | 30 | | |

| Cys | Val | Pro | Thr | Asp | Pro | Asn | Pro | Gln | Glu | Val | Asn | Leu | Glu | Asn | Val |
|---|---|---|---|---|---|---|---|---|---|---|---|---|---|---|---|
| | | | 35 | | | | | 40 | | | | | 45 | | |

| Thr | Glu | Asp | Phe | Asn | Met | Trp | Lys | Asn | Asn | Met | Val | Glu | Gln | Met | His |
|---|---|---|---|---|---|---|---|---|---|---|---|---|---|---|---|
| | 50 | | | | | 55 | | | | | 60 | | | | |

```
Glu Asp Ile Ile Ser Leu Trp Asp Gln Cys Leu Lys Pro Cys Val Lys
 65                  70                  75                  80

Leu Thr Pro Leu Cys Val Thr Leu Asn Cys Ser Asn Ala Asn Thr Thr
                 85                  90                  95

Asn Asn Ser Thr Met Glu Glu Ile Lys Asn Cys Ser Tyr Asn Ile Thr
            100                 105                 110

Thr Glu Leu Arg Asp Lys Thr Gln Lys Val Tyr Ser Leu Phe Tyr Lys
        115                 120                 125

Leu Asp Val Val Gln Leu Asp Glu Ser Asn Lys Ser Glu Tyr Tyr Tyr
    130                 135                 140

Arg Leu Ile Asn Cys Asn Thr Ser Ala Ile Thr Gln Ala Cys Pro Lys
145                 150                 155                 160

Val Ser Phe Glu Pro Ile Pro Ile His Tyr Cys Ala Pro Ala Gly Phe
                165                 170                 175

Ala Ile Leu Lys Cys Lys Asp Pro Arg Phe Asn Gly Thr Gly Ser Cys
            180                 185                 190

Asn Asn Val Ser Ser Val Gln Cys Thr His Gly Ile Lys Pro Val Ala
        195                 200                 205

Ser Thr Gly Gly Gly Asp Met Arg Asp Asn Trp Arg Ser Glu Leu Tyr
    210                 215                 220

Lys Tyr Lys Val Val Lys Ile Glu Pro Leu Gly Val Ala Pro Thr Arg
225                 230                 235                 240

Ala Lys Arg Arg Val Val Glu Arg Glu Lys Arg
                245                 250

<210> SEQ ID NO 5
<211> LENGTH: 255
<212> TYPE: PRT
<213> ORGANISM: Artificial Sequence
<220> FEATURE:
<223> OTHER INFORMATION: ID immunogen B_V1V2

<400> SEQUENCE: 5

Val Pro Val Trp Lys Glu Ala Thr Thr Thr Leu Phe Cys Ala Ser Asp
  1               5                  10                  15

Ala Lys Ala Tyr Asp Thr Glu Cys His Asn Val Trp Ala Thr His Ala
                 20                  25                  30

Cys Val Pro Thr Asp Pro Asn Pro Gln Glu Val Val Leu Glu Asn Val
             35                  40                  45

Thr Glu Asn Phe Asn Met Trp Lys Asn Asn Met Val Glu Gln Met His
         50                  55                  60

Glu Asp Ile Ile Ser Leu Trp Asp Gln Cys Leu Lys Pro Cys Val Lys
 65                  70                  75                  80

Leu Thr Pro Leu Cys Val Thr Leu Asn Cys Thr Asp Leu Met Asn Ala
                 85                  90                  95

Thr Asn Thr Asn Thr Thr Ile Ile Tyr Arg Trp Arg Gly Glu Ile Lys
            100                 105                 110

Asn Cys Ser Phe Asn Ile Thr Thr Ser Ile Arg Asp Lys Val Gln Lys
        115                 120                 125

Glu Tyr Ala Leu Phe Tyr Lys Leu Asp Val Val Pro Ile Asp Asn Asp
    130                 135                 140

Asn Thr Ser Tyr Arg Leu Ile Ser Cys Asn Thr Ser Val Ile Thr Gln
145                 150                 155                 160

Ala Cys Pro Lys Val Ser Phe Glu Pro Ile Pro Ile His Tyr Cys Ala
                165                 170                 175
```

```
Pro Ala Gly Phe Ala Ile Leu Lys Cys Asn Asp Lys Phe Asn Gly
            180                 185                 190

Thr Gly Pro Cys Thr Asn Val Ser Thr Val Gln Cys Thr His Gly Ile
        195                 200                 205

Arg Pro Val Val Ser Thr Gly Gly Asp Met Arg Asp Asn Trp Arg
210                 215                 220

Ser Glu Leu Tyr Lys Tyr Lys Val Val Lys Ile Glu Pro Leu Gly Val
225                 230                 235                 240

Ala Pro Thr Lys Ala Lys Arg Val Gln Arg Glu Lys Arg
                245                 250                 255

<210> SEQ ID NO 6
<211> LENGTH: 246
<212> TYPE: PRT
<213> ORGANISM: Artificial Sequence
<220> FEATURE:
<223> OTHER INFORMATION: ID immunogen C_V1V2

<400> SEQUENCE: 6

Val Pro Val Trp Lys Glu Ala Lys Thr Thr Leu Phe Cys Ala Ser Asp
1               5                   10                  15

Ala Lys Ala Tyr Glu Lys Glu Cys His Asn Val Trp Ala Thr His Ala
            20                  25                  30

Cys Val Pro Thr Asp Pro Asn Pro Gln Glu Ile Val Leu Glu Asn Val
        35                  40                  45

Thr Glu Asn Phe Asn Met Trp Lys Asn Asp Met Val Asp Gln Met His
    50                  55                  60

Glu Asp Ile Ile Ser Leu Trp Asp Gln Cys Leu Lys Pro Cys Val Lys
65                  70                  75                  80

Leu Thr Pro Leu Cys Val Thr Leu Asn Cys Thr Asn Ala Thr Asn Ala
                85                  90                  95

Thr Asn Thr Met Gly Glu Ile Lys Asn Cys Ser Phe Asn Ile Thr Thr
            100                 105                 110

Glu Leu Arg Asp Lys Lys Gln Lys Val Tyr Ala Leu Phe Tyr Arg Leu
        115                 120                 125

Asp Ile Val Pro Leu Asn Glu Asn Asn Ser Tyr Arg Leu Ile Asn Cys
    130                 135                 140

Asn Thr Ser Ala Ile Thr Gln Ala Cys Pro Lys Val Ser Phe Asp Pro
145                 150                 155                 160

Ile Pro Ile His Tyr Cys Ala Pro Ala Gly Tyr Ala Ile Leu Lys Cys
                165                 170                 175

Asn Asn Lys Thr Phe Asn Gly Thr Gly Pro Cys Asn Asn Val Ser Thr
            180                 185                 190

Val Gln Cys Thr His Gly Ile Lys Pro Val Val Ser Thr Gly Gly Gly
        195                 200                 205

Asp Met Arg Asp Asn Trp Arg Ser Glu Leu Tyr Lys Tyr Lys Val Val
    210                 215                 220

Glu Ile Lys Pro Leu Gly Ile Ala Pro Thr Lys Ala Lys Arg Arg Val
225                 230                 235                 240

Val Glu Arg Glu Lys Arg
                245

<210> SEQ ID NO 7
<211> LENGTH: 253
<212> TYPE: PRT
<213> ORGANISM: Artificial Sequence
```

```
<220> FEATURE:
<223> OTHER INFORMATION: ID immunogen D_V1V2

<400> SEQUENCE: 7

Val Pro Val Trp Lys Glu Ala Thr Thr Thr Leu Phe Cys Ala Ser Asp
1               5                   10                  15

Ala Lys Ser Tyr Lys Thr Glu Cys His Asn Ile Trp Ala Thr His Ala
            20                  25                  30

Cys Val Pro Thr Asp Pro Asn Pro Gln Glu Ile Glu Leu Glu Asn Val
        35                  40                  45

Thr Glu Asn Phe Asn Met Trp Lys Asn Asn Met Val Glu Gln Met His
    50                  55                  60

Glu Asp Ile Ile Ser Leu Trp Asp Gln Cys Leu Lys Pro Cys Val Lys
65                  70                  75                  80

Leu Thr Pro Leu Cys Val Thr Leu Asn Cys Thr Asp Val Lys Arg Asn
                85                  90                  95

Asn Thr Ser Asn Asp Thr Asn Glu Gly Glu Met Lys Asn Cys Ser Phe
            100                 105                 110

Asn Ile Thr Thr Glu Ile Arg Asp Lys Lys Lys Gln Val His Ala Leu
        115                 120                 125

Phe Tyr Lys Leu Asp Val Val Pro Ile Asp Asn Asn Ser Asn Thr
    130                 135                 140

Ser Tyr Arg Leu Ile Asn Cys Asn Thr Ser Ala Ile Thr Gln Ala Cys
145                 150                 155                 160

Pro Lys Val Thr Phe Glu Pro Ile Pro Ile His Tyr Cys Ala Pro Ala
                165                 170                 175

Gly Phe Ala Ile Leu Lys Cys Lys Asp Lys Lys Phe Asn Gly Thr Gly
            180                 185                 190

Pro Cys Lys Asn Val Ser Thr Val Gln Cys Thr His Gly Ile Arg Pro
        195                 200                 205

Val Val Ser Thr Gly Gly Gly Asp Met Arg Asp Asn Trp Arg Ser Glu
    210                 215                 220

Leu Tyr Lys Tyr Lys Val Val Lys Ile Glu Pro Leu Gly Val Ala Pro
225                 230                 235                 240

Thr Arg Ala Lys Arg Arg Val Val Glu Arg Glu Lys Arg
                245                 250

<210> SEQ ID NO 8
<211> LENGTH: 252
<212> TYPE: PRT
<213> ORGANISM: Artificial Sequence
<220> FEATURE:
<223> OTHER INFORMATION: ID immunogen F1_V1V2

<400> SEQUENCE: 8

Val Pro Val Trp Lys Glu Ala Thr Thr Thr Leu Phe Cys Ala Ser Asp
1               5                   10                  15

Ala Lys Ser Tyr Glu Lys Glu Cys His Asn Val Trp Ala Thr His Ala
            20                  25                  30

Cys Val Pro Thr Asp Pro Asn Pro Gln Glu Val Val Leu Glu Asn Val
        35                  40                  45

Thr Glu Asn Phe Asp Met Trp Lys Asn Asn Met Val Glu Gln Met His
    50                  55                  60

Thr Asp Ile Ile Ser Leu Trp Asp Gln Cys Leu Lys Pro Cys Val Lys
65                  70                  75                  80

Leu Thr Pro Leu Cys Val Thr Leu Asn Cys Thr Asp Val Asn Ala Thr
```

```
                85                  90                  95
Asn Asn Asp Thr Asn Asp Asn Lys Thr Gly Ala Ile Gln Asn Cys Ser
                100                 105                 110

Phe Asn Met Thr Thr Glu Val Arg Asp Lys Lys Leu Lys Val His Ala
            115                 120                 125

Leu Phe Tyr Lys Leu Asp Ile Val Pro Ile Ser Asn Asn Asn Ser Lys
130                 135                 140

Tyr Arg Leu Ile Asn Cys Asn Thr Ser Thr Ile Thr Gln Ala Cys Pro
145                 150                 155                 160

Lys Val Ser Trp Asp Pro Ile Pro Ile His Tyr Cys Ala Pro Ala Gly
                165                 170                 175

Tyr Ala Ile Leu Lys Cys Asn Asp Lys Arg Phe Asn Gly Thr Gly Pro
                180                 185                 190

Cys Lys Asn Val Ser Thr Val Gln Cys Thr His Gly Ile Lys Pro Val
                195                 200                 205

Val Ser Thr Gly Gly Gly Asn Met Lys Asp Asn Trp Arg Ser Glu Leu
210                 215                 220

Tyr Lys Tyr Lys Val Val Glu Ile Glu Pro Leu Gly Val Ala Pro Thr
225                 230                 235                 240

Lys Ala Lys Arg Gln Val Val Lys Arg Glu Arg Arg
                245                 250

<210> SEQ ID NO 9
<211> LENGTH: 250
<212> TYPE: PRT
<213> ORGANISM: Artificial Sequence
<220> FEATURE:
<223> OTHER INFORMATION: ID immunogen F2_V1V2

<400> SEQUENCE: 9

Val Pro Val Trp Lys Glu Ala Thr Thr Thr Leu Phe Cys Ala Ser Asp
1               5                   10                  15

Ala Lys Ala Tyr Glu Arg Glu Cys His Asn Val Trp Ala Thr Tyr Ala
                20                  25                  30

Cys Val Pro Thr Asp Pro Ser Pro Gln Glu Leu Val Leu Gly Asn Val
            35                  40                  45

Thr Glu Asn Phe Asn Met Trp Lys Asn Asn Met Val Asp Gln Met His
    50                  55                  60

Glu Asp Ile Ile Ser Leu Trp Asp Gln Cys Leu Lys Pro Cys Val Lys
65                  70                  75                  80

Leu Thr Pro Leu Cys Val Thr Leu Asn Cys Thr Asp Val Asn Val Thr
                85                  90                  95

Ile Asn Thr Thr Asn Val Thr Leu Gly Glu Ile Lys Asn Cys Ser Phe
                100                 105                 110

Asn Ile Thr Thr Glu Ile Lys Asp Lys Lys Lys Glu Tyr Ala Leu
            115                 120                 125

Phe Tyr Arg Leu Asp Val Val Pro Ile Asn Asn Ser Ile Val Tyr Arg
130                 135                 140

Leu Ile Ser Cys Asn Thr Ser Thr Val Thr Gln Ala Cys Pro Lys Val
145                 150                 155                 160

Ser Phe Glu Pro Ile Pro Ile His Tyr Cys Ala Pro Ala Gly Phe Ala
                165                 170                 175

Ile Leu Lys Cys Asn Asp Lys Lys Phe Asn Gly Thr Gly Leu Cys Arg
                180                 185                 190

Asn Val Ser Thr Val Gln Cys Thr His Gly Ile Arg Pro Val Val Ser
```

```
                    195                 200                 205

Thr Gly Gly Gly Asp Met Arg Asp Asn Trp Arg Ser Glu Leu Tyr Lys
    210                 215                 220

Tyr Lys Val Val Lys Ile Glu Pro Leu Gly Val Ala Pro Thr Lys Ala
225                 230                 235                 240

Lys Arg Gln Val Val Gln Arg Glu Lys Arg
                245                 250

<210> SEQ ID NO 10
<211> LENGTH: 253
<212> TYPE: PRT
<213> ORGANISM: Artificial Sequence
<220> FEATURE:
<223> OTHER INFORMATION: ID immunogen G_V1V2

<400> SEQUENCE: 10

Val Pro Val Trp Glu Asp Ala Asp Thr Thr Leu Phe Cys Ala Ser Asp
1               5                   10                  15

Ala Lys Ala Tyr Ser Thr Glu Cys His Asn Val Trp Ala Thr His Ala
            20                  25                  30

Cys Val Pro Thr Asp Pro Asn Pro Gln Glu Ile Thr Leu Glu Asn Val
        35                  40                  45

Thr Glu Asn Phe Asn Met Trp Lys Asn Asn Met Val Glu Gln Met His
    50                  55                  60

Glu Asp Ile Ile Ser Leu Trp Asp Glu Cys Leu Lys Pro Cys Val Lys
65                  70                  75                  80

Leu Thr Pro Leu Cys Val Thr Leu Asn Cys Thr Asp Val Asn Val Thr
                85                  90                  95

Asn Asn Asn Thr Asn Asn Thr Lys Lys Glu Ile Lys Asn Cys Ser Phe
            100                 105                 110

Asn Ile Thr Thr Glu Ile Arg Asp Lys Lys Lys Glu Tyr Ala Leu
        115                 120                 125

Phe Tyr Arg Leu Asp Val Val Pro Ile Asn Asp Asn Gly Asn Ser Ser
    130                 135                 140

Ile Tyr Arg Leu Ile Asn Cys Asn Val Ser Thr Ile Lys Gln Ala Cys
145                 150                 155                 160

Pro Lys Val Thr Phe Asp Pro Ile Pro Ile His Tyr Cys Ala Pro Ala
                165                 170                 175

Gly Phe Ala Ile Leu Lys Cys Arg Asp Lys Lys Phe Asn Gly Thr Gly
            180                 185                 190

Pro Cys Lys Asn Val Ser Thr Val Gln Cys Thr His Gly Ile Lys Pro
        195                 200                 205

Val Val Ser Thr Gly Gly Asp Met Arg Asp Asn Trp Arg Ser Glu
    210                 215                 220

Leu Tyr Lys Tyr Lys Ile Val Lys Ile Lys Pro Leu Gly Val Ala Pro
225                 230                 235                 240

Thr Arg Ala Arg Arg Arg Val Val Glu Arg Glu Lys Arg
                245                 250

<210> SEQ ID NO 11
<211> LENGTH: 254
<212> TYPE: PRT
<213> ORGANISM: Artificial Sequence
<220> FEATURE:
<223> OTHER INFORMATION: ID immunogen H_V1V2

<400> SEQUENCE: 11
```

Val Pro Val Trp Lys Glu Ala Lys Thr Thr Leu Phe Cys Ala Ser Asp
1               5                   10                  15

Ala Lys Ala Tyr Glu Thr Glu Cys His Asn Val Trp Ala Thr His Ala
            20                  25                  30

Cys Val Pro Thr Asp Pro Asn Pro Gln Glu Met Val Leu Glu Asn Val
        35                  40                  45

Thr Glu Asn Phe Asn Met Trp Glu Asn Asp Met Val Glu Gln Met His
    50                  55                  60

Thr Asp Ile Ile Ser Leu Trp Asp Gln Cys Leu Lys Pro Cys Val Lys
65                  70                  75                  80

Leu Thr Pro Leu Cys Val Thr Leu Asp Cys Ser Asn Val Asn Thr Thr
                85                  90                  95

Asn Ala Thr Asn Ser Arg Phe Asn Met Gln Glu Glu Leu Thr Asn Cys
            100                 105                 110

Ser Phe Asn Val Thr Thr Val Ile Arg Asp Lys Gln Gln Lys Val His
        115                 120                 125

Ala Leu Phe Tyr Arg Leu Asp Val Val Pro Ile Asp Asp Asn Asn Ser
    130                 135                 140

Tyr Gln Tyr Arg Leu Ile Asn Cys Asn Thr Ser Val Ile Thr Gln Ala
145                 150                 155                 160

Cys Pro Lys Val Ser Phe Glu Pro Ile Pro Ile His Tyr Cys Ala Pro
                165                 170                 175

Ala Gly Phe Ala Ile Leu Lys Cys Asn Asn Lys Thr Phe Asn Gly Thr
            180                 185                 190

Gly Pro Cys Thr Asn Val Ser Thr Val Gln Cys Thr His Gly Ile Arg
        195                 200                 205

Pro Val Val Ser Thr Gly Gly Gly Asp Met Arg Asp Asn Trp Arg Ser
    210                 215                 220

Glu Leu Tyr Lys Tyr Lys Val Val Lys Ile Glu Pro Leu Gly Val Ala
225                 230                 235                 240

Pro Thr Glu Ala Arg Arg Arg Val Val Glu Arg Glu Lys Arg
                245                 250

<210> SEQ ID NO 12
<211> LENGTH: 258
<212> TYPE: PRT
<213> ORGANISM: Artificial Sequence
<220> FEATURE:
<223> OTHER INFORMATION: ID immunogen 01_AE_V1V2

<400> SEQUENCE: 12

Val Pro Val Trp Arg Asp Ala Asp Thr Thr Leu Phe Cys Ala Ser Asp
1               5                   10                  15

Ala Lys Ala His Glu Thr Glu Cys His Asn Val Trp Ala Thr His Ala
            20                  25                  30

Cys Val Pro Thr Asp Pro Asn Pro Gln Glu Ile His Leu Glu Asn Val
        35                  40                  45

Thr Glu Asn Phe Asn Met Trp Lys Asn Asn Met Val Glu Gln Met Gln
    50                  55                  60

Glu Asp Val Ile Ser Leu Trp Asp Gln Cys Leu Lys Pro Cys Val Lys
65                  70                  75                  80

Leu Thr Pro Leu Cys Val Thr Leu Asn Cys Thr Asn Ala Asn Leu Thr
                85                  90                  95

Asn Val Asn Asn Ile Thr Asn Val Ser Asn Ile Ile Gly Asn Ile Thr
            100                 105                 110

```
Asn Glu Val Arg Asn Cys Ser Phe Asn Met Thr Thr Glu Leu Arg Asp
            115                 120                 125

Lys Lys Gln Lys Val His Ala Leu Phe Tyr Lys Leu Asp Ile Val Gln
        130                 135                 140

Ile Glu Asp Asn Asn Ser Tyr Arg Leu Ile Asn Cys Asn Thr Ser Val
145                 150                 155                 160

Ile Lys Gln Ala Cys Pro Lys Ile Ser Phe Asp Pro Ile Pro Ile His
                165                 170                 175

Tyr Cys Thr Pro Ala Gly Tyr Ala Ile Leu Lys Cys Asn Asp Lys Asn
            180                 185                 190

Phe Asn Gly Thr Gly Pro Cys Lys Asn Val Ser Ser Val Gln Cys Thr
        195                 200                 205

His Gly Ile Lys Pro Val Val Ser Thr Gly Gly Asn Ile Lys Asp
            210                 215                 220

Asn Trp Arg Ser Glu Leu Tyr Lys Tyr Lys Val Val Gln Ile Glu Pro
225                 230                 235                 240

Leu Gly Ile Ala Pro Thr Arg Ala Lys Arg Val Val Glu Arg Glu
                245                 250                 255

Lys Arg

<210> SEQ ID NO 13
<211> LENGTH: 251
<212> TYPE: PRT
<213> ORGANISM: Artificial Sequence
<220> FEATURE:
<223> OTHER INFORMATION: ID immunogen 02_AG_V1V2

<400> SEQUENCE: 13

Val Pro Val Trp Arg Asp Ala Glu Thr Thr Leu Phe Cys Ala Ser Asp
1               5                   10                  15

Ala Lys Ala Tyr Asp Thr Glu Cys His Asn Val Trp Ala Thr His Ala
                20                  25                  30

Cys Val Pro Thr Asp Pro Asn Pro Gln Glu Ile His Leu Glu Asn Val
            35                  40                  45

Thr Glu Asn Phe Asn Met Trp Lys Asn Met Val Glu Gln Met His
        50                  55                  60

Glu Asp Ile Ile Ser Leu Trp Asp Gln Cys Leu Lys Pro Cys Val Lys
65                  70                  75                  80

Leu Thr Pro Leu Cys Val Thr Leu Asp Cys His Asn Asn Ile Thr Asn
                85                  90                  95

Ser Asn Thr Thr Asn Asn Asn Ala Gly Glu Ile Lys Asn Cys Ser Phe
            100                 105                 110

Asn Met Thr Thr Glu Leu Arg Asp Lys Lys Gln Lys Val Tyr Ala Leu
        115                 120                 125

Phe Tyr Arg Leu Asp Val Val Gln Ile Asn Lys Asn Asn Ser Gln Tyr
    130                 135                 140

Arg Leu Ile Asn Cys Asn Thr Ser Ala Ile Thr Gln Ala Cys Pro Lys
145                 150                 155                 160

Val Ser Phe Glu Pro Ile Pro Ile His Tyr Cys Ala Pro Ala Gly Phe
                165                 170                 175

Ala Ile Leu Lys Cys Asn Asp Lys Glu Phe Asn Gly Thr Gly Pro Cys
            180                 185                 190

Lys Asn Val Ser Thr Val Gln Cys Thr His Gly Ile Lys Pro Val Val
        195                 200                 205

Ser Thr Gly Gly Gly Asp Met Arg Asp Asn Trp Arg Ser Glu Leu Tyr
```

```
            210                 215                 220
Lys Tyr Lys Val Val Lys Ile Glu Pro Leu Gly Val Ala Pro Thr Arg
225                 230                 235                 240

Ala Lys Arg Arg Val Val Glu Arg Glu Lys Arg
                245                 250
```

```
<210> SEQ ID NO 14
<211> LENGTH: 252
<212> TYPE: PRT
<213> ORGANISM: Artificial Sequence
<220> FEATURE:
<223> OTHER INFORMATION: ID immunogen 03_AB_V1V2

<400> SEQUENCE: 14

Val Pro Val Trp Lys Glu Ala Thr Thr Thr Leu Phe Cys Ala Ser Asp
1               5                   10                  15

Ala Lys Ala Tyr Ser Lys Glu Cys His Asn Val Trp Ala Thr Tyr Ala
                20                  25                  30

Cys Val Pro Thr Asp Pro Ser Pro Gln Glu Ile Pro Leu Glu Asn Val
            35                  40                  45

Thr Glu Asn Phe Asn Met Gly Lys Asn Asn Met Val Glu Gln Met His
50                  55                  60

Glu Asp Ile Ile Ser Leu Trp Asp Gln Cys Leu Lys Pro Cys Val Lys
65                  70                  75                  80

Leu Thr Pro Leu Cys Val Thr Leu Asn Cys Thr Asp Leu Lys Lys Asn
                85                  90                  95

Val Thr Ser Thr Asn Thr Ser Ser Ile Lys Met Met Glu Met Lys Asn
            100                 105                 110

Cys Ser Phe Asn Ile Thr Thr Asp Leu Arg Asp Lys Val Lys Lys Glu
        115                 120                 125

Tyr Ala Leu Phe Tyr Lys Leu Asp Val Val Gln Ile Asp Asn Asp Ser
    130                 135                 140

Tyr Arg Leu Ile Ser Cys Asn Thr Ser Val Val Thr Gln Ala Cys Pro
145                 150                 155                 160

Lys Ile Ser Phe Glu Pro Ile Pro Ile His Tyr Cys Ala Pro Ala Gly
                165                 170                 175

Phe Ala Ile Leu Lys Cys Asn Asp Lys Lys Phe Asn Gly Thr Gly Pro
            180                 185                 190

Cys Thr Asn Val Ser Thr Val Gln Cys Thr His Gly Ile Lys Pro Val
        195                 200                 205

Val Ser Thr Gly Gly Gly Asp Met Arg Asp Asn Trp Arg Ser Glu Leu
    210                 215                 220

Tyr Lys Tyr Lys Val Val Lys Ile Glu Pro Leu Gly Val Ala Pro Thr
225                 230                 235                 240

Lys Ala Lys Arg Arg Val Val Gln Arg Glu Lys Arg
                245                 250
```

```
<210> SEQ ID NO 15
<211> LENGTH: 257
<212> TYPE: PRT
<213> ORGANISM: Artificial Sequence
<220> FEATURE:
<223> OTHER INFORMATION: ID immunogen 04_CPX_V1V2

<400> SEQUENCE: 15

Val Pro Val Trp Arg Asp Ala Glu Thr Thr Pro Phe Cys Ala Ser Asp
1               5                   10                  15
```

Ala Lys Ala Tyr Asp Lys Glu Cys His Asn Ile Trp Ala Thr His Ala
            20                  25                  30

Cys Val Pro Thr Asp Pro Asn Pro Gln Glu Ile Ala Leu Lys Asn Val
            35                  40                  45

Thr Glu Asn Phe Asn Met Trp Lys Asn Asn Met Val Glu Gln Met His
        50                  55                  60

Glu Asp Ile Ile Ser Leu Trp Asp Glu Cys Leu Lys Pro Cys Val Lys
65                  70                  75                  80

Leu Thr Pro Leu Cys Val Ala Leu Asn Cys Ser Asn Ala Thr Ile Asn
                85                  90                  95

Asn Ser Thr Lys Thr Asn Ser Thr Glu Glu Ile Lys Asn Cys Ser Phe
            100                 105                 110

Asn Ile Thr Thr Glu Ile Arg Asp Lys Lys Lys Glu Tyr Ala Leu
            115                 120                 125

Phe Tyr Arg Leu Asp Ile Val Pro Ile Asn Asp Ser Ala Asn Asn Asn
130                 135                 140

Ser Ile Asn Ser Glu Tyr Met Leu Ile Asn Cys Asn Ala Ser Thr Ile
145                 150                 155                 160

Lys Gln Ala Cys Pro Lys Val Thr Phe Glu Pro Ile Pro Ile His Tyr
                165                 170                 175

Cys Ala Pro Ala Gly Phe Ala Ile Leu Lys Cys Asn Asp Lys Asn Phe
            180                 185                 190

Thr Gly Leu Gly Pro Cys Thr Asn Val Ser Ser Val Gln Cys Thr His
        195                 200                 205

Gly Ile Lys Pro Val Val Ser Thr Gly Gly Asp Met Arg Asp Asn
    210                 215                 220

Trp Arg Ser Glu Leu Tyr Lys Tyr Lys Val Val Lys Ile Glu Pro Val
225                 230                 235                 240

Gly Val Ala Pro Thr Arg Ala Arg Arg Val Val Gln Arg Glu Lys
                245                 250                 255

Arg

<210> SEQ ID NO 16
<211> LENGTH: 251
<212> TYPE: PRT
<213> ORGANISM: Artificial Sequence
<220> FEATURE:
<223> OTHER INFORMATION: ID immunogen 06_CPX_V1V2

<400> SEQUENCE: 16

Val Pro Ala Trp Glu Asp Ala Asp Thr Ile Leu Phe Cys Ala Ser Asp
1               5                   10                  15

Ala Lys Ala Tyr Ser Ala Glu Cys His Asn Val Trp Ala Thr His Ala
            20                  25                  30

Cys Val Pro Thr Asp Pro Asn Pro Gln Glu Ile Ala Leu Glu Asn Val
            35                  40                  45

Thr Glu Asn Phe Asn Met Trp Lys Asn His Met Val Glu Gln Met His
        50                  55                  60

Glu Asp Ile Ile Ser Leu Trp Asp Glu Cys Leu Lys Pro Cys Val Lys
65                  70                  75                  80

Leu Thr Pro Leu Cys Val Thr Leu Asn Cys Thr Asn Val Thr Lys Asn
                85                  90                  95

Asn Asn Thr Lys Ile Met Gly Arg Glu Glu Ile Lys Asn Cys Ser Phe
            100                 105                 110

Asn Val Thr Thr Glu Ile Arg Asp Lys Lys Lys Lys Glu Tyr Ala Leu

```
                    115                 120                 125
Phe Tyr Arg Leu Asp Val Val Pro Ile Asp Asn Asn Ser Tyr
                130

```
                     225                 230                 235                 240

Glu Ile Lys Pro Leu Gly Val Ala Pro Thr Ala Ala Lys Arg Arg Val
                245                 250                 255

Val Glu Arg Glu Lys Arg
            260

<210> SEQ ID NO 18
<211> LENGTH: 251
<212> TYPE: PRT
<213> ORGANISM: Artificial Sequence
<220> FEATURE:
<223> OTHER INFORMATION: ID immunogen 10_CD_V1V2

<400> SEQUENCE: 18

Val Pro Val Trp Lys Glu Thr Thr Thr Leu Phe Cys Ala Ser Asp
1               5                   10                  15

Ala Lys Ala Tyr Lys Ala Glu Cys His Asn Ile Trp Ala Thr His Ala
                20                  25                  30

Cys Val Pro Thr Asp Pro Asn Pro Gln Glu Ile Val Leu Glu Asn Val
            35                  40                  45

Thr Glu Asn Phe Asn Met Trp Lys Asn Gly Met Val Asp Gln Met His
    50                  55                  60

Glu Asp Ile Ile Ser Leu Trp Asp Gln Cys Leu Lys Pro Cys Val Lys
65                  70                  75                  80

Leu Thr Pro Leu Cys Val Thr Leu Asn Cys Ser Asp Val Asn Ala Thr
                85                  90                  95

Asn Ser Ala Thr Asn Thr Val Val Ala Gly Met Lys Asn Cys Ser Phe
            100                 105                 110

Asn Ile Thr Thr Glu Ile Arg Asp Lys Lys Gln Glu Tyr Ala Leu
        115                 120                 125

Phe Tyr Lys Leu Asp Val Val Gln Ile Asp Gly Ser Asn Thr Ser Tyr
    130                 135                 140

Arg Leu Ile Asn Cys Asn Thr Ser Ala Ile Thr Gln Ala Cys Pro Lys
145                 150                 155                 160

Val Thr Phe Glu Pro Ile Pro Ile His Tyr Cys Ala Pro Ala Gly Phe
                165                 170                 175

Ala Ile Leu Lys Cys Asn Asp Lys Lys Phe Asn Gly Thr Gly Pro Cys
            180                 185                 190

Lys Asn Val Ser Thr Val Gln Cys Thr His Gly Ile Lys Pro Val Val
        195                 200                 205

Ser Thr Gly Gly Gly Asp Met Arg Asp Asn Trp Arg Ser Glu Leu Tyr
    210                 215                 220

Lys Tyr Lys Val Val Lys Ile Glu Pro Leu Gly Leu Ala Pro Thr Lys
225                 230                 235                 240

Ala Lys Arg Arg Val Val Glu Arg Glu Lys Arg
                245                 250

<210> SEQ ID NO 19
<211> LENGTH: 251
<212> TYPE: PRT
<213> ORGANISM: Artificial Sequence
<220> FEATURE:
<223> OTHER INFORMATION: ID immunogen 11_CPX_V1V2

<400> SEQUENCE: 19

Val Pro Val Trp Lys Asp Ala Asp Thr Thr Leu Phe Cys Ala Ser Asp
1               5                   10                  15
```

```
Ala Lys Ala Tyr Ser Thr Glu Cys His Asn Val Trp Ala Thr His Ala
             20                  25                  30

Cys Val

```
Val Gln Ala Leu Phe Tyr Arg Leu Asp Ile Val Pro Ile Ser Asp Asn
            130                 135                 140

Asn Ser Asn Glu Tyr Arg Leu Ile Asn Cys Asn Thr Ser Thr Ile Thr
145                 150                 155                 160

Gln Ala Cys Pro Lys Val Ser Trp Asp Pro Ile Pro Ile His Tyr Cys
                165                 170                 175

Ala Pro Ala Gly Tyr Ala Ile Leu Lys Cys Asn Asp Lys Lys Phe Asn
                180                 185                 190

Gly Thr Gly Pro Cys Lys Asn Val Ser Thr Val Gln Cys Thr His Gly
            195                 200                 205

Ile Lys Pro Val Val Ser Thr Gly Gly Gly Asn Met Lys Asp Asn Trp
210                 215                 220

Arg Ser Glu Leu Tyr Lys Tyr Lys Val Val Glu Ile Glu Pro Leu Gly
225                 230                 235                 240

Val Ala Pro Thr Arg Ala Lys Arg Gln Val Val Lys Arg Glu Lys Arg
                245                 250                 255
```

<210> SEQ ID NO 21
<211> LENGTH: 255
<212> TYPE: PRT
<213> ORGANISM: Artificial Sequence
<220> FEATURE:
<223> OTHER INFORMATION: ID immunogen 14_BG_V1V2

<400> SEQUENCE: 21

```
Val Pro Val Trp Lys Glu Ala Thr Thr Thr Leu Phe Cys Ala Ser Asp
1               5                   10                  15

Ala Lys Ala Tyr Asp Ala Glu Cys His Asn Val Trp Ala Thr His Ala
                20                  25                  30

Cys Val Pro Thr Asp Pro Asn Pro Gln Glu Val Ala Leu Glu Asn Val
                35                  40                  45

Thr Glu Asn Phe Asn Met Trp Glu Asn Asn Met Val Asp Gln Met Gln
        50                  55                  60

Glu Asp Ile Ile Ser Leu Trp Asp Gln Cys Leu Lys Pro Cys Val Glu
65                  70                  75                  80

Leu Thr Pro Leu Cys Val Thr Leu Asn Cys Thr Asp Phe Asn Asn Thr
                85                  90                  95

Thr Asn Asn Thr Thr Asn Thr Arg Asn Asp Gly Glu Gly Glu Ile Lys
            100                 105                 110

Asn Cys Ser Phe Asn Ile Thr Ser Leu Arg Asp Lys Ile Lys Lys
        115                 120                 125

Glu Tyr Ala Leu Phe Tyr Asn Leu Asp Val Val Gln Met Asp Asn Asp
        130                 135                 140

Asn Ser Ser Tyr Arg Leu Thr Ser Cys Asn Thr Ser Ile Ile Thr Gln
145                 150                 155                 160

Ala Cys Pro Lys Val Ser Phe Thr Pro Ile Pro Ile His Tyr Cys Ala
                165                 170                 175

Pro Ala Gly Phe Val Ile Leu Lys Cys Asn Asn Lys Thr Phe Asn Gly
                180                 185                 190

Thr Gly Pro Cys Thr Asn Val Ser Thr Val Gln Cys Thr His Gly Ile
            195                 200                 205

Arg Pro Val Val Ser Thr Gly Gly Gly Asn Met Lys Asp Asn Trp Arg
        210                 215                 220

Ser Glu Leu Tyr Lys Tyr Lys Val Val Lys Ile Glu Pro Leu Gly Val
225                 230                 235                 240
```

```
Ala Pro Thr Arg Ala Lys Arg Arg Val Val Gln Arg Glu Lys Arg
                245                 250                 255

<210> SEQ ID NO 22
<211> LENGTH: 248
<212> TYPE: PRT
<213> ORGANISM: Artificial Sequence
<220> FEATURE:
<223> OTHER INFORMATION: ID immunogen CON_OF_CONS_V1V2

<400> SEQUENCE: 22

Val Pro Val Trp Lys Glu Ala Asn Thr Thr Leu Phe Cys Ala Ser Asp
1               5                   10                  15

Ala Lys Ala Tyr Asp Thr Glu Cys His Asn Val Trp Ala Thr His Ala
            20                  25                  30

Cys Val Pro Thr Asp Pro Asn Pro Gln Glu Ile Val Leu Glu Asn Val
        35                  40                  45

Thr Glu Asn Phe Asn Met Trp Lys Asn Asn Met Val Glu Gln Met His
    50                  55                  60

Glu Asp Ile Ile Ser Leu Trp Asp Gln Cys Leu Lys Pro Cys Val Lys
65                  70                  75                  80

Leu Thr Pro Leu Cys Val Thr Leu Asn Cys Thr Asp Val Asn Ala Thr
                85                  90                  95

Asn Asn Thr Thr Asn Asn Glu Glu Ile Lys Asn Cys Ser Phe Asn Ile
            100                 105                 110

Thr Thr Glu Ile Arg Asp Lys Lys Lys Val Tyr Ala Leu Phe Tyr
        115                 120                 125

Lys Leu Asp Val Val Pro Ile Asp Asp Asn Asn Ser Tyr Arg Leu Ile
    130                 135                 140

Asn Cys Asn Thr Ser Ala Ile Thr Gln Ala Cys Pro Lys Val Ser Phe
145                 150                 155                 160

Glu Pro Ile Pro Ile His Tyr Cys Ala Pro Ala Gly Phe Ala Ile Leu
                165                 170                 175

Lys Cys Asn Asp Lys Lys Phe Asn Gly Thr Gly Pro Cys Lys Asn Val
            180                 185                 190

Ser Thr Val Gln Cys Thr His Gly Ile Lys Pro Val Val Ser Thr Gly
        195                 200                 205

Gly Gly Asp Met Arg Asp Asn Trp Arg Ser Glu Leu Tyr Lys Tyr Lys
    210                 215                 220

Val Val Lys Ile Glu Pro Leu Gly Val Ala Pro Thr Lys Ala Lys Arg
225                 230                 235                 240

Arg Val Val Glu Arg Glu Lys Arg
                245

<210> SEQ ID NO 23
<211> LENGTH: 266
<212> TYPE: PRT
<213> ORGANISM: Artificial Sequence
<220> FEATURE:
<223> OTHER INFORMATION: ID immunogen AB097872_V1V2

<400> SEQUENCE: 23

Val Pro Val Trp Arg Asp Ala Glu Thr Thr Leu Phe Cys Ala Ser Asp
1               5                   10                  15

Ala Lys Ala His Val Gly Glu Cys His Asn Val Trp Ala Thr His Ala
            20                  25                  30

Cys Val Pro Thr Asp Pro Asn Pro Gln Glu Ile His Leu Glu Asn Val
        35                  40                  45
```

Thr Glu Asn Phe Asn Met Trp Lys Asn Lys Met Ala Asp Gln Met Gln
            50                  55                  60

Glu Asp Val Ile Ser Leu Trp Asp Gln Cys Leu Lys Pro Cys Val Lys
 65                  70                  75                  80

Leu Thr Pro Leu Cys Val Thr Leu Asn Cys Thr Asp Ala Gln Val Asn
                    85                  90                  95

Gln Thr Trp Asn Asn Val Thr Lys Ala Asp Asn Ile Thr Asn Leu Glu
                100                 105                 110

Asn Ile Thr Asn Glu Val Lys Asn Cys Ser Phe Asn Met Thr Thr Glu
            115                 120                 125

Ile Arg Asp Lys Gln Gln Arg Val Gln Ala Leu Phe Tyr Lys Leu Asp
130                 135                 140

Ile Val Pro Ile Gly Asn Asn Asn Lys Thr Ser Gly Glu Tyr Arg
145                 150                 155                 160

Leu Ile Asn Cys Asn Thr Ser Val Ile Lys Gln Ala Cys Pro Lys Val
                165                 170                 175

Ser Phe Asp Pro Ile Pro Ile His Tyr Cys Thr Pro Ala Gly Phe Ala
                180                 185                 190

Ile Leu Lys Cys Asn Asp Lys Lys Phe Asn Gly Thr Gly Pro Cys Lys
            195                 200                 205

Asn Val Ser Ser Val Gln Cys Thr His Gly Ile Lys Pro Val Val Ser
210                 215                 220

Thr Gly Gly Gly Asn Ile Lys Asp Asn Trp Arg Ser Glu Leu Tyr Lys
225                 230                 235                 240

Tyr Lys Val Val Glu Ile Glu Pro Leu Gly Ile Ala Pro Thr Arg Ala
                245                 250                 255

Lys Arg Arg Val Val Glu Arg Gln Lys Arg
                260                 265

<210> SEQ ID NO 24
<211> LENGTH: 257
<212> TYPE: PRT
<213> ORGANISM: Artificial Sequence
<220> FEATURE:
<223> OTHER INFORMATION: ID immunogen AB052867_V1V2

<400> SEQUENCE: 24

Val Pro Val Trp Lys Asp Ala Glu Thr Thr Leu Phe Cys Ala Ser Asp
 1                   5                  10                  15

Ala Lys Ala Tyr Asp Ala Glu Cys His Asn Val Trp Ala Thr His Ala
                 20                  25                  30

Cys Val Pro Thr Asp Pro Asn Pro Gln Glu Ile Ser Leu Glu Asn Val
             35                  40                  45

Thr Glu Asp Phe Asn Met Trp Lys Asn Lys Met Val Glu Gln Met His
        50                   55                  60

Val Asp Ile Ile Ser Leu Trp Asp Gln Cys Leu Lys Pro Cys Val Lys
 65                  70                  75                  80

Leu Thr Pro Leu Cys Val Thr Leu Asp Cys His Asp Asn Ile Thr Thr
                 85                  90                  95

Ser Gly Asn Arg Asn Ile Ser Val Glu Met Lys Gly Glu Ile Lys Asn
                100                 105                 110

Cys Ser Phe Asn Met Thr Thr Val Leu Arg Asp Lys Lys Glu Lys Val
            115                 120                 125

Thr Ala Leu Phe Tyr Arg Leu Asp Val Val Gln Ile Asn Asn Asn Ser
130                 135                 140

Ser Asn Ser Ser Leu Tyr Arg Leu Ile Asn Cys Asn Thr Ser Thr Thr
145                 150                 155                 160

Thr Gln Ala Cys Pro Lys Val Thr Phe Glu Pro Ile Pro Ile His Tyr
            165                 170                 175

Cys Ala Pro Ala Gly Phe Ala Ile Leu Lys Cys Asn Asp Lys Lys Phe
            180                 185                 190

Asn Gly Thr Gly Pro Cys Lys Asn Val Ser Ser Val Gln Cys Thr His
            195                 200                 205

Gly Ile Arg Pro Val Val Ser Thr Gly Gly Gly Asp Met Arg Asp Asn
            210                 215                 220

Trp Arg Ser Glu Leu Tyr Lys Tyr Lys Val Val Lys Leu Glu Pro Leu
225                 230                 235                 240

Gly Val Ala Pro Thr Arg Ala Arg Arg Arg Val Val Thr Arg Glu Lys
            245                 250                 255

Arg

<210> SEQ ID NO 25
<211> LENGTH: 254
<212> TYPE: PRT
<213> ORGANISM: Artificial Sequence
<220> FEATURE:
<223> OTHER INFORMATION: ID immunogen yu2gp120_V1V2

<400> SEQUENCE: 25

Val Pro Val Trp Lys Glu Ala Thr Thr Thr Leu Phe Cys Ala Ser Asp
1               5                   10                  15

Ala Lys Ala Tyr Asp Thr Glu Cys His Asn Val Trp Ala Thr His Ala
            20                  25                  30

Cys Val Pro Thr Asp Pro Asn Pro Gln Glu Val Lys Leu Glu Asn Val
            35                  40                  45

Thr Glu Asn Phe Asn Met Trp Lys Asn Asn Met Val Glu Gln Met His
    50                  55                  60

Glu Asp Ile Ile Ser Leu Trp Asp Gln Cys Leu Lys Pro Cys Val Lys
65                  70                  75                  80

Leu Thr Pro Leu Cys Val Thr Leu Asn Cys Thr Asp Leu Arg Asn Ala
                85                  90                  95

Thr Asn Thr Thr Ser Ser Ser Trp Glu Thr Met Glu Lys Gly Glu Ile
            100                 105                 110

Lys Asn Cys Ser Phe Asn Ile Thr Thr Ser Ile Arg Asp Lys Val Gln
            115                 120                 125

Lys Glu Tyr Ala Leu Phe Tyr Asn Leu Asp Val Val Pro Ile Asp Asn
            130                 135                 140

Ala Ser Tyr Arg Leu Ile Ser Cys Asn Thr Ser Val Ile Thr Gln Ala
145                 150                 155                 160

Cys Pro Lys Val Ser Phe Glu Pro Ile Pro Ile His Tyr Cys Ala Pro
            165                 170                 175

Ala Gly Phe Ala Ile Leu Lys Cys Asn Asp Lys Lys Phe Asn Gly Thr
            180                 185                 190

Gly Pro Cys Thr Asn Val Ser Thr Val Gln Cys Thr His Gly Ile Arg
            195                 200                 205

Pro Val Val Ser Thr Gly Gly Gly Asp Met Arg Asp Asn Trp Arg Ser
            210                 215                 220

Glu Leu Tyr Lys Tyr Lys Val Val Lys Ile Glu Pro Leu Gly Val Ala
225                 230                 235                 240

```
Pro Thr Lys Ala Lys Arg Arg Val Val Gln Arg Glu Lys Arg
            245                 250
```

<210> SEQ ID NO 26
<211> LENGTH: 257
<212> TYPE: PRT
<213> ORGANISM: Artificial Sequence
<220> FEATURE:
<223> OTHER INFORMATION: ID immunogen HXB2_V1V2

<400> SEQUENCE: 26

```
Val Pro Val Trp Lys Glu Ala Thr Thr Thr Leu Phe Cys Ala Ser Asp
1               5                   10                  15

Ala Lys Ala Tyr Asp Thr Glu Cys His Asn Val Trp Ala Thr His Ala
            20                  25                  30

Cys Val Pro Thr Asp Pro Asn Pro Gln Glu Val Val Leu Val Asn Val
        35                  40                  45

Thr Glu Asn Phe Asn Met Trp Lys Asn Asp Met Val Glu Gln Met His
    50                  55                  60

Glu Asp Ile Ile Ser Leu Trp Asp Gln Cys Leu Lys Pro Cys Val Lys
65                  70                  75                  80

Leu Thr Pro Leu Cys Val Ser Leu Lys Cys Thr Asp Leu Lys Asn Asp
                85                  90                  95

Thr Asn Thr Asn Ser Ser Ser Gly Arg Met Ile Met Glu Lys Gly Glu
            100                 105                 110

Ile Lys Asn Cys Ser Phe Asn Ile Ser Thr Ser Ile Arg Gly Lys Val
        115                 120                 125

Gln Lys Glu Tyr Ala Phe Phe Tyr Lys Leu Asp Ile Ile Pro Ile Asp
    130                 135                 140

Asn Asp Thr Thr Ser Tyr Lys Leu Thr Ser Cys Asn Thr Ser Val Ile
145                 150                 155                 160

Thr Gln Ala Cys Pro Lys Val Ser Phe Glu Pro Ile Pro Ile His Tyr
                165                 170                 175

Cys Ala Pro Ala Gly Phe Ala Ile Leu Lys Cys Asn Asn Lys Thr Phe
            180                 185                 190

Asn Gly Thr Gly Pro Cys Thr Asn Val Ser Thr Val Gln Cys Thr His
        195                 200                 205

Gly Ile Arg Pro Val Val Ser Thr Gly Gly Asp Met Arg Asp Asn
    210                 215                 220

Trp Arg Ser Glu Leu Tyr Lys Tyr Lys Val Val Lys Ile Glu Pro Leu
225                 230                 235                 240

Gly Val Ala Pro Thr Lys Ala Lys Arg Arg Val Val Gln Arg Glu Lys
                245                 250                 255

Arg
```

<210> SEQ ID NO 27
<211> LENGTH: 259
<212> TYPE: PRT
<213> ORGANISM: Artificial Sequence
<220> FEATURE:
<223> OTHER INFORMATION: ID immunogen HM623558_V1V2

<400> SEQUENCE: 27

```
Val Pro Val Trp Lys Glu Ala Lys Thr Thr Leu Phe Cys Ala Ser Asp
1               5                   10                  15

Ala Lys Ala Tyr Glu Arg Glu Cys His Asn Val Trp Ala Thr His Ala
            20                  25                  30
```

Cys Val Pro Thr Asp Pro Asn Pro Gln Glu Ile Ala Leu Glu Asn Val
            35                  40                  45

Thr Glu Asn Phe Asn Met Trp Lys Asn Met Val Asp Gln Met His
 50                  55                  60

Glu Asp Ile Ile Ser Leu Trp Asp Gln Cys Leu Lys Pro Cys Val Lys
 65                  70                  75                  80

Leu Thr Pro Leu Cys Val Thr Leu Asn Cys Thr Asn Val Thr Lys Asn
                 85                  90                  95

Asp Thr Asn Ala Asn Asn Thr Ala Glu Gly Lys Glu Arg Lys Asn
                100                 105                 110

Cys Ser Phe Asn Ala Thr Thr Glu Leu Arg Asp Lys Asn Arg Lys Val
                115                 120                 125

Tyr Ala Leu Phe Tyr Lys Leu Asp Ile Val Pro Leu Asn Pro Ser Asn
            130                 135                 140

Asn Ser Asn Ser Ser Gly Gln Tyr Arg Leu Ile Thr Cys Asn Thr Ser
145                 150                 155                 160

Val Ile Thr Gln Ala Cys Pro Lys Ile Ile Phe Asp Pro Ile Pro Ile
                165                 170                 175

His Tyr Cys Ala Pro Ala Gly Tyr Ala Ile Leu Lys Cys Asn Asn Lys
                180                 185                 190

Thr Phe Asn Gly Thr Gly Pro Cys Asn Asn Val Ser Thr Val Gln Cys
            195                 200                 205

Thr His Gly Ile Lys Pro Val Ser Thr Gly Gly Asp Met Arg
        210                 215                 220

Asp Asn Trp Arg Ser Glu Leu Tyr Lys Tyr Lys Val Val Gln Ile Glu
225                 230                 235                 240

Pro Leu Gly Val Ala Pro Thr Lys Ala Lys Arg Val Val Gln Arg
                245                 250                 255

Glu Lys Arg

<210> SEQ ID NO 28
<211> LENGTH: 251
<212> TYPE: PRT
<213> ORGANISM: Artificial Sequence
<220> FEATURE:
<223> OTHER INFORMATION: ID immunogen DQ404010_V1V2

<400> SEQUENCE: 28

Val Pro Val Trp Lys Glu Ala Lys Thr Thr Leu Phe Cys Ala Ser Asp
 1               5                  10                  15

Ala Lys Ala Tyr Glu Lys Glu Cys His Asn Val Trp Ala Thr His Ala
                20                  25                  30

Cys Val Pro Thr Asp Pro Asn Pro Gln Glu Met Val Leu Glu Asn Val
            35                  40                  45

Thr Glu Asn Phe Asn Met Trp Lys Asn Asp Met Val Asn Gln Met His
 50                  55                  60

Glu Asp Val Ile Ser Leu Trp Asp Gln Cys Leu Lys Pro Cys Val Lys
 65                  70                  75                  80

Leu Thr Pro Leu Cys Val Thr Leu Glu Cys Gly Asn Val Thr Gln Asn
                 85                  90                  95

Gly Thr Tyr Asn Asp Glu Ser Asn Lys Glu Ile Thr Asn Cys Thr Phe
                100                 105                 110

Asn Thr Thr Thr Glu Ile Arg Gly Arg Lys Gln Lys Val Tyr Ala Leu
                115                 120                 125

Phe Tyr Lys Leu Asp Ile Val Pro Ile Ser Glu Thr Ser Asn Gln Ser

```
                130                 135                 140

Arg Leu Ile Ser Cys Asn Thr Ser Val Ile Thr Gln Ala Cys Pro Lys
145                 150                 155                 160

Val Ser Phe Asp Pro Ile Pro Ile His Tyr Cys Thr Pro Ala Gly Tyr
                165                 170                 175

Ala Ile Leu Lys Cys Asn Asp Lys Thr Phe Asn Gly Thr Gly Pro Cys
                180                 185                 190

Arg Asn Val Ser Thr Val Gln Cys Thr His Gly Ile Lys Pro Val Val
                195                 200                 205

Ser Thr Gly Gly Gly Asp Met Arg Asp Asn Trp Arg Ser Glu Leu Tyr
            210                 215                 220

Lys Tyr Lys Val Val Glu Ile Lys Pro Leu Gly Val Ala Pro Thr Thr
225                 230                 235                 240

Ala Lys Arg Arg Val Val Glu Arg Glu Lys Arg
                245                 250

<210> SEQ ID NO 29
<211> LENGTH: 173
<212> TYPE: PRT
<213> ORGANISM: Artificial Sequence
<220> FEATURE:
<223> OTHER INFORMATION: ID immunogen A1

<400> SEQUENCE: 29

Val Pro Val Trp Lys Asp Ala Glu Thr Thr Leu Phe Cys Ala Ser Asp
1               5                   10                  15

Ala Lys Ala Tyr Glu Thr Glu Cys His Asn Val Trp Ala Thr His Ala
                20                  25                  30

Cys Val Pro Thr Asp Pro Asn Pro Gln Glu Ile His Leu Glu Asn Val
            35                  40                  45

Thr Glu Glu Phe Asn Met Trp Lys Asn Asn Met Val Glu Gln Met His
        50                  55                  60

Thr Asp Ile Ile Ser Leu Trp Asp Gln Cys Leu Lys Pro Gly Gly Ala
65                  70                  75                  80

Pro Lys Val Ser Phe Glu Pro Ile Pro Ile His Tyr Cys Ala Pro Ala
                85                  90                  95

Gly Phe Ala Ile Leu Lys Cys Lys Asp Lys Glu Phe Asn Gly Thr Gly
                100                 105                 110

Pro Cys Lys Asn Val Ser Thr Val Gln Cys Thr His Gly Ile Lys Pro
                115                 120                 125

Val Val Ser Thr Gly Gly Gly Asp Met Arg Asp Asn Trp Arg Ser Glu
                130                 135                 140

Leu Tyr Lys Tyr Lys Val Val Lys Ile Glu Pro Leu Gly Val Ala Pro
145                 150                 155                 160

Thr Arg Ala Lys Arg Arg Val Val Glu Arg Glu Lys Arg
                165                 170

<210> SEQ ID NO 30
<211> LENGTH: 173
<212> TYPE: PRT
<213> ORGANISM: Artificial Sequence
<220> FEATURE:
<223> OTHER INFORMATION: ID immunogen A2

<400> SEQUENCE: 30

Val Pro Val Trp Lys Asp Ala Asp Thr Thr Leu Phe Cys Ala Ser Asp
1               5                   10                  15
```

Ala Lys Ala Tyr Asp Thr Glu Cys His Asn Val Trp Ala Thr His Ala
            20                  25                  30

Cys Val Pro Thr Asp Pro Asn Pro Gln Glu Val Asn Leu Glu Asn Val
            35                  40                  45

Thr Glu Asp Phe Asn Met Trp Lys Asn Asn Met Val Glu Gln Met His
50                  55                  60

Glu Asp Ile Ile Ser Leu Trp Asp Gln Cys Leu Lys Pro Gly Gly Ala
65                  70                  75                  80

Pro Lys Val Ser Phe Glu Pro Ile Pro Ile His Tyr Cys Ala Pro Ala
                85                  90                  95

Gly Phe Ala Ile Leu Lys Cys Lys Asp Pro Arg Phe Asn Gly Thr Gly
            100                 105                 110

Ser Cys Asn Asn Val Ser Ser Val Gln Cys Thr His Gly Ile Lys Pro
            115                 120                 125

Val Ala Ser Thr Gly Gly Gly Asp Met Arg Asp Asn Trp Arg Ser Glu
            130                 135                 140

Leu Tyr Lys Tyr Lys Val Val Lys Ile Glu Pro Leu Gly Val Ala Pro
145                 150                 155                 160

Thr Arg Ala Lys Arg Arg Val Val Glu Arg Glu Lys Arg
                165                 170

<210> SEQ ID NO 31
<211> LENGTH: 173
<212> TYPE: PRT
<213> ORGANISM: Artificial Sequence
<220> FEATURE:
<223> OTHER INFORMATION: ID immunogen B

<400> SEQUENCE: 31

Val Pro Val Trp Lys Glu Ala Thr Thr Thr Leu Phe Cys Ala Ser Asp
1               5                   10                  15

Ala Lys Ala Tyr Asp Thr Glu Cys His Asn Val Trp Ala Thr His Ala
            20                  25                  30

Cys Val Pro Thr Asp Pro Asn Pro Gln Glu Val Val Leu Glu Asn Val
            35                  40                  45

Thr Glu Asn Phe Asn Met Trp Lys Asn Asn Met Val Glu Gln Met His
50                  55                  60

Glu Asp Ile Ile Ser Leu Trp Asp Gln Cys Leu Lys Pro Gly Gly Ala
65                  70                  75                  80

Pro Lys Val Ser Phe Glu Pro Ile Pro Ile His Tyr Cys Ala Pro Ala
                85                  90                  95

Gly Phe Ala Ile Leu Lys Cys Asn Asp Lys Lys Phe Asn Gly Thr Gly
            100                 105                 110

Pro Cys Thr Asn Val Ser Thr Val Gln Cys Thr His Gly Ile Arg Pro
            115                 120                 125

Val Val Ser Thr Gly Gly Gly Asp Met Arg Asp Asn Trp Arg Ser Glu
            130                 135                 140

Leu Tyr Lys Tyr Lys Val Val Lys Ile Glu Pro Leu Gly Val Ala Pro
145                 150                 155                 160

Thr Lys Ala Lys Arg Arg Val Val Gln Arg Glu Lys Arg
                165                 170

<210> SEQ ID NO 32
<211> LENGTH: 173
<212> TYPE: PRT
<213> ORGANISM: Artificial Sequence
<220> FEATURE:

<223> OTHER INFORMATION: ID immunogen C

<400> SEQUENCE: 32

Val Pro Val Trp Lys Glu Ala Lys Thr Thr Leu Phe Cys Ala Ser Asp
1               5                   10                  15

Ala Lys Ala Tyr Glu Lys Glu Cys His Asn Val Trp Ala Thr His Ala
            20                  25                  30

Cys Val Pro Thr Asp Pro Asn Pro Gln Glu Ile Val Leu Glu Asn Val
        35                  40                  45

Thr Glu Asn Phe Asn Met Trp Lys Asn Asp Met Val Asp Gln Met His
50                  55                  60

Glu Asp Ile Ile Ser Leu Trp Asp Gln Cys Leu Lys Pro Gly Gly Ala
65                  70                  75                  80

Pro Lys Val Ser Phe Asp Pro Ile Pro Ile His Tyr Cys Ala Pro Ala
                85                  90                  95

Gly Tyr Ala Ile Leu Lys Cys Asn Asn Lys Thr Phe Asn Gly Thr Gly
            100                 105                 110

Pro Cys Asn Asn Val Ser Thr Val Gln Cys Thr His Gly Ile Lys Pro
        115                 120                 125

Val Val Ser Thr Gly Gly Gly Asp Met Arg Asp Asn Trp Arg Ser Glu
    130                 135                 140

Leu Tyr Lys Tyr Lys Val Val Glu Ile Lys Pro Leu Gly Ile Ala Pro
145                 150                 155                 160

Thr Lys Ala Lys Arg Arg Val Val Glu Arg Glu Lys Arg
                165                 170

<210> SEQ ID NO 33
<211> LENGTH: 173
<212> TYPE: PRT
<213> ORGANISM: Artificial Sequence
<220> FEATURE:
<223> OTHER INFORMATION: ID immunogen D

<400> SEQUENCE: 33

Val Pro Val Trp Lys Glu Ala Thr Thr Thr Leu Phe Cys Ala Ser Asp
1               5                   10                  15

Ala Lys Ser Tyr Lys Thr Glu Cys His Asn Ile Trp Ala Thr His Ala
            20                  25                  30

Cys Val Pro Thr Asp Pro Asn Pro Gln Glu Ile Glu Leu Glu Asn Val
        35                  40                  45

Thr Glu Asn Phe Asn Met Trp Lys Asn Asn Met Val Glu Gln Met His
50                  55                  60

Glu Asp Ile Ile Ser Leu Trp Asp Gln Cys Leu Lys Pro Gly Gly Ala
65                  70                  75                  80

Pro Lys Val Thr Phe Glu Pro Ile Pro Ile His Tyr Cys Ala Pro Ala
                85                  90                  95

Gly Phe Ala Ile Leu Lys Cys Lys Asp Lys Lys Phe Asn Gly Thr Gly
            100                 105                 110

Pro Cys Lys Asn Val Ser Thr Val Gln Cys Thr His Gly Ile Arg Pro
        115                 120                 125

Val Val Ser Thr Gly Gly Gly Asp Met Arg Asp Asn Trp Arg Ser Glu
    130                 135                 140

Leu Tyr Lys Tyr Lys Val Val Lys Ile Glu Pro Leu Gly Val Ala Pro
145                 150                 155                 160

Thr Arg Ala Lys Arg Arg Val Val Glu Arg Glu Lys Arg
                165                 170

<210> SEQ ID NO 34
<211> LENGTH: 173
<212> TYPE: PRT
<213> ORGANISM: Artificial Sequence
<220> FEATURE:
<223> OTHER INFORMATION: ID immunogen F1

<400> SEQUENCE: 34

```
Val Pro Val Trp Lys Glu Ala Thr Thr Thr Leu Phe Cys Ala Ser Asp
1               5                   10                  15

Ala Lys Ser Tyr Glu Lys Glu Cys His Asn Val Trp Ala Thr His Ala
            20                  25                  30

Cys Val Pro Thr Asp Pro Asn Pro Gln Glu Val Val Leu Glu Asn Val
        35                  40                  45

Thr Glu Asn Phe Asp Met Trp Lys Asn Met Val Glu Gln Met His
    50                  55                  60

Thr Asp Ile Ile Ser Leu Trp Asp Gln Cys Leu Lys Pro Gly Gly Ala
65                  70                  75                  80

Pro Lys Val Ser Trp Asp Pro Ile Pro Ile His Tyr Cys Ala Pro Ala
                85                  90                  95

Gly Tyr Ala Ile Leu Lys Cys Asn Asp Lys Arg Phe Asn Gly Thr Gly
                100                 105                 110

Pro Cys Lys Asn Val Ser Thr Val Gln Cys Thr His Gly Ile Lys Pro
            115                 120                 125

Val Val Ser Thr Gly Gly Asn Met Lys Asp Asn Trp Arg Ser Glu
        130                 135                 140

Leu Tyr Lys Tyr Lys Val Val Glu Ile Glu Pro Leu Gly Val Ala Pro
145                 150                 155                 160

Thr Lys Ala Lys Arg Gln Val Val Lys Arg Glu Arg Arg
                165                 170
```

<210> SEQ ID NO 35
<211> LENGTH: 173
<212> TYPE: PRT
<213> ORGANISM: Artificial Sequence
<220> FEATURE:
<223> OTHER INFORMATION: ID immunogen F2

<400> SEQUENCE: 35

```
Val Pro Val Trp Lys Glu Ala Thr Thr Thr Leu Phe Cys Ala Ser Asp
1               5                   10                  15

Ala Lys Ala Tyr Glu Arg Glu Cys His Asn Val Trp Ala Thr Tyr Ala
            20                  25                  30

Cys Val Pro Thr Asp Pro Ser Pro Gln Glu Leu Val Leu Gly Asn Val
        35                  40                  45

Thr Glu Asn Phe Asn Met Trp Lys Asn Asn Met Val Asp Gln Met His
    50                  55                  60

Glu Asp Ile Ile Ser Leu Trp Asp Gln Cys Leu Lys Pro Gly Gly Ala
65                  70                  75                  80

Pro Lys Val Ser Phe Glu Pro Ile Pro Ile His Tyr Cys Ala Pro Ala
                85                  90                  95

Gly Phe Ala Ile Leu Lys Cys Asn Asp Lys Lys Phe Asn Gly Thr Gly
                100                 105                 110

Leu Cys Arg Asn Val Ser Thr Val Gln Cys Thr His Gly Ile Arg Pro
            115                 120                 125

Val Val Ser Thr Gly Gly Gly Asp Met Arg Asp Asn Trp Arg Ser Glu
```

```
                130                 135                 140
Leu Tyr Lys Tyr Lys Val Val Lys Ile Glu Pro Leu Gly Val Ala Pro
145                 150                 155                 160

Thr Lys Ala Lys Arg Gln Val Val Gln Arg Glu Lys Arg
                165                 170
```

<210> SEQ ID NO 36
<211> LENGTH: 173
<212> TYPE: PRT
<213> ORGANISM: Artificial Sequence
<220> FEATURE:
<223> OTHER INFORMATION: ID immunogen G

<400> SEQUENCE: 36

```
Val Pro Val Trp Glu Asp Ala Asp Thr Thr Leu Phe Cys Ala Ser Asp
1               5                   10                  15

Ala Lys Ala Tyr Ser Thr Glu Cys His Asn Val Trp Ala Thr His Ala
                20                  25                  30

Cys Val Pro Thr Asp Pro Asn Pro Gln Glu Ile Thr Leu Glu Asn Val
            35                  40                  45

Thr Glu Asn Phe Asn Met Trp Lys Asn Asn Met Val Glu Gln Met His
50                  55                  60

Glu Asp Ile Ile Ser Leu Trp Asp Glu Cys Leu Lys Pro Gly Gly Ala
65                  70                  75                  80

Pro Lys Val Thr Phe Asp Pro Ile Pro Ile His Tyr Cys Ala Pro Ala
                85                  90                  95

Gly Phe Ala Ile Leu Lys Cys Arg Asp Lys Lys Phe Asn Gly Thr Gly
            100                 105                 110

Pro Cys Lys Asn Val Ser Thr Val Gln Cys Thr His Gly Ile Lys Pro
        115                 120                 125

Val Val Ser Thr Gly Gly Gly Asp Met Arg Asp Asn Trp Arg Ser Glu
    130                 135                 140

Leu Tyr Lys Tyr Lys Ile Val Lys Ile Lys Pro Leu Gly Val Ala Pro
145                 150                 155                 160

Thr Arg Ala Arg Arg Arg Val Val Glu Arg Glu Lys Arg
                165                 170
```

<210> SEQ ID NO 37
<211> LENGTH: 173
<212> TYPE: PRT
<213> ORGANISM: Artificial Sequence
<220> FEATURE:
<223> OTHER INFORMATION: ID immunogen H

<400> SEQUENCE: 37

```
Val Pro Val Trp Lys Glu Ala Lys Thr Thr Leu Phe Cys Ala Ser Asp
1               5                   10                  15

Ala Lys Ala Tyr Glu Thr Glu Cys His Asn Val Trp Ala Thr His Ala
                20                  25                  30

Cys Val Pro Thr Asp Pro Asn Pro Gln Glu Met Val Leu Glu Asn Val
            35                  40                  45

Thr Glu Asn Phe Asn Met Trp Glu Asn Asp Met Val Glu Gln Met His
50                  55                  60

Thr Asp Ile Ile Ser Leu Trp Asp Gln Cys Leu Lys Pro Gly Gly Ala
65                  70                  75                  80

Pro Lys Val Ser Phe Glu Pro Ile Pro Ile His Tyr Cys Ala Pro Ala
                85                  90                  95
```

Gly Phe Ala Ile Leu Lys Cys Asn Asn Lys Thr Phe Asn Gly Thr Gly
                100                 105                 110

Pro Cys Thr Asn Val Ser Thr Val Gln Cys Thr His Gly Ile Arg Pro
            115                 120                 125

Val Val Ser Thr Gly Gly Gly Asp Met Arg Asp Asn Trp Arg Ser Glu
        130                 135                 140

Leu Tyr Lys Tyr Lys Val Val Lys Ile Glu Pro Leu Gly Val Ala Pro
145                 150                 155                 160

Thr Glu Ala Arg Arg Arg Val Val Glu Arg Glu Lys Arg
                165                 170

<210> SEQ ID NO 38
<211> LENGTH: 173
<212> TYPE: PRT
<213> ORGANISM: Artificial Sequence
<220> FEATURE:
<223> OTHER INFORMATION: ID immunogen 01_AE

<400> SEQUENCE: 38

Val Pro Val Trp Arg Asp Ala Asp Thr Thr Leu Phe Cys Ala Ser Asp
1               5                   10                  15

Ala Lys Ala His Glu Thr Glu Cys His Asn Val Trp Ala Thr His Ala
                20                  25                  30

Cys Val Pro Thr Asp Pro Asn Pro Gln Glu Ile His Leu Glu Asn Val
            35                  40                  45

Thr Glu Asn Phe Asn Met Trp Lys Asn Asn Met Val Glu Gln Met Gln
        50                  55                  60

Glu Asp Val Ile Ser Leu Trp Asp Gln Cys Leu Lys Pro Gly Gly Ala
65                  70                  75                  80

Pro Lys Ile Ser Phe Asp Pro Ile Pro Ile His Tyr Cys Thr Pro Ala
                85                  90                  95

Gly Tyr Ala Ile Leu Lys Cys Asn Asp Lys Asn Phe Asn Gly Thr Gly
                100                 105                 110

Pro Cys Lys Asn Val Ser Ser Val Gln Cys Thr His Gly Ile Lys Pro
            115                 120                 125

Val Val Ser Thr Gly Gly Gly Asn Ile Lys Asp Asn Trp Arg Ser Glu
        130                 135                 140

Leu Tyr Lys Tyr Lys Val Val Gln Ile Glu Pro Leu Gly Ile Ala Pro
145                 150                 155                 160

Thr Arg Ala Lys Arg Arg Val Val Glu Arg Glu Lys Arg
                165                 170

<210> SEQ ID NO 39
<211> LENGTH: 173
<212> TYPE: PRT
<213> ORGANISM: Artificial Sequence
<220> FEATURE:
<223> OTHER INFORMATION: ID immunogen 02_AG

<400> SEQUENCE: 39

Val Pro Val Trp Arg Asp Ala Glu Thr Thr Leu Phe Cys Ala Ser Asp
1               5                   10                  15

Ala Lys Ala Tyr Asp Thr Glu Cys His Asn Val Trp Ala Thr His Ala
                20                  25                  30

Cys Val Pro Thr Asp Pro Asn Pro Gln Glu Ile His Leu Glu Asn Val
            35                  40                  45

Thr Glu Asn Phe Asn Met Trp Lys Asn Asn Met Val Glu Gln Met His
        50                  55                  60

```
Glu Asp Ile Ile Ser Leu Trp Asp Gln Cys Leu Lys Pro Gly Gly Ala
 65                  70                  75                  80

Pro Lys Val Ser Phe Glu Pro Ile Pro Ile His Tyr Cys Ala Pro Ala
                 85                  90                  95

Gly Phe Ala Ile Leu Lys Cys Asn Asp Lys Glu Phe Asn Gly Thr Gly
            100                 105                 110

Pro Cys Lys Asn Val Ser Thr Val Gln Cys Thr His Gly Ile Lys Pro
        115                 120                 125

Val Val Ser Thr Gly Gly Asp Met Arg Asp Asn Trp Arg Ser Glu
    130                 135                 140

Leu Tyr Lys Tyr Lys Val Val Lys Ile Glu Pro Leu Gly Val Ala Pro
145                 150                 155                 160

Thr Arg Ala Lys Arg Arg Val Val Glu Arg Glu Lys Arg
                165                 170

<210> SEQ ID NO 40
<211> LENGTH: 173
<212> TYPE: PRT
<213> ORGANISM: Artificial Sequence
<220> FEATURE:
<223> OTHER INFORMATION: ID immunogen 03_AB

<400> SEQUENCE: 40

Val Pro Val Trp Lys Glu Ala Thr Thr Thr Leu Phe Cys Ala Ser Asp
  1               5                  10                  15

Ala Lys Ala Tyr Ser Lys Glu Cys His Asn Val Trp Ala Thr Tyr Ala
             20                  25                  30

Cys Val Pro Thr Asp Pro Ser Pro Gln Glu Ile Pro Leu Glu Asn Val
         35                  40                  45

Thr Glu Asn Phe Asn Met Gly Lys Asn Asn Met Val Glu Gln Met His
     50                  55                  60

Glu Asp Ile Ile Ser Leu Trp Asp Gln Cys Leu Lys Pro Gly Gly Ala
 65                  70                  75                  80

Pro Lys Ile Ser Phe Glu Pro Ile Pro Ile His Tyr Cys Ala Pro Ala
                 85                  90                  95

Gly Phe Ala Ile Leu Lys Cys Asn Asp Lys Lys Phe Asn Gly Thr Gly
            100                 105                 110

Pro Cys Thr Asn Val Ser Thr Val Gln Cys Thr His Gly Ile Lys Pro
        115                 120                 125

Val Val Ser Thr Gly Gly Asp Met Arg Asp Asn Trp Arg Ser Glu
    130                 135                 140

Leu Tyr Lys Tyr Lys Val Val Lys Ile Glu Pro Leu Gly Val Ala Pro
145                 150                 155                 160

Thr Lys Ala Lys Arg Arg Val Val Gln Arg Glu Lys Arg
                165                 170

<210> SEQ ID NO 41
<211> LENGTH: 173
<212> TYPE: PRT
<213> ORGANISM: Artificial Sequence
<220> FEATURE:
<223> OTHER INFORMATION: ID immunogen 04_CPX

<400> SEQUENCE: 41

Val Pro Val Trp Arg Asp Ala Glu Thr Thr Pro Phe Cys Ala Ser Asp
  1               5                  10                  15

Ala Lys Ala Tyr Asp Lys Glu Cys His Asn Ile Trp Ala Thr His Ala
```

```
                    20                  25                  30
Cys Val Pro Thr Asp Pro Asn Pro Gln Glu Ile Ala Leu Lys Asn Val
                35                  40                  45

Thr Glu Asn Phe Asn Met Trp Lys Asn Met Val Glu Gln Met His
    50                  55                  60

Glu Asp Ile Ile Ser Leu Trp Asp Glu Cys Leu Lys Pro Gly Gly Ala
65                  70                  75                  80

Pro Lys Val Thr Phe Glu Pro Ile Pro Ile His Tyr Cys Ala Pro Ala
                85                  90                  95

Gly Phe Ala Ile Leu Lys Cys Asn Asp Lys Asn Phe Thr Gly Leu Gly
                100                 105                 110

Pro Cys Thr Asn Val Ser Ser Val Gln Cys Thr His Gly Ile Lys Pro
                115                 120                 125

Val Val Ser Thr Gly Gly Gly Asp Met Arg Asp Asn Trp Arg Ser Glu
                130                 135                 140

Leu Tyr Lys Tyr Lys Val Val Lys Ile Glu Pro Val Gly Val Ala Pro
145                 150                 155                 160

Thr Arg Ala Arg Arg Arg Val Val Gln Arg Glu Lys Arg
                165                 170

<210> SEQ ID NO 42
<211> LENGTH: 173
<212> TYPE: PRT
<213> ORGANISM: Artificial Sequence
<220> FEATURE:
<223> OTHER INFORMATION: ID immunogen 06_CPX

<400> SEQUENCE: 42

Val Pro Ala Trp Glu Asp Ala Asp Thr Ile Leu Phe Cys Ala Ser Asp
1               5                   10                  15

Ala Lys Ala Tyr Ser Ala Glu Cys His Asn Val Trp Ala Thr His Ala
                20                  25                  30

Cys Val Pro Thr Asp Pro Asn Pro Gln Glu Ile Ala Leu Glu Asn Val
                35                  40                  45

Thr Glu Asn Phe Asn Met Trp Lys Asn His Met Val Glu Gln Met His
    50                  55                  60

Glu Asp Ile Ile Ser Leu Trp Asp Glu Cys Leu Lys Pro Gly Gly Ala
65                  70                  75                  80

Pro Lys Val Ser Phe Glu Pro Ile Pro Ile His Tyr Cys Ala Pro Ala
                85                  90                  95

Gly Phe Ala Ile Leu Lys Cys Arg Asp Lys Asn Phe Asn Gly Thr Gly
                100                 105                 110

Pro Cys Lys Asn Val Ser Thr Val Gln Cys Thr His Gly Ile Lys Pro
                115                 120                 125

Val Val Ser Thr Gly Gly Gly Asp Met Arg Asp Asn Trp Arg Ser Glu
                130                 135                 140

Leu Tyr Lys Tyr Lys Val Val Lys Ile Lys Pro Leu Gly Ile Ala Pro
145                 150                 155                 160

Thr Arg Ala Arg Arg Arg Val Val Gly Arg Glu Lys Arg
                165                 170

<210> SEQ ID NO 43
<211> LENGTH: 173
<212> TYPE: PRT
<213> ORGANISM: Artificial Sequence
<220> FEATURE:
<223> OTHER INFORMATION: ID immunogen 08_BC
```

<400> SEQUENCE: 43

```
Val Pro Val Trp Lys Glu Ala Lys Thr Thr Leu Phe Cys Ala Ser Asp
1               5                   10                  15

Ala Lys Ala Tyr Glu Thr Glu Cys His Asn Val Trp Ala Thr His Ala
            20                  25                  30

Cys Val Pro Thr Asp Pro Asn Pro Gln Glu Ile Val Met Glu Asn Val
        35                  40                  45

Thr Glu Asn Phe Asn Met Trp Asn Asn Asp Met Val Asn Gln Met His
    50                  55                  60

Glu Asp Val Ile Ser Leu Trp Asp Gln Cys Leu Lys Pro Gly Gly Ala
65                  70                  75                  80

Pro Lys Val Thr Phe Asp Pro Ile Pro Ile His Tyr Cys Thr Pro Ala
                85                  90                  95

Gly Tyr Ala Ile Leu Lys Cys Asn Asp Lys Lys Phe Asn Gly Thr Gly
            100                 105                 110

Gln Cys His Asn Val Ser Thr Val Gln Cys Thr His Gly Ile Lys Pro
        115                 120                 125

Val Val Ser Thr Gly Gly Gly Asp Met Arg Asn Asn Trp Arg Asn Glu
    130                 135                 140

Leu Tyr Lys Tyr Lys Val Val Glu Ile Lys Pro Leu Gly Val Ala Pro
145                 150                 155                 160

Thr Ala Ala Lys Arg Arg Val Val Glu Arg Glu Lys Arg
                165                 170
```

<210> SEQ ID NO 44
<211> LENGTH: 173
<212> TYPE: PRT
<213> ORGANISM: Artificial Sequence
<220> FEATURE:
<223> OTHER INFORMATION: ID immunogen 10_CD

<400> SEQUENCE: 44

```
Val Pro Val Trp Lys Glu Thr Thr Thr Thr Leu Phe Cys Ala Ser Asp
1               5                   10                  15

Ala Lys Ala Tyr Lys Ala Glu Cys His Asn Ile Trp Ala Thr His Ala
            20                  25                  30

Cys Val Pro Thr Asp Pro Asn Pro Gln Glu Ile Val Leu Glu Asn Val
        35                  40                  45

Thr Glu Asn Phe Asn Met Trp Lys Asn Gly Met Val Asp Gln Met His
    50                  55                  60

Glu Asp Ile Ile Ser Leu Trp Asp Gln Cys Leu Lys Pro Gly Gly Ala
65                  70                  75                  80

Pro Lys Val Thr Phe Glu Pro Ile Pro Ile His Tyr Cys Ala Pro Ala
                85                  90                  95

Gly Phe Ala Ile Leu Lys Cys Asn Asp Lys Lys Phe Asn Gly Thr Gly
            100                 105                 110

Pro Cys Lys Asn Val Ser Thr Val Gln Cys Thr His Gly Ile Lys Pro
        115                 120                 125

Val Val Ser Thr Gly Gly Gly Asp Met Arg Asp Asn Trp Arg Ser Glu
    130                 135                 140

Leu Tyr Lys Tyr Lys Val Val Lys Ile Glu Pro Leu Gly Leu Ala Pro
145                 150                 155                 160

Thr Lys Ala Lys Arg Arg Val Val Glu Arg Glu Lys Arg
                165                 170
```

```
<210> SEQ ID NO 45
<211> LENGTH: 173
<212> TYPE: PRT
<213> ORGANISM: Artificial Sequence
<220> FEATURE:
<223> OTHER INFORMATION: ID immunogen 11_CPX

<400> SEQUENCE: 45

Val Pro Val Trp Lys Asp Ala Asp Thr Thr Leu Phe Cys Ala Ser Asp
1               5                   10                  15

Ala Lys Ala Tyr Ser Thr Glu Cys His Asn Val Trp Ala Thr His Ala
            20                  25                  30

Cys Val Pro Thr Asp Pro Asn Pro Gln Glu Ile Pro Leu Glu Asn Val
        35                  40                  45

Thr Glu Asn Phe Asn Met Trp Lys Asn Asn Met Val Glu Gln Met His
    50                  55                  60

Glu Asp Ile Ile Ser Leu Trp Asp Glu Cys Leu Lys Pro Gly Gly Ala
65                  70                  75                  80

Pro Lys Val Thr Phe Glu Pro Ile Pro Ile His Tyr Cys Ala Pro Ala
                85                  90                  95

Gly Phe Ala Ile Leu Lys Cys Asn Asp Lys Lys Phe Asn Gly Thr Gly
            100                 105                 110

Pro Cys Lys Asn Val Ser Thr Val Gln Cys Thr His Gly Ile Lys Pro
        115                 120                 125

Val Val Ser Thr Thr Gly Gly Asp Met Arg Asp Asn Trp Arg Ser Glu
    130                 135                 140

Leu Tyr Lys Tyr Lys Val Glu Ile Lys Pro Leu Gly Val Ala Pro
145                 150                 155                 160

Thr Arg Ala Lys Arg Arg Val Val Glu Arg Glu Lys Arg
                165                 170

<210> SEQ ID NO 46
<211> LENGTH: 173
<212> TYPE: PRT
<213> ORGANISM: Artificial Sequence
<220> FEATURE:
<223> OTHER INFORMATION: ID immunogen 12_BF

<400> SEQUENCE: 46

Val Pro Val Trp Lys Glu Ala Thr Thr Thr Leu Phe Cys Ala Ser Asp
1               5                   10                  15

Ala Lys Ser Tyr Glu Arg Glu Cys His Asn Val Trp Ala Thr His Ala
            20                  25                  30

Cys Val Pro Thr Asp Pro Asn Pro Gln Glu Val Asp Leu Glu Asn Val
        35                  40                  45

Thr Glu Asn Phe Asp Met Trp Lys Asn Asn Met Val Glu Gln Met His
    50                  55                  60

Thr Asp Ile Ile Ser Leu Trp Asp Gln Cys Leu Lys Pro Gly Gly Ala
65                  70                  75                  80

Pro Lys Val Ser Trp Asp Pro Ile Pro Ile His Tyr Cys Ala Pro Ala
                85                  90                  95

Gly Tyr Ala Ile Leu Lys Cys Asn Asp Lys Lys Phe Asn Gly Thr Gly
            100                 105                 110

Pro Cys Lys Asn Val Ser Thr Val Gln Cys Thr His Gly Ile Lys Pro
        115                 120                 125

Val Val Ser Thr Gly Gly Gly Asn Met Lys Asp Asn Trp Arg Ser Glu
    130                 135                 140
```

```
Leu Tyr Lys Tyr Lys Val Val Glu Ile Glu Pro Leu Gly Val Ala Pro
145                 150                 155                 160

Thr Arg Ala Lys Arg Gln Val Val Lys Arg Glu Lys Arg
                165                 170
```

<210> SEQ ID NO 47
<211> LENGTH: 173
<212> TYPE: PRT
<213> ORGANISM: Artificial Sequence
<220> FEATURE:
<223> OTHER INFORMATION: ID immunogen 14_BG

<400> SEQUENCE: 47

```
Val Pro Val Trp Lys Glu Ala Thr Thr Thr Leu Phe Cys Ala Ser Asp
1               5                   10                  15

Ala Lys Ala Tyr Asp Ala Glu Cys His Asn Val Trp Ala Thr His Ala
                20                  25                  30

Cys Val Pro Thr Asp Pro Asn Pro Gln Glu Val Ala Leu Glu Asn Val
            35                  40                  45

Thr Glu Asn Phe Asn Met Trp Glu Asn Asn Met Val Asp Gln Met Gln
    50                  55                  60

Glu Asp Ile Ile Ser Leu Trp Asp Gln Cys Leu Lys Pro Gly Gly Ala
65                  70                  75                  80

Pro Lys Val Ser Phe Thr Pro Ile Pro Ile His Tyr Cys Ala Pro Ala
                85                  90                  95

Gly Phe Val Ile Leu Lys Cys Asn Asn Lys Thr Phe Asn Gly Thr Gly
                100                 105                 110

Pro Cys Thr Asn Val Ser Thr Val Gln Cys Thr His Gly Ile Arg Pro
            115                 120                 125

Val Val Ser Thr Gly Gly Gly Asn Met Lys Asp Asn Trp Arg Ser Glu
    130                 135                 140

Leu Tyr Lys Tyr Lys Val Val Lys Ile Glu Pro Leu Gly Val Ala Pro
145                 150                 155                 160

Thr Arg Ala Lys Arg Arg Val Val Gln Arg Glu Lys Arg
                165                 170
```

<210> SEQ ID NO 48
<211> LENGTH: 173
<212> TYPE: PRT
<213> ORGANISM: Artificial Sequence
<220> FEATURE:
<223> OTHER INFORMATION: ID immunogen CON_OF_CONS

<400> SEQUENCE: 48

```
Val Pro Val Trp Lys Glu Ala Asn Thr Thr Leu Phe Cys Ala Ser Asp
1               5                   10                  15

Ala Lys Ala Tyr Asp Thr Glu Cys His Asn Val Trp Ala Thr His Ala
                20                  25                  30

Cys Val Pro Thr Asp Pro Asn Pro Gln Glu Ile Val Leu Glu Asn Val
            35                  40                  45

Thr Glu Asn Phe Asn Met Trp Lys Asn Asn Met Val Glu Gln Met His
    50                  55                  60

Glu Asp Ile Ile Ser Leu Trp Asp Gln Cys Leu Lys Pro Gly Gly Ala
65                  70                  75                  80

Pro Lys Val Ser Phe Glu Pro Ile Pro Ile His Tyr Cys Ala Pro Ala
                85                  90                  95

Gly Phe Ala Ile Leu Lys Cys Asn Asp Lys Lys Phe Asn Gly Thr Gly
```

```
                  100                 105                 110
Pro Cys Lys Asn Val Ser Thr Val Gln Cys Thr His Gly Ile Lys Pro
                115                 120                 125

Val Val Ser Thr Gly Gly Gly Asp Met Arg Asp Asn Trp Arg Ser Glu
        130                 135                 140

Leu Tyr Lys Tyr Lys Val Val Lys Ile Glu Pro Leu Gly Val Ala Pro
145                 150                 155                 160

Thr Lys Ala Lys Arg Arg Val Val Glu Arg Glu Lys Arg
                165                 170

<210> SEQ ID NO 49
<211> LENGTH: 173
<212> TYPE: PRT
<213> ORGANISM: Artificial Sequence
<220> FEATURE:
<223> OTHER INFORMATION: ID immunogen AB097872

<400> SEQUENCE: 49

Val Pro Val Trp Arg Asp Ala Glu Thr Thr Leu Phe Cys Ala Ser Asp
1               5                   10                  15

Ala Lys Ala His Val Gly Glu Cys His Asn Val Trp Ala Thr His Ala
            20                  25                  30

Cys Val Pro Thr Asp Pro Asn Pro Gln Glu Ile His Leu Glu Asn Val
        35                  40                  45

Thr Glu Asn Phe Asn Met Trp Lys Asn Lys Met Ala Asp Gln Met Gln
    50                  55                  60

Glu Asp Val Ile Ser Leu Trp Asp Gln Cys Leu Lys Pro Gly Gly Ala
65                  70                  75                  80

Pro Lys Val Ser Phe Asp Pro Ile Pro Ile His Tyr Cys Thr Pro Ala
                85                  90                  95

Gly Phe Ala Ile Leu Lys Cys Asn Asp Lys Lys Phe Asn Gly Thr Gly
                100                 105                 110

Pro Cys Lys Asn Val Ser Val Gln Cys Thr His Gly Ile Lys Pro
                115                 120                 125

Val Val Ser Thr Gly Gly Gly Asn Ile Lys Asp Asn Trp Arg Ser Glu
        130                 135                 140

Leu Tyr Lys Tyr Lys Val Val Glu Ile Glu Pro Leu Gly Ile Ala Pro
145                 150                 155                 160

Thr Arg Ala Lys Arg Arg Val Val Glu Arg Gln Lys Arg
                165                 170

<210> SEQ ID NO 50
<211> LENGTH: 173
<212> TYPE: PRT
<213> ORGANISM: Artificial Sequence
<220> FEATURE:
<223> OTHER INFORMATION: ID immunogen AB052867

<400> SEQUENCE: 50

Val Pro Val Trp Lys Asp Ala Glu Thr Thr Leu Phe Cys Ala Ser Asp
1               5                   10                  15

Ala Lys Ala Tyr Asp Ala Glu Cys His Asn Val Trp Ala Thr His Ala
            20                  25                  30

Cys Val Pro Thr Asp Pro Asn Pro Gln Glu Ile Ser Leu Glu Asn Val
        35                  40                  45

Thr Glu Asp Phe Asn Met Trp Lys Asn Lys Met Val Glu Gln Met His
    50                  55                  60
```

```
Val Asp Ile Ile Ser Leu Trp Asp Gln Cys Leu Lys Pro Gly Gly Ala
 65                  70                  75                  80

Pro Lys Val Thr Phe Glu Pro Ile Pro Ile His Tyr Cys Ala Pro Ala
                 85                  90                  95

Gly Phe Ala Ile Leu Lys Cys Asn Asp Lys Lys Phe Asn Gly Thr Gly
            100                 105                 110

Pro Cys Lys Asn Val Ser Ser Val Gln Cys Thr His Gly Ile Arg Pro
        115                 120                 125

Val Val Ser Thr Gly Gly Gly Asp Met Arg Asp Asn Trp Arg Ser Glu
    130                 135                 140

Leu Tyr Lys Tyr Lys Val Val Lys Leu Glu Pro Leu Gly Val Ala Pro
145                 150                 155                 160

Thr Arg Ala Arg Arg Arg Val Val Thr Arg Glu Lys Arg
                165                 170
```

<210> SEQ ID NO 51
<211> LENGTH: 173
<212> TYPE: PRT
<213> ORGANISM: Artificial Sequence
<220> FEATURE:
<223> OTHER INFORMATION: ID immunogen yu2gp120

<400> SEQUENCE: 51

```
Val Pro Val Trp Lys Glu Ala Thr Thr Thr Leu Phe Cys Ala Ser Asp
 1               5                  10                  15

Ala Lys Ala Tyr Asp Thr Glu Cys His Asn Val Trp Ala Thr His Ala
                20                  25                  30

Cys Val Pro Thr Asp Pro Asn Pro Gln Glu Val Lys Leu Glu Asn Val
             35                  40                  45

Thr Glu Asn Phe Asn Met Trp Lys Asn Met Val Glu Gln Met His
 50                  55                  60

Glu Asp Ile Ile Ser Leu Trp Asp Gln Cys Leu Lys Pro Gly Gly Ala
 65                  70                  75                  80

Pro Lys Val Ser Phe Glu Pro Ile Pro Ile His Tyr Cys Ala Pro Ala
                 85                  90                  95

Gly Phe Ala Ile Leu Lys Cys Asn Asp Lys Lys Phe Asn Gly Thr Gly
            100                 105                 110

Pro Cys Thr Asn Val Ser Thr Val Gln Cys Thr His Gly Ile Arg Pro
        115                 120                 125

Val Val Ser Thr Gly Gly Gly Asp Met Arg Asp Asn Trp Arg Ser Glu
    130                 135                 140

Leu Tyr Lys Tyr Lys Val Val Lys Ile Glu Pro Leu Gly Val Ala Pro
145                 150                 155                 160

Thr Lys Ala Lys Arg Arg Val Val Gln Arg Glu Lys Arg
                165                 170
```

<210> SEQ ID NO 52
<211> LENGTH: 173
<212> TYPE: PRT
<213> ORGANISM: Artificial Sequence
<220> FEATURE:
<223> OTHER INFORMATION: ID immunogen HXB2

<400> SEQUENCE: 52

```
Val Pro Val Trp Lys Glu Ala Thr Thr Thr Leu Phe Cys Ala Ser Asp
 1               5                  10                  15

Ala Lys Ala Tyr Asp Thr Glu Cys His Asn Val Trp Ala Thr His Ala
                20                  25                  30
```

```
Cys Val Pro Thr Asp Pro Asn Pro Gln Glu Val Val Leu Val Asn Val
        35                  40                  45

Thr Glu Asn Phe Asn Met Trp Lys Asn Asp Met Val Glu Gln Met His
 50                  55                  60

Glu Asp Ile Ile Ser Leu Trp Asp Gln Cys Leu Lys Pro Gly Gly Ala
 65                  70                  75                  80

Pro Lys Val Ser Phe Glu Pro Ile Pro Ile His Tyr Cys Ala Pro Ala
                 85                  90                  95

Gly Phe Ala Ile Leu Lys Cys Asn Asn Lys Thr Phe Asn Gly Thr Gly
             100                 105                 110

Pro Cys Thr Asn Val Ser Thr Val Gln Cys Thr His Gly Ile Arg Pro
         115                 120                 125

Val Val Ser Thr Gly Gly Gly Asp Met Arg Asp Asn Trp Arg Ser Glu
     130                 135                 140

Leu Tyr Lys Tyr Lys Val Val Lys Ile Glu Pro Leu Gly Val Ala Pro
145                 150                 155                 160

Thr Lys Ala Lys Arg Arg Val Val Gln Arg Glu Lys Arg
                 165                 170
```

<210> SEQ ID NO 53
<211> LENGTH: 173
<212> TYPE: PRT
<213> ORGANISM: Artificial Sequence
<220> FEATURE:
<223> OTHER INFORMATION: ID immunogen HM623558

<400> SEQUENCE: 53

```
Val Pro Val Trp Lys Glu Ala Lys Thr Thr Leu Phe Cys Ala Ser Asp
 1               5                  10                  15

Ala Lys Ala Tyr Glu Arg Glu Cys His Asn Val Trp Ala Thr His Ala
             20                  25                  30

Cys Val Pro Thr Asp Pro Asn Pro Gln Glu Ile Ala Leu Glu Asn Val
        35                  40                  45

Thr Glu Asn Phe Asn Met Trp Lys Asn Asn Met Val Asp Gln Met His
 50                  55                  60

Glu Asp Ile Ile Ser Leu Trp Asp Gln Cys Leu Lys Pro Gly Gly Ala
 65                  70                  75                  80

Pro Lys Ile Ile Phe Asp Pro Ile Pro Ile His Tyr Cys Ala Pro Ala
                 85                  90                  95

Gly Tyr Ala Ile Leu Lys Cys Asn Asn Lys Thr Phe Asn Gly Thr Gly
             100                 105                 110

Pro Cys Asn Asn Val Ser Thr Val Gln Cys Thr His Gly Ile Lys Pro
         115                 120                 125

Val Val Ser Thr Gly Gly Gly Asp Met Arg Asp Asn Trp Arg Ser Glu
     130                 135                 140

Leu Tyr Lys Tyr Lys Val Val Gln Ile Glu Pro Leu Gly Val Ala Pro
145                 150                 155                 160

Thr Lys Ala Lys Arg Arg Val Val Gln Arg Glu Lys Arg
                 165                 170
```

<210> SEQ ID NO 54
<211> LENGTH: 173
<212> TYPE: PRT
<213> ORGANISM: Artificial Sequence
<220> FEATURE:
<223> OTHER INFORMATION: ID immunogen DQ404010

```
<400> SEQUENCE: 54

Val Pro Val Trp Lys Glu Ala Lys Thr Thr Leu Phe Cys Ala Ser Asp
1               5                   10                  15

Ala Lys Ala Tyr Glu Lys Glu Cys His Asn Val Trp Ala Thr His Ala
            20                  25                  30

Cys Val Pro Thr Asp Pro Asn Pro Gln Glu Met Val Leu Glu Asn Val
        35                  40                  45

Thr Glu Asn Phe Asn Met Trp Lys Asn Asp Met Val Asn Gln Met His
    50                  55                  60

Glu Asp Val Ile Ser Leu Trp Asp Gln Cys Leu Lys Pro Gly Gly Ala
65                  70                  75                  80

Pro Lys Val Ser Phe Asp Pro Ile Pro Ile His Tyr Cys Thr Pro Ala
                85                  90                  95

Gly Tyr Ala Ile Leu Lys Cys Asn Asp Lys Thr Phe Asn Gly Thr Gly
            100                 105                 110

Pro Cys Arg Asn Val Ser Thr Val Gln Cys Thr His Gly Ile Lys Pro
        115                 120                 125

Val Val Ser Thr Gly Gly Asp Met Arg Asp Asn Trp Arg Ser Glu
    130                 135                 140

Leu Tyr Lys Tyr Lys Val Val Glu Ile Lys Pro Leu Gly Val Ala Pro
145                 150                 155                 160

Thr Thr Ala Lys Arg Arg Val Val Glu Arg Glu Lys Arg
                165                 170

<210> SEQ ID NO 55
<211> LENGTH: 505
<212> TYPE: PRT
<213> ORGANISM: Human immunodeficiency virus type 1

<400> SEQUENCE: 55

Met Arg Val Lys Glu Thr Gln Met Asn Trp Pro Asn Leu Trp Lys Trp
1               5                   10                  15

Gly Thr Leu Ile Leu Gly Leu Val Ile Ile Cys Ser Ala Ser Asp Asn
            20                  25                  30

Leu Trp Val Thr Val Tyr Tyr Gly Val Pro Val Trp Lys Asp Ala Asp
        35                  40                  45

Thr Thr Leu Phe Cys Ala Ser Asp Ala Lys Ala His Glu Thr Glu Val
    50                  55                  60

His Asn Val Trp Ala Thr His Ala Cys Val Pro Thr Asp Pro Asn Pro
65                  70                  75                  80

Gln Glu Ile His Leu Glu Asn Val Thr Glu Asn Phe Asn Met Trp Lys
                85                  90                  95

Asn Asn Met Val Glu Gln Met Gln Glu Asp Val Ile Ser Leu Trp Asp
            100                 105                 110

Gln Ser Leu Gln Pro Cys Val Lys Leu Thr Pro Leu Cys Val Thr Leu
        115                 120                 125

His Cys Thr Thr Ala Lys Leu Thr Asn Val Thr Asn Ile Thr Asn Val
    130                 135                 140

Pro Asn Ile Gly Asn Ile Thr Asp Glu Val Arg Asn Cys Ser Phe Asn
145                 150                 155                 160

Met Thr Thr Glu Ile Arg Asp Lys Lys Gln Lys Val His Ala Leu Phe
                165                 170                 175

Tyr Lys Leu Asp Ile Val Gln Ile Glu Asp Lys Asn Asp Ser Ser Lys
            180                 185                 190
```

```
Tyr Arg Leu Ile Asn Cys Asn Thr Ser Val Ile Lys Gln Ala Cys Pro
            195                 200                 205

Lys Ile Ser Phe Asp Pro Ile Pro Ile His Tyr Cys Thr Pro Ala Gly
210                 215                 220

Tyr Val Ile Leu Lys Cys Asn Asp Lys Asn Phe Asn Gly Thr Gly Pro
225                 230                 235                 240

Cys Lys Asn Val Ser Ser Val Gln Cys Thr His Gly Ile Lys Pro Val
                245                 250                 255

Val Ser Thr Gln Leu Leu Leu Asn Gly Ser Leu Ala Glu Glu Glu Ile
            260                 265                 270

Ile Ile Arg Ser Glu Asn Leu Thr Asn Asn Ala Lys Thr Ile Ile Val
        275                 280                 285

His Leu Asn Lys Ser Val Glu Ile Asn Cys Thr Arg Pro Ser Asn Asn
    290                 295                 300

Met Arg Thr Ser Met Arg Ile Gly Pro Gly Gln Val Phe Tyr Arg Thr
305                 310                 315                 320

Gly Ser Ile Thr Gly Asp Ile Arg Lys Ala Tyr Cys Glu Ile Asn Gly
                325                 330                 335

Thr Lys Trp Asn Lys Val Leu Lys Gln Val Thr Glu Lys Leu Lys Glu
            340                 345                 350

His Phe Asn Asn Lys Thr Ile Ile Phe Gln Pro Pro Ser Gly Gly Asp
        355                 360                 365

Leu Glu Ile Thr Met His His Phe Asn Cys Arg Gly Glu Phe Phe Tyr
    370                 375                 380

Cys Asn Thr Thr Gln Leu Phe Asn Asn Thr Cys Ile Gly Asn Glu Thr
385                 390                 395                 400

Met Lys Gly Cys Asn Gly Thr Ile Thr Leu Pro Cys Lys Ile Lys Gln
                405                 410                 415

Ile Ile Asn Met Trp Gln Gly Thr Gly Gln Ala Met Tyr Ala Pro Pro
            420                 425                 430

Ile Asp Gly Lys Ile Asn Cys Val Ser Asn Ile Thr Gly Ile Leu Leu
        435                 440                 445

Thr Arg Asp Gly Gly Ala Asn Asn Thr Ser Asn Glu Thr Phe Arg Pro
    450                 455                 460

Gly Gly Gly Asn Ile Lys Asp Asn Trp Arg Ser Glu Leu Tyr Lys Tyr
465                 470                 475                 480

Lys Val Val Gln Ile Glu Pro Leu Gly Ile Ala Pro Thr Arg Ala Lys
                485                 490                 495

Arg Arg Val Val Glu Arg Glu Lys Arg
            500                 505

<210> SEQ ID NO 56
<211> LENGTH: 169
<212> TYPE: PRT
<213> ORGANISM: Artificial Sequence
<220> FEATURE:
<223> OTHER INFORMATION: ID immunogen ID1
<220> FEATURE:
<221> NAME/KEY: MISC_FEATURE
<223> OTHER INFORMATION: ID immunogen ID1

<400> SEQUENCE: 56

Val Pro Val Trp Lys Asp Ala Asp Thr Thr Leu Phe Cys Ala Ser Asp
1               5                   10                  15

Ala Lys Ala His Glu Thr Glu Val His Asn Val Trp Ala Thr His Ala
            20                  25                  30
```

```
Cys Val Pro Thr Asp Pro Asn Pro Gln Glu Ile His Leu Glu Asn Val
             35                  40                  45

Thr Glu Asn Phe Asn Met Trp Lys Asn Met Val Glu Gln Met Gln
 50                  55                  60

Glu Asp Val Ile Ser Leu Trp Asp Gln Ser Leu Gln Pro Cys Val Lys
 65                  70                  75                  80

Leu Thr Gly Gly Ser Val Ile Lys Gln Ala Cys Pro Lys Ile Ser Phe
                 85                  90                  95

Asp Pro Ile Pro Ile His Tyr Cys Thr Pro Ala Gly Tyr Val Ile Leu
            100                 105                 110

Lys Cys Asn Asp Lys Asn Phe Asn Gly Thr Gly Pro Cys Lys Asn Val
            115                 120                 125

Ser Ser Val Gln Cys Thr His Gly Ile Lys Pro Val Val Ser Ser Gly
            130                 135                 140

Gly Gly Asn Ile Lys Asp Asn Trp Arg Ser Glu Leu Tyr Lys Tyr Lys
145                 150                 155                 160

Val Val Gln Ile Glu Pro Leu Gly Ile
                165

<210> SEQ ID NO 57
<211> LENGTH: 154
<212> TYPE: PRT
<213> ORGANISM: Artificial Sequence
<220> FEATURE:
<223> OTHER INFORMATION: ID immunogen ID2
<220> FEATURE:
<221> NAME/KEY: MISC_FEATURE
<223> OTHER INFORMATION: ID immunogen ID2

<400> SEQUENCE: 57

Val Pro Val Trp Lys Asp Ala Asp Thr Thr Leu Phe Cys Ala Ser Asp
 1               5                  10                  15

Ala Lys Ala His Glu Thr Glu Cys His Asn Val Trp Ala Thr His Ala
                 20                  25                  30

Cys Val Pro Thr Asp Pro Asn Pro Gln Glu Ile His Leu Glu Asn Val
             35                  40                  45

Thr Glu Asn Phe Asn Met Trp Lys Asn Met Val Glu Gln Met Gln
 50                  55                  60

Glu Asp Val Ile Ser Leu Trp Asp Gln Cys Leu Gln Pro Gly Gly Ala
 65                  70                  75                  80

Pro Lys Ile Ser Phe Asp Pro Ile Pro Ile His Tyr Cys Thr Pro Ala
                 85                  90                  95

Gly Tyr Val Ile Leu Lys Cys Asn Asp Lys Asn Phe Asn Gly Thr Gly
            100                 105                 110

Pro Cys Lys Asn Val Ser Ser Val Gln Cys Thr His Gly Ile Lys Pro
            115                 120                 125

Val Val Ser Ser Gly Gly Gly Asn Ile Lys Asp Asn Trp Arg Ser Glu
            130                 135                 140

Leu Tyr Lys Tyr Lys Val Val Gln Ile Glu
145                 150

<210> SEQ ID NO 58
<211> LENGTH: 158
<212> TYPE: PRT
<213> ORGANISM: Human immunodeficiency virus type 1
<220> FEATURE:
<221> NAME/KEY: MISC_FEATURE
<223> OTHER INFORMATION: gp120 from HIV-1 strain 93TH057
```

-continued

```
<400> SEQUENCE: 58

Val Trp Lys Asp Ala Asp Thr Thr Leu Phe Cys Ala Ser Asp Ala Lys
1               5                   10                  15

Ala His Glu Thr Glu Val His Asn Val Trp Ala Thr His Ala Cys Val
            20                  25                  30

Pro Thr Asp Pro Asn Pro Gln Glu Ile His Leu Glu Asn Val Thr Glu
        35                  40                  45

Asn Phe Asn Met Trp Lys Asn Asn Met Val Glu Gln Met Gln Glu Asp
    50                  55                  60

Val Ile Ser Leu Trp Asp Gln Ser Leu Gln Pro Cys Val Lys Leu Thr
65                  70                  75                  80

Ser Val Ile Lys Gln Ala Cys Pro Lys Ile Ser Phe Asp Pro Ile Pro
                85                  90                  95

Ile His Tyr Cys Thr Pro Ala Gly Tyr Val Ile Leu Lys Cys Asn Asp
            100                 105                 110

Lys Asn Phe Asn Gly Thr Gly Pro Cys Lys Asn Val Ser Ser Val Gln
        115                 120                 125

Cys Thr His Gly Ile Lys Pro Val Val Ser Gly Asn Ile Lys Asp Asn
    130                 135                 140

Trp Arg Ser Glu Leu Tyr Lys Tyr Lys Val Val Gln Ile Glu
145                 150                 155

<210> SEQ ID NO 59
<211> LENGTH: 159
<212> TYPE: PRT
<213> ORGANISM: Human immunodeficiency virus type 1
<220> FEATURE:
<221> NAME/KEY: MISC_FEATURE
<223> OTHER INFORMATION: gp120 from HIV-1 strain 89.6P

<400> SEQUENCE: 59

Val Trp Lys Glu Ala Thr Thr Thr Leu Phe Cys Ala Ser Asp Ala Lys
1               5                   10                  15

Ala Tyr Asp Thr Glu Val His Asn Val Trp Ala Thr His Ala Cys Val
            20                  25                  30

Pro Thr Asp Pro Asn Pro Gln Glu Val Val Leu Gly Asn Val Thr Glu
        35                  40                  45

Asn Phe Asn Met Trp Lys Asn Asn Met Val Asp Gln Met His Glu Asp
    50                  55                  60

Ile Ile Ser Leu Trp Asp Glu Ser Leu Gln Pro Cys Val Lys Leu Thr
65                  70                  75                  80

Ser Val Ile Lys Gln Ala Cys Pro Lys Val Ser Phe Asp Pro Ile Pro
                85                  90                  95

Ile His Tyr Cys Val Pro Ala Gly Phe Ala Met Leu Lys Cys Asn Asn
            100                 105                 110

Lys Thr Phe Asn Gly Ser Gly Pro Cys Thr Asn Val Ser Thr Val Gln
        115                 120                 125

Cys Thr His Gly Ile Arg Pro Val Val Ser Gly Asp Met Lys Arg Asp
    130                 135                 140

Asn Trp Arg Ser Glu Leu Tyr Lys Tyr Lys Val Val Lys Ile Glu
145                 150                 155

<210> SEQ ID NO 60
<211> LENGTH: 173
<212> TYPE: PRT
<213> ORGANISM: Artificial Sequence
<220> FEATURE:
```

```
<223> OTHER INFORMATION: Consensus sequence of ID immunogens lacking
      V1V2 region (clades)
<220> FEATURE:
<221> NAME/KEY: MISC_FEATURE
<222> LOCATION: (3)..(3)
<223> OTHER INFORMATION: Xaa is V or A
<220> FEATURE:
<221> NAME/KEY: MISC_FEATURE
<222> LOCATION: (5)..(5)
<223> OTHER INFORMATION: Xaa is K, E or R
<220> FEATURE:
<221> NAME/KEY: MISC_FEATURE
<222> LOCATION: (6)..(6)
<223> OTHER INFORMATION: Xaa is D or E
<220> FEATURE:
<221> NAME/KEY: MISC_FEATURE
<222> LOCATION: (7)..(7)
<223> OTHER INFORMATION: Xaa is A or T
<220> FEATURE:
<221> NAME/KEY: MISC_FEATURE
<222> LOCATION: (8)..(8)
<223> OTHER INFORMATION: Xaa is E, D, T, K or N
<220> FEATURE:
<221> NAME/KEY: MISC_FEATURE
<222> LOCATION: (10)..(10)
<223> OTHER INFORMATION: Xaa is T or I
<220> FEATURE:
<221> NAME/KEY: MISC_FEATURE
<222> LOCATION: (11)..(11)
<223> OTHER INFORMATION: Xaa is L or P
<220> FEATURE:
<221> NAME/KEY: MISC_FEATURE
<222> LOCATION: (19)..(19)
<223> OTHER INFORMATION: Xaa is A or S
<220> FEATURE:
<221> NAME/KEY: MISC_FEATURE
<222> LOCATION: (20)..(20)
<223> OTHER INFORMATION: Xaa is Y or H
<220> FEATURE:
<221> NAME/KEY: MISC_FEATURE
<222> LOCATION: (21)..(21)
<223> OTHER INFORMATION: Xaa is E, D, K or S
<220> FEATURE:
<221> NAME/KEY: MISC_FEATURE
<222> LOCATION: (22)..(22)
<223> OTHER INFORMATION: Xaa is T, K, R or A
<220> FEATURE:
<221> NAME/KEY: MISC_FEATURE
<222> LOCATION: (27)..(27)
<223> OTHER INFORMATION: Xaa is V or I
<220> FEATURE:
<221> NAME/KEY: MISC_FEATURE
<222> LOCATION: (31)..(31)
<223> OTHER INFORMATION: Xaa is H or Y
<220> FEATURE:
<221> NAME/KEY: MISC_FEATURE
<222> LOCATION: (39)..(39)
<223> OTHER INFORMATION: Xaa is N or S
<220> FEATURE:
<221> NAME/KEY: MISC_FEATURE
<222> LOCATION: (43)..(43)
<223> OTHER INFORMATION: Xaa is I, V, L or M
<220> FEATURE:
<221> NAME/KEY: MISC_FEATURE
<222> LOCATION: (44)..(44)
<223> OTHER INFORMATION: Xaa is H, N, V, E, T, P, A or D
<220> FEATURE:
<221> NAME/KEY: MISC_FEATURE
<222> LOCATION: (45)..(45)
<223> OTHER INFORMATION: Xaa is L or M
<220> FEATURE:
<221> NAME/KEY: MISC_FEATURE
<222> LOCATION: (46)..(46)
<223> OTHER INFORMATION: Xaa is E, G or K
<220> FEATURE:
<221> NAME/KEY: MISC_FEATURE
<222> LOCATION: (51)..(51)
<223> OTHER INFORMATION: Xaa is E, D or N
<220> FEATURE:
```

```
<221> NAME/KEY: MISC_FEATURE
<222> LOCATION: (53)..(53)
<223> OTHER INFORMATION: Xaa is N or D
<220> FEATURE:
<221> NAME/KEY: MISC_FEATURE
<222> LOCATION: (55)..(55)
<223> OTHER INFORMATION: Xaa is W or G
<220> FEATURE:
<221> NAME/KEY: MISC_FEATURE
<222> LOCATION: (56)..(56)
<223> OTHER INFORMATION: Xaa is K, E or N
<220> FEATURE:
<221> NAME/KEY: MISC_FEATURE
<222> LOCATION: (58)..(58)
<223> OTHER INFORMATION: Xaa is N, D, H or G
<220> FEATURE:
<221> NAME/KEY: MISC_FEATURE
<222> LOCATION: (61)..(61)
<223> OTHER INFORMATION: Xaa is E, D or N
<220> FEATURE:
<221> NAME/KEY: MISC_FEATURE
<222> LOCATION: (64)..(64)
<223> OTHER INFORMATION: Xaa is H or Q
<220> FEATURE:
<221> NAME/KEY: MISC_FEATURE
<222> LOCATION: (65)..(65)
<223> OTHER INFORMATION: Xaa is T or E
<220> FEATURE:
<221> NAME/KEY: MISC_FEATURE
<222> LOCATION: (67)..(67)
<223> OTHER INFORMATION: Xaa is I or V
<220> FEATURE:
<221> NAME/KEY: MISC_FEATURE
<222> LOCATION: (73)..(73)
<223> OTHER INFORMATION: Xaa is Q or E
<220> FEATURE:
<221> NAME/KEY: MISC_FEATURE
<222> LOCATION: (83)..(83)
<223> OTHER INFORMATION: Xaa is V or I
<220> FEATURE:
<221> NAME/KEY: MISC_FEATURE
<222> LOCATION: (84)..(84)
<223> OTHER INFORMATION: Xaa is S or T
<220> FEATURE:
<221> NAME/KEY: MISC_FEATURE
<222> LOCATION: (85)..(85)
<223> OTHER INFORMATION: Xaa is F or W
<220> FEATURE:
<221> NAME/KEY: MISC_FEATURE
<222> LOCATION: (86)..(86)
<223> OTHER INFORMATION: Xaa is E, D or T
<220> FEATURE:
<221> NAME/KEY: MISC_FEATURE
<222> LOCATION: (94)..(94)
<223> OTHER INFORMATION: Xaa is A or T
<220> FEATURE:
<221> NAME/KEY: MISC_FEATURE
<222> LOCATION: (98)..(98)
<223> OTHER INFORMATION: Xaa is F or Y
<220> FEATURE:
<221> NAME/KEY: MISC_FEATURE
<222> LOCATION: (99)..(99)
<223> OTHER INFORMATION: Xaa is A or V
<220> FEATURE:
<221> NAME/KEY: MISC_FEATURE
<222> LOCATION: (104)..(104)
<223> OTHER INFORMATION: Xaa is K, N or R
<220> FEATURE:
<221> NAME/KEY: MISC_FEATURE
<222> LOCATION: (105)..(105)
<223> OTHER INFORMATION: Xaa is D or N
<220> FEATURE:
<221> NAME/KEY: MISC_FEATURE
<222> LOCATION: (106)..(106)
<223> OTHER INFORMATION: Xaa is K or P
<220> FEATURE:
<221> NAME/KEY: MISC_FEATURE
<222> LOCATION: (107)..(107)
<223> OTHER INFORMATION: Xaa is E, R, K, T or N
```

```
<220> FEATURE:
<221> NAME/KEY: MISC_FEATURE
<222> LOCATION: (109)..(109)
<223> OTHER INFORMATION: Xaa is N or T
<220> FEATURE:
<221> NAME/KEY: MISC_FEATURE
<222> LOCATION: (111)..(111)
<223> OTHER INFORMATION: Xaa is T or L
<220> FEATURE:
<221> NAME/KEY: MISC_FEATURE
<222> LOCATION: (113)..(113)
<223> OTHER INFORMATION: Xaa is P, L, S or Q
<220> FEATURE:
<221> NAME/KEY: MISC_FEATURE
<222> LOCATION: (115)..(115)
<223> OTHER INFORMATION: Xaa is K, N, T, R or H
<220> FEATURE:
<221> NAME/KEY: MISC_FEATURE
<222> LOCATION: (119)..(119)
<223> OTHER INFORMATION: Xaa is T or S
<220> FEATURE:
<221> NAME/KEY: MISC_FEATURE
<222> LOCATION: (127)..(127)
<223> OTHER INFORMATION: Xaa is K or R
<220> FEATURE:
<221> NAME/KEY: MISC_FEATURE
<222> LOCATION: (130)..(130)
<223> OTHER INFORMATION: Xaa is V or A
<220> FEATURE:
<221> NAME/KEY: MISC_FEATURE
<222> LOCATION: (133)..(133)
<223> OTHER INFORMATION: Xaa is T or G
<220> FEATURE:
<221> NAME/KEY: MISC_FEATURE
<222> LOCATION: (136)..(136)
<223> OTHER INFORMATION: Xaa is D or N
<220> FEATURE:
<221> NAME/KEY: MISC_FEATURE
<222> LOCATION: (137)..(137)
<223> OTHER INFORMATION: Xaa is M or I
<220> FEATURE:
<221> NAME/KEY: MISC_FEATURE
<222> LOCATION: (138)..(138)
<223> OTHER INFORMATION: Xaa is K or R
<220> FEATURE:
<221> NAME/KEY: MISC_FEATURE
<222> LOCATION: (139)..(139)
<223> OTHER INFORMATION: Xaa is D or N
<220> FEATURE:
<221> NAME/KEY: MISC_FEATURE
<222> LOCATION: (143)..(143)
<223> OTHER INFORMATION: Xaa is S or N
<220> FEATURE:
<221> NAME/KEY: MISC_FEATURE
<222> LOCATION: (150)..(150)
<223> OTHER INFORMATION: Xaa is V or I
<220> FEATURE:
<221> NAME/KEY: MISC_FEATURE
<222> LOCATION: (152)..(152)
<223> OTHER INFORMATION: Xaa is K, E or Q
<220> FEATURE:
<221> NAME/KEY: MISC_FEATURE
<222> LOCATION: (154)..(154)
<223> OTHER INFORMATION: Xaa is E or K
<220> FEATURE:
<221> NAME/KEY: MISC_FEATURE
<222> LOCATION: (156)..(156)
<223> OTHER INFORMATION: Xaa is L or V
<220> FEATURE:
<221> NAME/KEY: MISC_FEATURE
<222> LOCATION: (158)..(158)
<223> OTHER INFORMATION: Xaa is V, I or L
<220> FEATURE:
<221> NAME/KEY: MISC_FEATURE
<222> LOCATION: (162)..(162)
<223> OTHER INFORMATION: Xaa is R, K, E or A
<220> FEATURE:
<221> NAME/KEY: MISC_FEATURE
<222> LOCATION: (164)..(164)
```

```
<223> OTHER INFORMATION: Xaa is K or R
<220> FEATURE:
<221> NAME/KEY: MISC_FEATURE
<222> LOCATION: (166)..(166)
<223> OTHER INFORMATION: Xaa is R or Q
<220> FEATURE:
<221> NAME/KEY: MISC_FEATURE
<222> LOCATION: (169)..(169)
<223> OTHER INFORMATION: Xaa is E, Q, K or G
<220> FEATURE:
<221> NAME/KEY: MISC_FEATURE
<222> LOCATION: (172)..(172)
<223> OTHER INFORMATION: Xaa is K or R

<400> SEQUENCE: 60

Val Pro Xaa Trp Xaa Xaa Xaa Xaa Thr Xaa Xaa Phe Cys Ala Ser Asp
 1               5                  10                  15

Ala Lys Xaa Xaa Xaa Xaa Glu Cys His Asn Xaa Trp Ala Thr Xaa Ala
            20                  25                  30

Cys Val Pro Thr Asp Pro Xaa Pro Gln Glu Xaa Xaa Xaa Xaa Asn Val
        35                  40                  45

Thr Glu Xaa Phe Xaa Met Xaa Xaa Asn Xaa Met Val Xaa Gln Met Xaa
    50                  55                  60

Xaa Asp Xaa Ile Ser Leu Trp Asp Xaa Cys Leu Lys Pro Gly Gly Ala
65                  70                  75                  80

Pro Lys Xaa Xaa Xaa Xaa Pro Ile Pro Ile His Tyr Cys Xaa Pro Ala
                85                  90                  95

Gly Xaa Xaa Ile Leu Lys Cys Xaa Xaa Xaa Xaa Phe Xaa Gly Xaa Gly
            100                 105                 110

Xaa Cys Xaa Asn Val Ser Xaa Val Gln Cys Thr His Gly Ile Xaa Pro
        115                 120                 125

Val Xaa Ser Thr Xaa Gly Gly Xaa Xaa Xaa Asn Trp Arg Xaa Glu
    130                 135                 140

Leu Tyr Lys Tyr Lys Xaa Val Xaa Ile Xaa Pro Xaa Gly Xaa Ala Pro
145                 150                 155                 160

Thr Xaa Ala Xaa Arg Xaa Val Val Xaa Arg Glu Xaa Arg
                165                 170

<210> SEQ ID NO 61
<211> LENGTH: 173
<212> TYPE: PRT
<213> ORGANISM: Artificial Sequence
<220> FEATURE:
<223> OTHER INFORMATION: Consensus sequence of ID immunogens lacking
      V1V2 region (strains)
<220> FEATURE:
<221> NAME/KEY: MISC_FEATURE
<222> LOCATION: (5)..(5)
<223> OTHER INFORMATION: Xaa is R or K
<220> FEATURE:
<221> NAME/KEY: MISC_FEATURE
<222> LOCATION: (6)..(6)
<223> OTHER INFORMATION: Xaa is D or E
<220> FEATURE:
<221> NAME/KEY: MISC_FEATURE
<222> LOCATION: (8)..(8)
<223> OTHER INFORMATION: Xaa is E, T or K
<220> FEATURE:
<221> NAME/KEY: MISC_FEATURE
<222> LOCATION: (20)..(20)
<223> OTHER INFORMATION: Xaa is H or Y
<220> FEATURE:
<221> NAME/KEY: MISC_FEATURE
<222> LOCATION: (21)..(21)
<223> OTHER INFORMATION: Xaa is V, D or E
<220> FEATURE:
<221> NAME/KEY: MISC_FEATURE
```

-continued

```
<222> LOCATION: (22)..(22)
<223> OTHER INFORMATION: Xaa is G, A, T, R or K
<220> FEATURE:
<221> NAME/KEY: MISC_FEATURE
<222> LOCATION: (43)..(43)
<223> OTHER INFORMATION: Xaa is I, V or M
<220> FEATURE:
<221> NAME/KEY: MISC_FEATURE
<222> LOCATION: (44)..(44)
<223> OTHER INFORMATION: Xaa is H, S, K, V or A
<220> FEATURE:
<221> NAME/KEY: MISC_FEATURE
<222> LOCATION: (46)..(46)
<223> OTHER INFORMATION: Xaa is E or V
<220> FEATURE:
<221> NAME/KEY: MISC_FEATURE
<222> LOCATION: (51)..(51)
<223> OTHER INFORMATION: Xaa is N or D
<220> FEATURE:
<221> NAME/KEY: MISC_FEATURE
<222> LOCATION: (58)..(58)
<223> OTHER INFORMATION: Xaa is K, N or D
<220> FEATURE:
<221> NAME/KEY: MISC_FEATURE
<222> LOCATION: (60)..(60)
<223> OTHER INFORMATION: Xaa is A or V
<220> FEATURE:
<221> NAME/KEY: MISC_FEATURE
<222> LOCATION: (61)..(61)
<223> OTHER INFORMATION: Xaa is D, E or N
<220> FEATURE:
<221> NAME/KEY: MISC_FEATURE
<222> LOCATION: (64)..(64)
<223> OTHER INFORMATION: Xaa is Q or H
<220> FEATURE:
<221> NAME/KEY: MISC_FEATURE
<222> LOCATION: (65)..(65)
<223> OTHER INFORMATION: Xaa is E or V
<220> FEATURE:
<221> NAME/KEY: MISC_FEATURE
<222> LOCATION: (67)..(67)
<223> OTHER INFORMATION: Xaa is V or I
<220> FEATURE:
<221> NAME/KEY: MISC_FEATURE
<222> LOCATION: (83)..(83)
<223> OTHER INFORMATION: Xaa is V or I
<220> FEATURE:
<221> NAME/KEY: MISC_FEATURE
<222> LOCATION: (84)..(84)
<223> OTHER INFORMATION: Xaa is S, T or I
<220> FEATURE:
<221> NAME/KEY: MISC_FEATURE
<222> LOCATION: (86)..(86)
<223> OTHER INFORMATION: Xaa is D or E
<220> FEATURE:
<221> NAME/KEY: MISC_FEATURE
<222> LOCATION: (94)..(94)
<223> OTHER INFORMATION: Xaa is T or A
<220> FEATURE:
<221> NAME/KEY: MISC_FEATURE
<222> LOCATION: (98)..(98)
<223> OTHER INFORMATION: Xaa is F or Y
<220> FEATURE:
<221> NAME/KEY: MISC_FEATURE
<222> LOCATION: (105)..(105)
<223> OTHER INFORMATION: Xaa is D or N
<220> FEATURE:
<221> NAME/KEY: MISC_FEATURE
<222> LOCATION: (107)..(107)
<223> OTHER INFORMATION: Xaa is K or T
<220> FEATURE:
<221> NAME/KEY: MISC_FEATURE
<222> LOCATION: (115)..(115)
<223> OTHER INFORMATION: Xaa is K, T, N or R
<220> FEATURE:
<221> NAME/KEY: MISC_FEATURE
<222> LOCATION: (119)..(119)
<223> OTHER INFORMATION: Xaa is S or T
<220> FEATURE:
```

```
<221> NAME/KEY: MISC_FEATURE
<222> LOCATION: (127)..(127)
<223> OTHER INFORMATION: Xaa is K or R
<220> FEATURE:
<221> NAME/KEY: MISC_FEATURE
<222> LOCATION: (136)..(136)
<223> OTHER INFORMATION: Xaa is N or D
<220> FEATURE:
<221> NAME/KEY: MISC_FEATURE
<222> LOCATION: (137)..(137)
<223> OTHER INFORMATION: Xaa is I or M
<220> FEATURE:
<221> NAME/KEY: MISC_FEATURE
<222> LOCATION: (138)..(138)
<223> OTHER INFORMATION: Xaa is K or R
<220> FEATURE:
<221> NAME/KEY: MISC_FEATURE
<222> LOCATION: (152)..(152)
<223> OTHER INFORMATION: Xaa is E, K or Q
<220> FEATURE:
<221> NAME/KEY: MISC_FEATURE
<222> LOCATION: (153)..(153)
<223> OTHER INFORMATION: Xaa is I or L
<220> FEATURE:
<221> NAME/KEY: MISC_FEATURE
<222> LOCATION: (154)..(154)
<223> OTHER INFORMATION: Xaa is E or K
<220> FEATURE:
<221> NAME/KEY: MISC_FEATURE
<222> LOCATION: (158)..(158)
<223> OTHER INFORMATION: Xaa is I or V
<220> FEATURE:
<221> NAME/KEY: MISC_FEATURE
<222> LOCATION: (162)..(162)
<223> OTHER INFORMATION: Xaa is R, K or T
<220> FEATURE:
<221> NAME/KEY: MISC_FEATURE
<222> LOCATION: (164)..(164)
<223> OTHER INFORMATION: Xaa is K or R
<220> FEATURE:
<221> NAME/KEY: MISC_FEATURE
<222> LOCATION: (169)..(169)
<223> OTHER INFORMATION: Xaa is E, T or Q
<220> FEATURE:
<221> NAME/KEY: MISC_FEATURE
<222> LOCATION: (171)..(171)
<223> OTHER INFORMATION: Xaa is Q or E

<400> SEQUENCE: 61

Val Pro Val Trp Xaa Xaa Ala Xaa Thr Thr Leu Phe Cys Ala Ser Asp
 1               5                  10                  15

Ala Lys Ala Xaa Xaa Xaa Glu Cys His Asn Val Trp Ala Thr His Ala
            20                  25                  30

Cys Val Pro Thr Asp Pro Asn Pro Gln Glu Xaa Xaa Leu Xaa Asn Val
        35                  40                  45

Thr Glu Xaa Phe Asn Met Trp Lys Asn Xaa Met Xaa Xaa Gln Met Xaa
    50                  55                  60

Xaa Asp Xaa Ile Ser Leu Trp Asp Gln Cys Leu Lys Pro Gly Gly Ala
65                  70                  75                  80

Pro Lys Xaa Xaa Phe Xaa Pro Ile Pro Ile His Tyr Cys Xaa Pro Ala
                85                  90                  95

Gly Xaa Ala Ile Leu Lys Cys Asn Xaa Lys Xaa Phe Asn Gly Thr Gly
           100                 105                 110

Pro Cys Xaa Asn Val Ser Xaa Val Gln Cys Thr His Gly Ile Xaa Pro
       115                 120                 125

Val Val Ser Thr Gly Gly Xaa Xaa Xaa Asp Asn Trp Arg Ser Glu
   130                 135                 140
```

-continued

```
Leu Tyr Lys Tyr Lys Val Val Xaa Xaa Xaa Pro Leu Gly Xaa Ala Pro
145                 150                 155                 160

Thr Xaa Ala Xaa Arg Arg Val Val Xaa Arg Xaa Lys Arg
                165                 170
```

STABLE IMMUNOGEN BASED ON INNER DOMAIN OF HIV-1 GP120 FOR INDUCING IMMUNITY AGAINST HIV

BACKGROUND OF INVENTION

Fc receptor-dependent effector functions such as antibody-dependent cell-mediated cytotoxicity (ADCC) constitute an important bridge between innate and adaptive immunities to HIV-1 [1]. They trigger clearing of virus particles or virus-infected cells through mechanisms involving interactions of antibody constant (Fc) region and Fcγ receptors (FcγRs) on the surface of cells involved or potentially involved in HIV infection (natural killer cells (NKs), monocytes, macrophages, dendritic cells, and neutrophils) [2-4].

In contrast to broadly neutralizing antibody responses, which become detectable 2-4 years post-infection [5, 6], ADCC responses appear relatively early during acute infection [7, 8] and are detectable as early as 21 and 48 days after SIVmac251 [9-11] and acute HIV-1 [12] infection, respectively. These early ADCC responses, which in general are broadly reactive, precede the appearance of neutralizing antibody responses with similar breadth [13, 14]. ADCC ultimately leads to the target cell being killed by an effector cell, decreasing the probability of cell-to-cell transmission.

Considerable evidence supports a role of ADCC in preventing or modulating HIV-1 infection. ADCC responses in chronically HIV-1 infected individuals were shown to correlate with slower progression of HIV [15-18] or decreased virus replication [19]. HIV-specific antibodies capable of inducing ADCC and therefore important and serve to protect, for example, against infection in mother-to-infant transmission [20].

Another Fc-mediated effector function, antibody-dependent cell-mediated viral inhibition (ADCVI) coupled with the low-affinity IgG receptor CD16 (FcγRIIIa) genotype, correlated with protection against HIV-1 transmission in a subset of volunteers in the Vax004 vaccine efficacy trial [21]. The picture is even stronger for non-human primate (NHP) infections where sustained ADCC responses predict delayed disease in SIV/SHIV infection [22, 23] and ADCC activity correlates with vaccine-induced protection, often in the absence of neutralizing antibodies [6, 10, 24-28]. Passive immunization studies using a variant of the neutralizing monoclonal antibody, b12, that lacks full Fc receptor binding function but fully retains neutralization potency, resulted in reduced protection against SHIV challenge acquisition [29, 30]. To this end, the latest report on the protective effect of vaginal application of neutralizing and non-neutralizing antibodies against vaginal $SHIV_{162p3}$ challenge acquisition [31] clearly indicated that mAbs capable of Fc-dependent function provide post-infection control of the SHIV challenge virus, leading to in vivo anti-HIV effects that may strengthen those elicited by neutralizing mAbs.

With regard to vaccine-induced protection in humans, the recent vaccination strategy tested in the ALVACHIV/AIDS-VAXB/E RV144 vaccine trial, which showed an estimated vaccine efficacy of 31.2% in preventing HIV-1 acquisition, is of particular importance [32]. It proved, for the first time, that vaccination can protect humans from HIV-1 infection, and that protection could be due to the generation of a blend of neutralizing and non-neutralizing antibody responses with the presence of very modest CD4 T cell responses [32, 33].

The RV144 immunization regimen selectively induced non-neutralizing IgG3 responses which showed highly coordinated Fc-mediated effector responses [34, 35]. These responses correlated with decreased risk of HIV-1 infection in a blinded follow-up case control study [34]. The array of mAbs elicited in RV144 trial was narrow with specificities for the second variable (V2) loop region [33] as well as CD4-inducible epitopes within the first and second constant (C1/C2) domain of gp120 [36]. Whereas V2-specific mAbs were suggested to act through both direct neutralization and Fc-mediated effector function [37, 38], the C1/C2-region specific mAbs were non-neutralizing and capable of potent ADCC [39]. Most importantly, ADCC emerged as a potential correlate of protection in secondary analyses in the subset vaccinated subjects with low plasma anti-HIV-1 Env IgA titers [40]. These studies clearly indicated that RV144 vaccine induced broadly reactive ADCC responses to the C1/C2 domain and that these responses might be partially responsible for the protection observed.

Together, this data suggests an intriguing link between vaccine-mediated protection and ADCC, and provides the first evidence that ADCC might contribute to HIV-1 vaccine efficacy in humans. A role for Fc-mediated effector function in protective immunity against HIV-1 is also indicated. Studies also point toward non-neutralizing, conformational epitopes in the C1/C2 region as important players in these responses (reviewed in [47, 50, 51]). It is well established that this transitional epitope region becomes exposed on the virion spike only upon binding to the CD4 receptor post-infection [48, 49, 52, 53]. In addition, binding to CD4 significantly enhances its exposure in context of monomeric full length gp120 [44]. The fact that the ADCC responses were directed to these transitional CD4-induced epitopes in the RV144 trial consisting of immunization regiment of ALVACHIV vCP1521 prime and recombinant clade B/E monomeric gp120 boost confirms high immunogenicity of this region.

Protein immunogens based on the C1/C2 region of gp120 that have the ability to induce non-neutralizing antibody responses along with Fc-mediated effector responses could serve as effective components of HIV-1 vaccines. The present invention is directed to the elucidation of such peptides as well as other important goals.

BRIEF SUMMARY OF INVENTION

Provided herein are stable protein immunogens that comprise portions of the inner domain of the Human Immunodeficiency Virus (HIV-1) gp120 protein. These inner domain immunogens can be used to vaccinate subjects against infection with HIV, the causative agent of Acquired Immunodeficiency Syndrome (AIDS). The ID immunogens can also be used as targets in screening to identify small molecule or peptide inhibitors that block HIV-1 viral entry and attachment steps (e.g., for therapeutic or research use). The ID immunogens can further be used as probes for identifying gp120 first and second constant (C1/C2) region (or C1/C2 and V1V2 combined)-specific antibodies (such as monoclonal antibodies; mAbs), e.g., for use in ELISA, C1/C2 binding titer assays, and the like, and for clinical diagnostic or research applications.

The ID immunogens contain C1/C2-specific (or C1/C2 and V1V2 combined) gp120 epitopes that are occluded in the native Env trimer of most HIV-1 isolates and only become exposed on the target cell surface during viral entry after Env trimers engage CD4 of the target cell. Importantly, the C1/C2 epitopes also persist on freshly infected cell surfaces for extended periods of time post-infection where they become excellent targets for Fc-mediated effector activity. These epitopes, marked by mAb A32 (A32-like epitopes), show poor immunogenicity in conventional gp120-based vaccines. The ID immunogens selectively present these CD4-inducible epitopes (CD4i epitopes) within a minimal structural unit of gp120. As compared to unliganded gp120, the ID immunogens stably present CD4i epitopes within the C1/C2 gp120 region and they are ideal vaccine candidates for stimulating a non-neutralizing Fc-mediated effector function antibody response to the C1/C2 region.

C1/C2 epitopes of gp120 have been implicated as targets for antibodies mediating antibody-dependent cellular cytotoxicity (ADCC) that correlate with reduced HIV infection risk in a subset of vaccinated subjects. Utilization of the novel immunogens in vivo in a vaccination regimen allows selective elicitation of non-neutralizing Fc-mediated response to the C1/C2 region (or both C1/C2 and V1V2 regions) without the complication of neutralization epitopes. In addition, vaccination approaches with the ID immunogens will help overcome the major obstacle of passive immunization studies with antibodies acting through Fc-mediated effector function and relating to overdosing and an apparent prozone effect. It will allow evaluation of the protective spectrum of elicited non-neutralizing antibodies that mediate the Fc-mediated effector function in vaccine settings.

Each of the ID immunogens of the invention is based on a mature HIV-1 gp120 polypeptide sequence, but lacks selected domains and includes particular amino acid changes. The mature gp120-based ID immunogens are thus further characterized by two or more of the following features:

(i) deletion of a portion of the N-terminus of the protein (generally corresponding to residues 1-11 of gp120 from the HIV-1 isolate HXBc2 set forth in SEQ ID NO:1);

(ii) engineered cysteines at positions 65 and 115 corresponding to the sequence of the HXBc2 isolate, which leads to stabilization of the immunogen in a CD4-bound conformation upon disulfide bond formation between the cysteines ($C_{65}$-$C_{115}$);

(iii) deletion of the outer domain region of the protein (generally corresponding to amino acids 258-472 of the HXBc2 isolate) and replacement by a GlyGly dipeptide linker; and (iv) deletion of the V1V2 loop of the protein (generally corresponding to amino acids 119-205 of the HXBc2 isolate) and replacement by a GlyGlyAla tripeptide linker.

As used herein, mature gp120 refers to gp120 polypeptide lacking the signal peptide (e.g., residues 1-30 of the sequence of full-length gp120 from the HIV-1 isolate HXBc2 shown in SEQ ID NO:2; the sequence of mature gp120 from HXBc2 is provided in SEQ ID NO:1).

Thus, and in a first embodiment, the invention is directed to a HIV-1 gp120 inner domain (ID) immunogen, where the ID immunogen comprises:

(a) a mature HIV-1 gp120 polypeptide having two or more of the features (i)-(iv):
  (i) deletion of amino acids 1-11 of the N-terminus,
  (ii) cysteine residues at amino acid positions 65 and 115,
  (iii) deletion of amino acids 258-472 of the outer domain region and replacement by a GlyGly dipeptide linker, and
  (iv) deletion of amino acids 119-205 of the V1V2 loop and replacement by a GlyGlyAla tripeptide linker, wherein the amino acid numbering corresponds to the amino acid sequence set forth in SEQ ID NO:1; or (b) a variant having at least about 95% sequence identity with an immunogen of (a) over the entire length of the immunogen sequence SEQ ID NO:1 is the amino acid sequence of mature gp120 from the HIV-1 isolate HXB c2.

In certain aspects, the ID immunogen of (a) has three or more of the features (i)-(iv). In other certain aspects, the ID immunogen of (a) has features (i)-(iii). In still further aspects, the ID immunogen of (a) has features (i)-(iv).

In non-limiting examples, the ID immunogen comprises an amino acid sequence set forth in any one of SEQ ID NOs:3-54 or a variant thereof having at least about 95% sequence identity with the immunogen over the entire length of the immunogen sequence In certain aspects, the ID immunogens have a $C_{65}$-$C_{115}$ disulfide bond.

In certain aspects, the variants have the property of inducing Fc-mediated humoral response to C1/C2 or combined C1/C2 and V1/V2 regions of HIV-1 gp120.

In a second embodiment, the invention is directed to an immunogenic composition comprising one or more ID immunogens as defined herein, and a pharmaceutically-acceptable carrier or diluent.

The immunogenic compositions of the invention can be comprised of only one specific ID immunogen, or two or more different ID immunogens (i.e., ID immunogens having different amino acid sequences). In a non-limiting example, the immunogenic composition comprises one or more of the ID immunogens set forth in SEQ ID NOs:3-54 or variants thereof, or both.

In a third embodiment, the invention is directed to a method of inducing an immune response to an ID immunogen in a subject, comprising administering to a subject an immunogenic amount of an immunogenic composition as defined herein, thereby inducing an immune response in the subject.

As indicated above, the immunogenic compositions of the invention can be comprised of only one specific ID immunogen, or two or more different ID immunogens (i.e., ID immunogens having different amino acid sequences). In a non-limiting example, the immunogenic composition comprises one or more of the ID immunogens set forth in SEQ ID NOs:3-54 or variants thereof, or both.

In a fourth embodiment, the invention is directed to a method of vaccinating a subject with a protective antigen, comprising administering to a subject in need thereof an effective amount of an immunogenic composition as defined herein, thereby vaccinating a subject with a protective antigen.

As indicated above, the immunogenic compositions of the invention can be comprised of only one specific ID immunogen, or two or more different ID immunogens (i.e., ID immunogens having different amino acid sequences). In a non-limiting example, the immunogenic composition comprises one or more of the ID immunogens set forth in SEQ ID NOs:3-54 or variants thereof, or both.

In a fifth embodiment, the invention is directed to a method of screening for antibodies with binding affinity for the C1/C2 region HIV-1 gp120, comprising:

(a) contacting an ID immunogen as defined herein with a test antibody, and (b) detecting binding of the ID immunogen by the test antibody.

Because antibodies can recognize and bind different antigens having similar sequences, the method of this embodiment can be conducted using one specific ID immunogen, or two or more different ID immunogens (i.e., ID immunogens having different amino acid sequences). In a non-limiting example, the ID immunogen is one or more of the ID immunogens set forth in SEQ ID NOs:3-54 or variants thereof, or both.

In some aspects of this embodiment, the antibody is one or more selected from a monoclonal antibody, a chimeric antibody, a humanized antibody, a human antibody, a single chain antibody (scFv), an Fab fragment, an F(ab')2 fragment, a multi-specific antibody, and a disulfide-linked antibody.

In some aspects of this embodiment, binding of the ID immunogen by the test antibody is detecting using an immunoassay, such as ELISA.

In a sixth embodiment, the invention is directed to a method of screening for inhibitors of HIV-1 viral attachment comprising:

(a) contacting an ID immunogen as defined herein with a test molecule, and (b) detecting binding of the ID immunogen by the test molecule.

The method of this embodiment can be conducted using one specific ID immunogen, or two or more different ID immunogens (i.e., ID immunogens having different amino acid sequences). In a non-limiting example, the ID immunogen is one or more of the ID immunogens set forth in SEQ ID NOs:3-54 or variants thereof, or both.

The test molecule may be any molecule that binds to an ID immunogen, such as an antibody or some other protein, peptide, nucleic acid, carbohydrate, lipid, fatty acid, small drug molecule, etc. After being identified as having binding affinity for an ID immunogen, the test molecule can be further screened to determine with the test molecule can interferes with the association of Env proteins displayed by HIV-1 and cell surface receptors. If this association can be inhibited or blocked, HIV-1 viral attachment and/or entry can be inhibited or blocked.

In some aspects of this embodiment, binding of the ID immunogen by the test molecule is detecting using an immunoassay such as ELISA.

The foregoing has outlined rather broadly the features and technical advantages of the present invention in order that the detailed description of the invention that follows may be better understood. Additional features and advantages of the invention will be described herein, which form the subject of the claims of the invention. It should be appreciated by those skilled in the art that any conception and specific embodiment disclosed herein may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that any description, figure, example, etc. is provided for the purpose of illustration and description only and is by no means intended to define the limits the invention.

BRIEF DESCRIPTION OF DRAWINGS

FIG. 1. Amino acid sequence alignment of ID immunogens based the consensus sequences of HIV-1 gp120 proteins from HIV-1 clades A1 (SEQ ID NO:3), A2 (SEQ ID NO:4), B (SEQ ID NO:5), C (SEQ ID NO:6), D (SEQ ID NO:7), F1 (SEQ ID NO:8), F2 (SEQ ID NO:9), G (SEQ ID NO:10), H (SEQ ID NO:11), 01_AE (SEQ ID NO:12), 02_AG (SEQ ID NO:13), 03_AB (SEQ ID NO:14), 04_CPX (SEQ ID NO:15), 06_CPX (SEQ ID NO:16), 08_BC (SEQ ID NO:17), 10_CD (SEQ ID NO:18), 11_CPX (SEQ ID NO:19), 12_BF (SEQ ID NO:20), 14_BG (SEQ ID NO:21). The entry termed "CON_OF_CONS_V1V2" (SEQ ID NO:22) is an ID immunogen based on a consensus sequence of the other HIV-1 clade consensus sequences. Each of the immunogens comprises the V1V2 region of the protein.

FIG. 2. Amino acid sequence alignment of ID immunogens based on the sequences of HIV-1 gp120 proteins from particular HIV-1 strains AB097872 (SEQ ID NO:23), AB052867 (SEQ ID NO:24), YU2 (SEQ ID NO:25), HXBc2 (SEQ ID NO:26), HM623558 (SEQ ID NO:27) and DQ404010 (SEQ ID NO:28). Each of the immunogens comprises the V1V2 region of the protein.

FIG. 3. Amino acid sequence alignment of ID immunogens based on HIV-1 gp120 proteins from HIV-1 clades A1 (SEQ ID NO:3), A2 (SEQ ID NO:4), B (SEQ ID NO:5), C (SEQ ID NO:6), D (SEQ ID NO:7), F1 (SEQ ID NO:8), F2 (SEQ ID NO:9), G (SEQ ID NO:10), H (SEQ ID NO:11), 01_AE (SEQ ID NO:12), 02_AG (SEQ ID NO:13), 03_AB (SEQ ID NO:14), 04_CPX (SEQ ID NO:15), 06_CPX (SEQ ID NO:16), 08_BC (SEQ ID NO:17), 10_CD (SEQ ID NO:18), 11_CPX (SEQ ID NO:19), 12_BF (SEQ ID NO:20), 14_BG (SEQ ID NO:21), and CON_OF_CONS_V1V2 (SEQ ID NO:22), and strains AB097872 (SEQ ID NO:23), AB052867 (SEQ ID NO:24), YU2 (SEQ ID NO:25), HXBc2 (SEQ ID NO:26), HM623558 (SEQ ID NO:27) and DQ404010 (SEQ ID NO:28). Each of the immunogens comprises the V1V2 region of the protein.

FIG. 4. Amino acid sequence alignment of ID immunogens based on the consensus sequences of HIV-1 gp120 proteins from HIV-1 clades A1 (SEQ ID NO:29), A2 (SEQ ID NO:30), B (SEQ ID NO:31), C (SEQ ID NO:32), D (SEQ ID NO:33), F1 (SEQ ID NO:34), F2 (SEQ ID NO:35), G (SEQ ID NO:36), H (SEQ ID NO:37), 01_AE (SEQ ID NO:38), 02_AG (SEQ ID NO:39), 03_AB (SEQ ID NO:40), 04_CPX (SEQ ID NO:41), 06_CPX (SEQ ID NO:42), 08_BC (SEQ ID NO:43), 10_CD (SEQ ID NO:44), 11_CPX (SEQ ID NO:45), 12_BF (SEQ ID NO:46), and 14_BG (SEQ ID NO:47). The entry termed "CON_OF_CONS" (SEQ ID NO:48) is an ID immunogen based on a consensus sequence of the other HIV-1 clade consensus sequences. The V1V2 region in each of the immunogens is replaced by the GGA trimer.

FIG. 5. Amino acid sequence alignment of ID immunogens based on the sequences of HIV-1 gp120 proteins from particular HIV-1 strains AB097872 (SEQ ID NO:49), AB052867 (SEQ ID NO:50), YU2 (SEQ ID NO:51), HXBc2 (SEQ ID NO:52), HM623558 (SEQ ID NO:53) and DQ404010 (SEQ ID NO:54). The V1V2 region in each of the immunogens is replaced by the GGA trimer.

FIG. 6. Amino acid sequence alignment of ID immunogens based on HIV-1 gp120 proteins from HIV-1 clades clades A1 (SEQ ID NO:29), A2 (SEQ ID NO:30), B (SEQ ID NO:31), C (SEQ ID NO:32), D (SEQ ID NO:33), F1 (SEQ ID NO:34), F2 (SEQ ID NO:35), G (SEQ ID NO:36), H (SEQ ID NO:37), 01_AE (SEQ ID NO:38), 02_AG (SEQ ID NO:39), 03_AB (SEQ ID NO:40), 04_CPX (SEQ ID NO:41), 06_CPX (SEQ ID NO:42), 08_BC (SEQ ID NO:43), 10_CD (SEQ ID NO:44), 11_CPX (SEQ ID NO:45), 12_BF (SEQ ID NO:46), 14_BG (SEQ ID NO:47)

and CON_OF_CONS (SEQ ID NO:48), and strains AB097872 (SEQ ID NO:49), AB052867 (SEQ ID NO:50), YU2 (SEQ ID NO:51), HXBc2 (SEQ ID NO:52), HM623558 (SEQ ID NO:53) and DQ404010 (SEQ ID NO:54). The V1V2 region in each of the immunogens is replaced by the GGA trimer.

Figure 7:
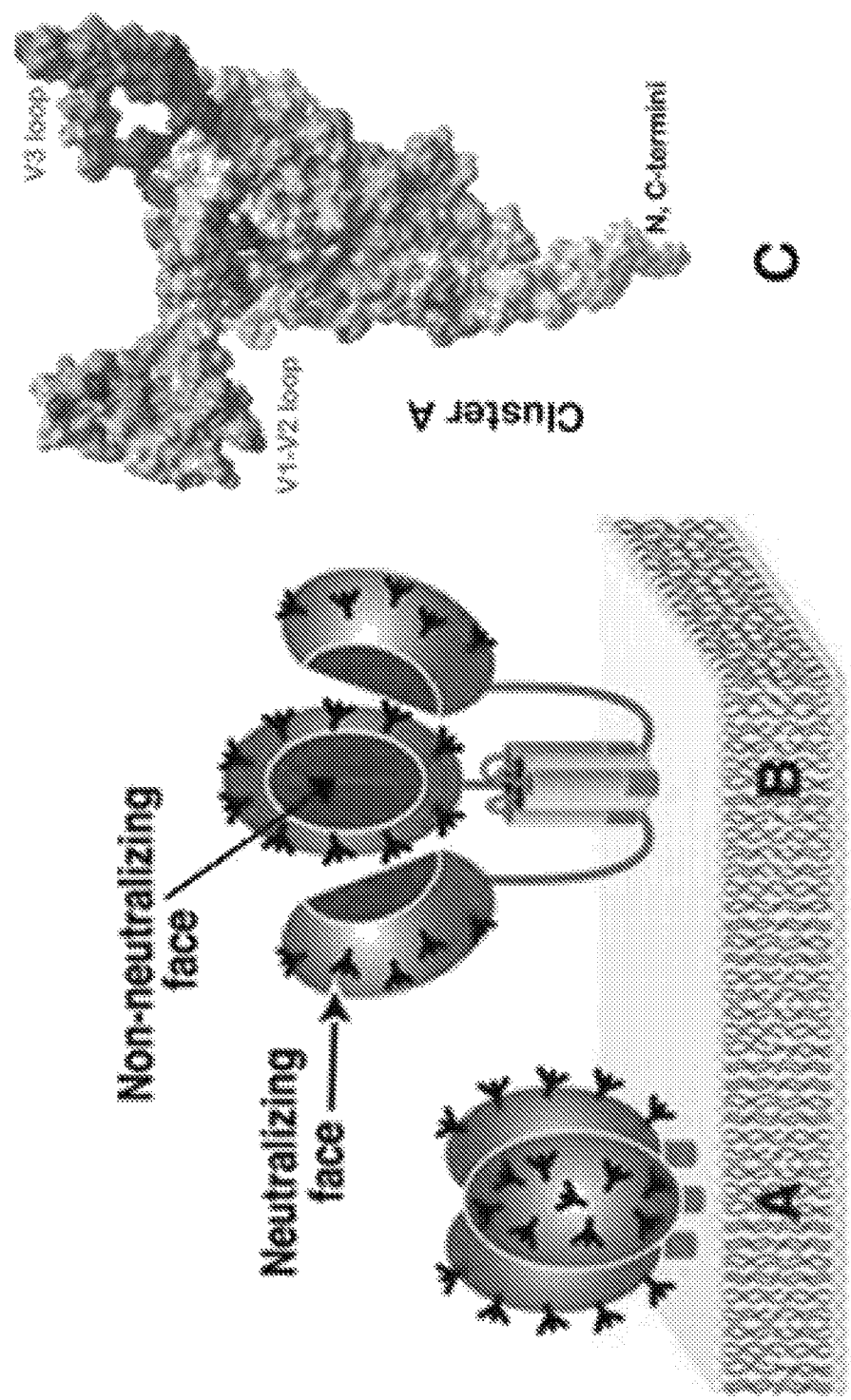

FIG. 7. Co-localization of Cluster A epitopes within Env trimer and monomeric gp120. (A) and (B) show Cluster A epitopes are associated with the so-called non-neutralizing face of Env [76] which is partially occluded by gp41 in the oligomer and buried within the unliganded Env trimer. gp120 is shown as oval shapes, with the outer neutralizing face in light shading and the inner nonneutralizing face in darker shading. Carbohydrate moieties are depicted as tree-like structures. gp41 is comprised of N-terminal and C-terminal transmembrane domains, depicted as tubes. The membrane-proximal gp41 region exposed on the trimer is shown as the darker shaped portion of the tubes. The figure is adapted from [76]. (C) shows colocalization of Cluster A epitopes (highlighted with darker shading) within the full-length gp120 monomer displayed with nonneutralizing face up. Cluster A epitopes are associated with the region proximal to the N, C termini of gp120. The figure is adapted from [44].

FIG. 8. Relative potencies of mAb groups in the bound virion ADCC assay.

FIG. 9. Low-dose heterologous SHIV(162P3) challenge studies with rhFLSC. Six male rhesus macaques per group were immunized with 300 μg of rhFLSC formulated with RC529SE or Iscomatrix adjuvant at 0, 4, 24 and 59 weeks. Four weeks after last boost animals were challenged weekly with 50 $TCID_{50}$ $SHIV_{162p3}$. Unimmunized naïve animals served as controls. (A) shows acquisition plots of all experimental groups. (B) shows the correlation between the numbers of intrarectal challenges required to infect and ADCC $EC_{50}$ titer. All animals immunized with rhFLSC are included. (C) shows acquisition plots for N12i2 competitive titers. (D) shows acquisition plots for competitive titers to A32 epitope. The correlations are shown for animals with IL2 ELISPOT counts above the mean. Figure from adopted from [81].

FIG. 10. Crystal structures of mAb N5i5, N60i3, JR4 and 2.2c bound to sCD4-triggered gp120 cores. The electrostatic potential displayed at the molecular surfaces of gp120 (right).

FIGS. 11A-11C. Definition of Cluster A epitopes within the Env antigen. FIG. 11A shows epitope footprints. The Cα atoms of the gp120 residues involved in mAb binding are represented balls and displayed over the ribbon diagram of gp120. FIG. 11B shows mapping of contact residues on the inner domain sequence. Residues of gp120 (from strains 93TH057 (for N5-i5, N60-i3 and JR4 footprints, these three sequences are identical and found in SEQ ID NO:58) and 89.6P (for 2.2c footprints; SEQ ID NO:59)) involved in binding to N5i5, N60i3, JR4 and 2.2c are highlighted. FIG. 11C shows sequence conservation of Cluster A epitopes. The height of the residue at each position is proportional to its frequency of distribution among the HIV-1 isolates as deposited Los Alamos data base (all clades are included).

FIGS. 12A-12B. Design of inner domain constructs. FIG. 12A shows the subsequent steps of design of the inner domain molecule; (left) structure of $gp120_{93TH057}$ $core_e$ in CD4-bound conformation (from the N5-i5 Fab-$gp120_{93TH057}$-d1d2CD4 complex, Protein Data Bank (PDB) code: 4H8W); (middle and right) the putative ID1 and ID2 immunogen structures. Asn-proximal NAG residues of glycosyl group and disulfide bonds of inner domain are shown as balls-and-sticks. FIG. 12B shows sequence of ID constructs ID1 (SEQ ID NO:56) and ID2 (SEQ ID NO:57) which are based on the gp120 sequence (SEQ ID NO:55) of the HIV-1 isolate 93TH057. The -GG- and -GGA-linkers are indicated, as is the $C_{65}$-$C_{115}$ disulfide introduced to ID1. Inner domain layers are shaded as in (A).

FIGS. 13A-13B. Physico-chemical characterization of ID1. FIG. 13A shows analytical RP-HPLC where ID1 (left panel) and PNGF digestion product of ID1 (right panel) were analyzed on Symmetry 300™ C4 column (2.1×150 mm, 3.5 μm) using a linear gradient of 5-65% of acetonitrile at a flow rate of 0.25 mL/min over 30 min. FIG. 13B shows SDS PAGE analysis of purified ID1 (line 1), ID1 subjected to cleavage with PNG F (line 2), protein standards (line 3).

FIGS. 14A-14B. Binding of Cluster A antibodies to ID2. FIG. 14A provides bar graph for binding affinity ($K_D$) of Cluster A mAbs to FLSC (column 1), $gp120_{BaL}$ (column 2), ID1 (column 3), and ID2 (column 4). The insert represents a magnified view of the higher binding affinity section of the graph. Units are in nM. FIG. 14B shows isothermal titration calorimetry (ITC) curves for A32 IgG against FLSC and ID2.

FIGS. 15A-15B. Functional properties of ID2. FIG. 15A shows results from anti-Cluster A ADCC competition. ADCC activities of Cluster A mAbs (at concentration 0.67 nM) in the presence of increasing concentrations of ID2 protein were measured using gp120-coated CEM GFP CCR5 snap cells as targets and PBMCs as effector cells. FIG. 15B shows results from ADCC competition of antibodies in sera from HIV-infected individuals. CEM.NKr cells infected with Nef-Vpu-VSV-G pseudotyped NL4.3 GFP ADA were used at 48 h post-infection for surface staining (left) and FACS-based ADCC assay (right) using sera from HIV-1 infected individuals pre-incubated in absence or presence of 10 μg ΔV1V2V3V5 D368R or 2.66 μg inner domain protein/μl sera for 30 min at room temperature. Data shown are representative of at least three different experiments. Statistical significance was tested using paired one-way ANOVAs ( $p<0.01$, * $p<0.001$, **** $p<0.0001$).

FIG. 16. Humoral Immune Response Induced by ID2 in Rabbits. (A) shows the results of evaluation of IgG titers elicited in sera of immunized rabbits against ID2 protein. 10-fold dilutions of heat inactivated rabbits sera, were tested in a direct ELISA (see Material and Methods). (B) shows recognition and (C) shows ADCC response of antibodies elicited in sera of immunized rabbits against HIV-1 gp120-coated cells. CEM.NKr cells were coated with 100 ng/ml of recombinant HIV-1 gp120 and analysed to be recognized/ADCC killed (as measured by FACS-based ADCC assay [80] by antibodies elicited in rabibit sera of week 0, 12 and 15 (1:100 and 1:1000 dilution). (D) shows the ADCC response of antibodies elicited in rabibit sera against HIV-1 infected cells. CEM.NKr cells were infected with HIV-1 lacking Nef and Vpu (N-U-) for 48 h and the FACS-based ADCC assay with rabbit sera of weeks 0 and 15 (diluted at 1:100) was performed. Alternatively, target cells were pre-incubated 30 min with 5 μg/ml of Fab A32 or Fab 17b prior incubation with effector cells and rabbit sera. Data shown represents the percentage of ADCC-mediated killing obtained from three independent experiments.

FIG. 17. Specificity of antibodies elicited in immunized rabbits. Recognition of HIV-1 gp120-coated cells by antibodies of sera of immunized rabbits (week 0, 12 and 15; 1:100 dilution) was analyzed using CEM.NKr cells coated with 100 ng/ml of recombinant HIV-1 gp120. The target cells were pre-incubated 30 min with Fabs of Cluster A mAbs A32 and N5-i5, co-receptor binding side mAb N12-i2 and ΔV1V2V3V5 D368R gp120 (a gp120 variant bearing a D368R mutation abrogating the ability of gp120 to bind to cell surface CD4 and lacking variable regions V1, V2, V3, and V5 as described in [41] before mixing with sera and analyzing for surface staining. Data shown are representative of at least two different experiments.

DETAILED DESCRIPTION OF THE INVENTION

I. Definitions

Unless otherwise noted, technical terms are used according to conventional usage. Definitions of common terms in molecular biology may be found, for example, in Benjamin Lewin, Genes VII, published by Oxford University Press, 2000 (ISBN 019879276X); Kendrew et al. (eds.); The Encyclopedia of Molecular Biology, published by Blackwell Publishers, 1994 (ISBN 0632021829); and Robert A. Meyers (ed.), Molecular Biology and Biotechnology: a Comprehensive Desk Reference, published by Wiley, John & Sons, Inc., 1995 (ISBN 0471186341); and other similar technical references.

As used herein, "a" or "an" may mean one or more. As used herein when used in conjunction with the word "comprising," the words "a" or "an" may mean one or more than one. As used herein "another" may mean at least a second or more. Furthermore, unless otherwise required by context, singular terms include pluralities and plural terms include the singular.

As used herein, "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

II. The Present Invention

As indicated above, provided herein are protein immunogens that selectively present the HIV-1 gp120 polypeptide C1/C2 region (or both the C1/C2 and V1/V2 regions) in its CD4-bound state within a minimal structure. These immunogens can be used in vivo for inducing humoral Fc-mediated effector responses to C1/C2 region epitopes (or both C1/C2 and V1/V2 regions) without the complication of neutralization epitopes. The invention focuses on A32-like epitope targets because they persist on freshly infected cell surfaces for extended periods of time post-infection [52, 53]. The persistence of C1/C2 region epitopes on target cell surfaces in a model of cell-to-cell HIV-1 spread is unique as the exposure of other non-neutralizing conserved domains such as the Cluster I and II epitopes of gp41 is evanescent [54, 55]. The C1/C2 region epitopes are potentially better targets for ADCC antibodies capable of the blocking of HIV-1 infection as opposed to epitopes exposed during viral budding. Passive immunization studies suggest that protective neutralizing antibodies have less than a twenty-four hour window to block transmission [56, 57]. This time frame is around the length of a single replication cycle of HIV-1 [58, 59] making it unlikely that transmission-blocking antibodies involve the recognition of budding virions from infected cells. The C1/C2 region-specific epitopes can also be important, along with those on budding virions, as ADCC targets in the post-infection control of viremia by Fc-mediated effector function is incorporated in vaccine strategy.

ID Immunogens

The invention is directed to HIV-1 gp120 polypeptide inner domain (ID) immunogens which include immunogens designed to exclusively present epitopes within the C1/C2 region as well as immunogens designed to present epitopes within both the C1/C2 region and the V1V2 loop.

The ID immunogens of the invention are derived from HIV-1 gp120 polypeptides, where selected regions or domains are deleted in order to limit the immunogens to amino acids of the gp120 inner domain. In addition, it has been found that by altering the sequence of the immunogens to exhibit cysteine residues at specific positions, disulfide bond formation occurs that results in a stable immunogen which selectively presents CD4-inducible epitopes. Therefore, the ID immunogens of the invention are also engineered to have cysteine residues in selected positions.

Each of the ID immunogens of the invention is based on a mature HIV-1 gp120 polypeptide sequence, but lacks selected domains and includes particular amino acid changes. The mature gp120-based ID immunogens are thus further characterized by two or more of the following features:

(i) deletion of a portion of the N-terminus of the protein (generally corresponding to residues 1-11 of gp120 from the HIV-1 isolate HXBc2 set forth in SEQ ID NO:1);

(ii) engineered cysteines at positions 65 and 115 corresponding to the sequence of the HXBc2 isolate, which leads to stabilization of the immunogen in a CD4-bound conformation upon disulfide bond formation between the cysteines ($C_{65}$-$C_{115}$);

(iii) deletion of the outer domain region of the protein (generally corresponding to amino acids 258-472 of the HXBc2 isolate) and replacement by a GlyGly dipeptide linker; and (iv) deletion of the V1V2 loop of the protein (generally corresponding to amino acids 119-205 of the HXBc2 isolate) and replacement by a GlyGlyAla tripeptide linker.

More succinctly, the HIV-1 gp120 ID immunogens of the invention are those that comprise a mature HIV-1 gp120 polypeptide having two or more of the features (i)-(iv):

(i) deletion of amino acids 1-11 of the N-terminus, (ii) cysteine residues at amino acid positions 65 and 115, (iii) deletion of amino acids 258-472 of the outer domain region and replacement by a GlyGly dipeptide linker, and (iv) deletion of amino acids 119-205 of the V1V2 loop and replacement by a GlyGlyAla tripeptide linker, wherein the amino acid numbering corresponds to the amino acid sequence set forth in SEQ ID NO:1.

As discussed in detail below, the ID immunogens of the present includes also include variants having at least about 95% sequence identity with one of these immunogen over the entire length of the immunogen sequence.

In certain aspects of the invention, the ID immunogen has three of the features (i)-(iv). In particular aspects, the ID immunogen has features (i) and (ii), or features (i) and (iii), or features (i) and (iv), or features (ii) and (iii), or features (ii) and (iv), or features (iii) and (iv), or features (i), (ii) and (iii), or features (ii), (iii) and (iv), or features (i), (ii) and (iv), or features (i), (iii) and (iv), or features (i)-(iv). In exemplary aspects, the ID immunogen has features (i)-(iii) or features (i)-(iv).

Reference herein to "a mature HIV-1 gp120 polypeptide" means a gp120 polypeptide without the signal peptide. Thus, for example, reference to "amino acids 1-11 of the N-terminus . . . wherein the amino acid numbering corresponds to the amino acid sequence set forth in SEQ ID NO:1" indicates that SEQ ID NO:1 is the amino acid sequence of a mature gp120 protein lacking the signal peptide. The mature gp120 protein provided in SEQ ID NO:1 is mature gp120 from the HIV-1 isolate HXBc2. The sequence of the full-length protein (i.e., containing the signal peptide at positions 1-30) is provided in SEQ ID NO:2.

In certain aspects, the ID immunogens have a $C_{65}$-$C_{115}$ disulfide bond. In other aspects, the ID immunogens exist without a disulfide bond linking $C_{65}$-$C_{115}$.

As will be clear from the present disclosure, the identity of the gp120 polypeptide upon which the ID immunogens of the invention may be based is not a limiting factor in the invention. Therefore, any gp120 polypeptide sequence, now known or later characterized, may serve as the basis for an ID immunogen of the invention. Thus, HIV-1 gp120 sequences can be used without regard to the clade, isolate or strain from which they are obtained. However, exemplary clades from which gp120 polypeptides may be selected include, but are not limited to, HIV-1 clades A1, A2, B, C, D, F1, F2, G, H, 01_AE, 02_AG, 03_AB, 04_CPX, 06_CPX, 08_BC, 10_CD, 11_CPX, 12_BF, and 14_BG. Exemplary strains from which gp120 polypeptides may be selected include, but are not limited to, strains AB097872 and AB052867 (clade A), strains YU2 and HXBc2 (clade B), strains HM623558 and DQ404010 (clade C), and strains 93TH057 and 92TH023 (clade AE).

Specific examples of ID immunogens of the invention based on the consensus sequence of different HIV-1 clades are provided in Table 1 where the ID immunogens have each of features (i)-(iii) (i.e., retaining the V1V2 region) and where the clades are A1, A2, B, C, D, F1, F2, G, H, 01_AE, 02_AG, 03_AB, 04_CPX, 06_CPX, 08_BC, 10_CD, 11_CPX, 12_BF, and 14_BG. The entry termed "CON_OF_CONS_V1V2" is an ID immunogen based on the consensus of consensus sequences of HIV-1 clades shown. An amino acid sequence alignment of these immunogens is provided in FIG. 1.

TABLE 1

| | |
|---|---|
| A1_V1V2 | SEQ ID NO: 3 |
| A2_V1V2 | SEQ ID NO: 4 |
| B_V1V2 | SEQ ID NO: 5 |
| C_V1V2 | SEQ ID NO: 6 |
| D_V1V2 | SEQ ID NO: 7 |
| F1_V1V2 | SEQ ID NO: 8 |
| F2_V1V2 | SEQ ID NO: 9 |
| G_V1V2 | SEQ ID NO: 10 |
| H_V1V2 | SEQ ID NO: 11 |
| 01_AE_V1V2 | SEQ ID NO: 12 |
| 02_AG_V1V2 | SEQ ID NO: 13 |
| 03_AB_V1V2 | SEQ ID NO: 14 |
| 04_CPX_V1V2 | SEQ ID NO: 15 |
| 06_CPX_V1V2 | SEQ ID NO: 16 |
| 08_BC_V1V2 | SEQ ID NO: 17 |
| 10_CD_V1V2 | SEQ ID NO: 18 |
| 11_CPX_V1V2 | SEQ ID NO: 19 |
| 12_BF_V1V2 | SEQ ID NO: 20 |
| 14_BG_V1V2 | SEQ ID NO: 21 |
| CON_OF_CONS_V1V2 | SEQ ID NO: 22 |

Specific examples of ID immunogens of the invention based on different HIV-1 strains are provided in Table 2 where the ID immunogens have each of features (i)-(iii) (i.e., retaining the V1V2 region) and where the strains are strains AB097872 and AB052867 (clade A), strains YU2 and HXBc2 (clade B), and strains HM623558 and DQ404010 (clade C). An amino acid sequence alignment of these immunogens is provided in FIG. 2.

TABLE 2

| | |
|---|---|
| AB097872_V1V2 | SEQ ID NO: 23 |
| AB052867_V1V2 | SEQ ID NO: 24 |
| yu2gp120_V1V2 | SEQ ID NO: 25 |
| HXB2_V1V2 | SEQ ID NO: 26 |
| HM623558_V1V2 | SEQ ID NO: 27 |
| DQ404010_V1V2 | SEQ ID NO: 28 |

Specific examples of ID immunogens of the invention based on the consensus sequence of different HIV-1 clades are provided in Table 3 where the ID immunogens have each of features (i)-(iv) (i.e., the V1V2 region is replaced by the GGA trimer) and where the clades are A1, A2, B, C, D, F1, F2, G, H, 01_AE, 02_AG, 03_AB, 04_CPX, 06_CPX, 08_BC, 10_CD, 11_CPX, 12_BF, and 14_BG. The entry termed "CON_OF_CONS" is an ID immunogen based on the consensus of consensus sequences of HIV-1 clades shown. An amino acid sequence alignment of these immunogens is provided in FIG. 4.

TABLE 3

| | |
|---|---|
| A1 | SEQ ID NO: 29 |
| A2 | SEQ ID NO: 30 |
| B | SEQ ID NO: 31 |
| C | SEQ ID NO: 32 |
| D | SEQ ID NO: 33 |
| F1 | SEQ ID NO: 34 |
| F2 | SEQ ID NO: 35 |
| G | SEQ ID NO: 36 |
| H | SEQ ID NO: 37 |
| 01_AE | SEQ ID NO: 38 |
| 02_AG | SEQ ID NO: 39 |
| 03_AB | SEQ ID NO: 40 |
| 04_CPX | SEQ ID NO: 41 |
| 06_CPX | SEQ ID NO: 42 |
| 08_BC | SEQ ID NO: 43 |
| 10_CD | SEQ ID NO: 44 |
| 11_CPX | SEQ ID NO: 45 |
| 12_BF | SEQ ID NO: 46 |
| 14_BG | SEQ ID NO: 47 |
| CON_OF_CONS | SEQ ID NO: 48 |

Specific examples of ID immunogens of the invention based on different HIV-1 strains are provided in Table 4 where the ID immunogens have each of features (i)-(iv) (i.e., the V1V2 region is replaced by the GGA trimer) and where the strains are strains AB097872 and AB052867 (clade A), strains YU2 and HXBc2 (clade B), and strains HM623558 and DQ404010 (clade C). An amino acid sequence alignment of these immunogens is provided in FIG. 5.

TABLE 4

| | |
|---|---|
| AB097872 | SEQ ID NO: 49 |
| AB052867 | SEQ ID NO: 50 |
| yu2gp120 | SEQ ID NO: 51 |
| HXB2 | SEQ ID NO: 52 |
| HM623558 | SEQ ID NO: 53 |
| DQ404010 | SEQ ID NO: 54 |

Variants

Due to the high degree of conservation between gp120 polypeptide sequences from different HIV-1 clades and strains, minor variations can be made to the ID immunogens without altering the ability of the resulting variants to induce non-neutralizing Fc-mediated effector responses. Thus, ID immunogens of the invention include variants of selected gp120 sequences. The variants can have any combination of amino acid additions, deletions or substitutions, but the variants of the invention will have at least about 80% sequence identity with an ID immunogen as defined herein over the entire length of the amino acid sequence of the selected ID immunogen. In certain aspects, the variants will have at least about 81%, 82%, 83%, 84%, 85%, 86%, 87%, 88%, 89%, 90%, 91%, 92%, 93%, 94%, 95%, 96%, 97%, 98% or 99% sequence identity with an ID immunogen, e.g., the ID immunogens set forth in SEQ ID NOs:3-54. Each of the variants of the invention has the property of inducing Fc-mediated humoral response to C1/C2 or combined C1/C2 and V1/V2 regions of HIV-1 gp120.

FIG. 1 provides an amino acid sequence alignment between the ID immunogens of Table 1. FIG. 2 provides an amino acid sequence alignment between the ID immunogens of Table 2. FIG. 3 provides an amino acid sequence alignment between the ID immunogens of Tables 1 and 2. FIG. 4 provides an amino acid sequence alignment between the ID immunogens of Table 3. FIG. 5 provides an amino acid sequence alignment between the ID immunogens of Table 4. FIG. 6 provides an amino acid sequence alignment between the ID immunogens of Tables 3 and 4. See also FIG. 11C for a graphical representation of sequence conservation. These sequence alignments demonstrate the regions of identity (marked as "*" below a column of letters), conservative changes (marked as ":") and semi-conservative changes (marked as "."). between the ID immunogens. This knowledge with enable the skilled artisan to easily select residues and regions of the immunogens that may be varied via additions, deletions or substitutions.

In certain aspects of the invention, the amino acid sequence of a variant differs from the ID immunogen upon which it is based only in those residues or regions where there is no identity (marked as " "). In other aspects, the amino acid sequence of a variant differs from the ID immunogen upon which it is based in those residues or regions where there is no identity and/or there are semi-conservative changes. In still other aspects, the amino acid sequence of a variant differs from the ID immunogen upon which it is based in those residues or regions where there is no identity and/or there are semi-conservative changes and/or there are conservative changes. In still further aspects, the amino acid sequence of a variant differs from the ID immunogen upon which it is based in any residue or regions of the polypeptide. The cysteines present at positions corresponding to residues 65 and 115 of SEQ ID NO:1 are not altered in the variants.

Immunogenic Compositions

The present invention is also directed to immunogenic compositions comprising one or more of the ID immunogens as defined herein and pharmaceutically-acceptable carriers or diluents.

It will be evident that the immunogenic compositions can vary based on the number of different ID immunogens and their relative amounts present in each the composition. For example, immunogenic compositions may comprise an ID immunogen of a single selected sequence or they may comprise two or more different ID immunogens (i.e., ID immunogens having different amino acid sequences). In non-limiting examples, an immunogenic composition comprises one or more of the ID immunogens set forth in SEQ ID NOs:3-54, or variants thereof, or both.

It is contemplated that the immunogenic compositions will be administered as pharmaceutical formulations for use in inducing an immune response or vaccination of individuals, preferably humans. In addition to the ID immunogens, the immunogenic compositions may thus include pharmaceutically-acceptable carriers or diluents. The immunogenic compositions may also include other ingredients, such as an adjuvant.

The carriers and diluents must be pharmaceutically acceptable in the sense that they are compatible with the immunogens and other ingredients, and they are not unduly deleterious to the recipient. The other ingredients are provided in an amount and frequency necessary to achieve the desired immunological effect.

The pharmaceutically-acceptable carriers and diluents included in the immunogenic compositions will vary based on the amount of ID immunogens in the composition, the means used to administer the composition, the site of administration and the dosing schedule used, among other factors. Suitable examples of carriers and diluents are well known to those skilled in the art and include water-for-injection, saline, buffered saline, dextrose, water, glycerol, ethanol, propylene glycol, polysorbate 80 (Tween-80™), poly(ethylene)glycol 300 and 400 (PEG 300 and 400), PEGylated castor oil (e.g. Cremophor EL), poloxamer 407 and 188, hydrophilic and hydrophobic carriers, and combinations thereof. Hydrophobic carriers include, for example, fat emulsions, lipids, PEGylated phospholipids, polymer matrices, biocompatible polymers, liposphers, vesicles, particles, and liposomes. The terms specifically exclude cell culture medium. Additional carriers include cornstarch, gelatin, lactose, sucrose, microcrystalline cellulose, kaolin, mannitol, dicalcium phosphate, sodium chloride, alginic acid, croscarmellose sodium, and sodium starch glycolate.

As a specific example, intramuscular preparations can be prepared and administered in a pharmaceutically acceptable diluent such as Water-for-Injection, 0.9% saline, or 5% glucose solution.

The immunogenic compositions of the present invention may also include an adjuvant. Suitable adjuvants include Freund's Complete and Incomplete Adjuvant, Titermax, oil in water adjuvants, as well as aluminum compounds where antigens, normally proteins, are physically precipitated with hydrated insoluble salts of aluminum hydroxide or aluminum phosphate. Other adjuvants include liposome-type adjuvants comprising spheres having phospholipid bilayers that form an aqueous compartment containing the ID immunogen and protecting it from rapid degradation, and that provide a depot effect for sustained release. Surface active agents may also be used as adjuvants and include lipoteichoic acid of gram-positive organisms, lipid A, and TDM. Quil A and QS-21 (saponin-type adjuvants), monophosphoryl lipid A, and lipophilic MDP derivatives are suitable adjuvants that have hydrophilic and hydrophobic domains from which their surface-active properties arise. Compounds normally found in the body such as vitamin A and E, and lysolecithin may also be used as surface-active agents. Other classes of adjuvants include glycan analog, coenzyme Q, amphotericin B, dimethyldioctadecylammonium bromide (DDA), levamisole, and benzimidazole compounds. The immunostimulation provided by a surface active agent may also be accomplished by either developing a fusion protein with non-active portions of the cholera toxin, exotoxin A, or the heat labile toxin from *E. coli*. Immunomodulation through the use of anti-IL-17, anti IFN-γ, anti-IL-12, IL-2, IL-10, or IL-4 may also be used to promote a strong Th2 or antibody mediated response to the immunogenic compositions.

Methods of Inducing an Immune Response

The invention is also directed to methods of inducing an immune response to an ID immunogen in a subject comprising administering to a subject an immunogenic amount of an immunogenic composition as defined herein, thereby inducing an immune response in the subject. The immune response is preferably a protective immune response.

As used herein, an "immunogenic amount" of an immunogenic composition is one that is sufficient to induce an immune response to an ID immunogen in the subject to which the immunogenic composition is administered. A "protective immune response" is one that confers on the subject to which the immunogenic composition is administered protective immunity against HIV-1. The protective immunity may be partial or complete immunity.

As indicated above, the immunogenic compositions may comprise an ID immunogen of a single selected sequence, or two or more different ID immunogens (i.e., ID immunogens having different amino acid sequences). In non-limiting examples, an immunogenic composition comprises one or more of the ID immunogens set forth in SEQ ID NOs:3-54, or variants thereof, or both.

Methods of Vaccinating a Subject

In a related aspect, the invention is further directed to methods of vaccinating a subject with a protective antigen, comprising administering to a subject in need thereof an effective amount of an immunogenic composition as defined herein, thereby vaccinating a subject with a protective antigen.

As used herein, an "effective amount" of an immunogenic composition is one that is sufficient to induce a protective immune response to an ID immunogen in the subject to which the immunogenic composition is administered. A "protective immune response" is one that confers on the subject to which the immunogenic composition is administered protective immunity against HIV-1. The protective immunity may be partial or complete immunity.

As indicated above, the immunogenic compositions may comprise an ID immunogen of a single selected sequence, or two or more different ID immunogens (i.e., ID immunogens having different amino acid sequences). In non-limiting examples, an immunogenic composition comprises one or more of the ID immunogens set forth in SEQ ID NOs:3-54, or variants thereof, or both.

In each of the relevant methods of the present invention, the immunogenic compositions are administered in a pharmaceutically acceptable form and in substantially non-toxic quantities. The immunogenic compositions may be administered to a subject using different dosing schedules, depending on the particular use to which the compositions are put (e.g., inducing an immune response or vaccinating a subject), the age and size of the subject, and the general health of the subject, to name only a few factors to be considered. In general, the immunogenic compositions may be administered once, or may be administered more than once as boosters over a dosing schedule. The timing between each dose in a dosing schedule may range between a six, 12, or 18 hours, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more days, or 1, 2, 3, 4, 5, 6, 7, 8, 9, 10, 11, 12 or more months. The same quantity of protein in the formulation may be administered in each dose of the dosing schedule, or the amounts in each dose may vary. The identity of the particular ID immunogens in the composition may also vary or remain the same in each dose in a dosing schedule.

The amount of protein (i.e., ID immunogen) administered to a subject in a dose when the methods of the present invention are practiced will vary based on the particular methods being practiced (e.g., inducing an immune response or vaccinating a subject), the means and formulation of administration, the age and size of the subject, and the general health of the subject, to name only a few factors to be considered. In general, however, the amount of protein administered to a subject in a dose will be sufficient to induce or boost an immune response in a subject to the components of the composition. For example, the immunogenic compositions may contain between about 1 to about 1000 ug of total ID immunogen protein per kg of body weight of the subject to which the dose of the vaccine formulation will be administered, more preferably between about 10 to about 200 ug, even more preferably between about 15 to about 100 ug.

Appropriate doses and dosing schedules can readily be determined by techniques well known to those of ordinary skill in the art without undue experimentation. Such a determination will be based, in part, on the tolerability and efficacy of a particular dose, by use of conventional antibody titer determination techniques, and conventional bioefficacy/biocompatibility protocols.

The immunogenic compositions may be administered to a subject by any suitable means and/or methods for delivering the ID immunogens to a corporeal locus of a subject where the immunogenic compositions are intended to be effective in triggering an immune response, for example, for oral, sublingual, intranasal, intraocular, rectal, transdermal, mucosal, pulmonary, topical or parenteral administration. Parenteral modes of administration include without limitation, intradermal, subcutaneous (s.c., s.q., sub-Q, Hypo), and intramuscular (i.m.). Any known device useful for parenteral injection or infusion of immunogenic compositions can be used to effect such administration. In preferred aspects of each of the embodiments on the invention, the immunogenic compositions are administered to a subject by sub-cutaneous or intraperitoneal injections.

The term "subject" is intended to mean an animal, such mammals, including humans and animals of veterinary or agricultural importance, such as dogs, cats, horses, sheep, goats, and cattle.

Kits comprising the necessary components of an immunogenic composition that can be used to elicit an immune response to an ID immunogen or vaccinate a subject, and instructions for its use, are also within the purview of the present invention.

In Vitro Uses for the ID Immunogens

The ID immunogens of the invention may also be used in a wide variety of research applications. For example, the immunogens can be used as targets in screening to identify small molecule or peptide inhibitors that block HIV-1 viral entry and/or attachment steps. The immunogens can also be used as probes for identifying gp120 C1/C2 region (or C1/C2 and V1V2 combined)-specific antibodies (such as monoclonal antibodies; mAbs), e.g., for use in ELISA, C1/C2 binding titer assays, and the like, and for clinical diagnostic or research applications.

Thus, and in one aspect of the in vitro uses to which the ID immunogens may be put, the invention is directed to methods of screening for antibodies with binding affinity for the C1/C2 region HIV-1 gp120, comprising:

(a) contacting one or more ID immunogens as defined herein with a test antibody, and (b) detecting binding of the one or more ID immunogens by the test antibody.

Because antibodies can recognize and bind different antigens having similar sequences, the method of this embodiment can be conducted using one specific ID immunogen, or two or more different ID immunogens (i.e., ID immunogens having different amino acid sequences). In non-limiting examples, the ID immunogen is one or more of the ID immunogens set forth in SEQ ID NOs:3-54, or variants thereof, or both.

The antibody being screened in this aspect of the invention can be any type or form of antibody that might have binding affinity for an ID immunogen. Particular, non-limiting, examples include a monoclonal antibody, a chimeric antibody, a humanized antibody, a human antibody, a single chain antibody (scFv), an Fab fragment, an F(ab')2 fragment, a multi-specific antibody, and a disulfide-linked antibody.

Antibodies can be screened for binding to an ID immunogen, for example, by immunoassays and other techniques known to those of skill in the art including, but not limited to, western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays. Such assays are routine and well known in the art (see [85]).

Such assays may include the conjugation of a detectable substance to the ID immunogen or an antibody to be screened. Examples of detectable substances include, but are not limited to, various enzymes, prosthetic groups, fluorescent materials, luminescent materials, bioluminescent materials, radioactive materials, positron emitting metals, and nonradioactive paramagnetic metal ions. The detectable substance may be coupled or conjugated either directly to the ID immunogen or the antibody or indirectly, through an intermediate (such as, for example, a linker known in the art) using techniques known in the art. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{111}$In, or $^{99}$Tc.

In another aspect of the in vitro uses to which the ID immunogens may be put, the invention is directed to methods of screening for inhibitors of HIV-1 viral attachment comprising:

(a) contacting one or more ID immunogens as defined herein with a test molecule, and (b) detecting binding of the one or more ID immunogens by the test molecule.

The method can be conducted using one specific ID immunogen, or two or more different ID immunogens (i.e., ID immunogens having different amino acid sequences). In non-limiting examples, the ID immunogen is one or more of the ID immunogens set forth in SEQ ID NOs:3-54, or variants thereof, or both.

The test molecule may be any molecule that binds to an ID immunogen, such as an antibody or some other protein, peptide, nucleic acid, carbohydrate, lipid, fatty acid, small drug molecule, etc. After being identified as having binding affinity for an ID immunogen, the test molecule can be further screened to determine with the test molecule can interferes with the association of Env proteins displayed by HIV-1 and cell surface receptors. If this association can be inhibited or blocked, HIV-1 viral attachment and/or entry can be inhibited or blocked.

In some aspects of this embodiment, binding of the ID immunogen by the test molecule is detecting using an immunoassay such as ELISA.

Test molecules can be screened for binding to an ID immunogen, for example, by immunoassays and other techniques known to those of skill in the art including, but not limited to, western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays. Such assays are routine and well known in the art (see [85]).

Such assays may include the conjugation of a detectable substance to the ID immunogen or test molecule to be screened. Examples of detectable substances include, but are not limited to, various enzymes, prosthetic groups, fluorescent materials, luminescent materials, bioluminescent materials, radioactive materials, positron emitting metals, and nonradioactive paramagnetic metal ions. The detectable substance may be coupled or conjugated either directly to the ID immunogen or test molecule or indirectly, through an intermediate (such as, for example, a linker known in the art) using techniques known in the art. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{111}$In, or $^{99}$Tc.

IV. Examples

1. The A32-Subregion (Cluster A Epitopes) Serves as an Immunodominant Region for Potent ADCC Response During Natural Infection.

Figure 8:
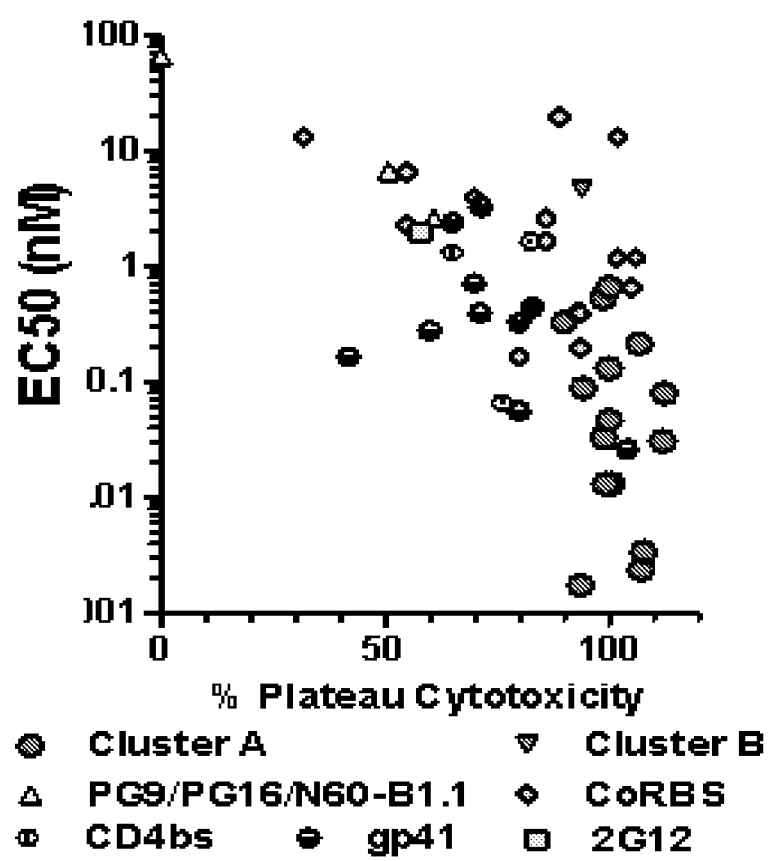

The present studies were built on available [44] and unpublished data on antibody responses specific for epitopes that are exposed on gp120 consequent to CD4 binding (CD4 inducible, CD4i epitopes). Recently, a panel of human anti-envelope antibodies was isolated from plasma of both elite controllers and non-controllers [60-62] based on an assay that detects epitopes exposed on gp120 consequent to CD4 binding during viral entry and attachment steps [44]. The ADCC assay used in the study was a fluorometric method [63], with target cells (CEMNKrCCR5+) sensitized with a saturating dose of gp120 of the HIV1$_{BaL}$ isolate to simulate the first steps of viral entry [44]. Studies on epitope specificities among mAbs in the panel [44] clearly indicated that the Fc-mediated effector function component focused on transitional non-neutralizing epitopes associated with the gp120 face that are occluded by gp41 in the HIV spike (Cluster A epitopes in [44]; see FIG. 7C). It was shown that these Env targets are capable of mediating potent ADCC against envelope coated cells and/or bound virons ([44] and FIG. 8). When assayed in the bound virion ADCC assay, Cluster A mAbs showed average IC$_{50}$ values of 0.15 nM and 100% killing [44]. Similar high ADCC potencies were reported for antibodies specific for A32-blockable epitopes and isolated from RV144 patients and induced by vaccination [36]. By contrast, none was neutralizing in the TZMb1 assay done by the CAVD Neutralization Core. Taken together, these findings underscore that non-neutralizing epitopes within A32 sub-region are extremely good targets for mAbs capable of potent ADCC. As such they will have capacities to afford protection via ADCC, depending on the dynamics and timing of antigenic exposure within the transitional structures that arise during virus-cell attachment/entry.

2. ADCC Activity Directed to A32 (Cluster A) Subregion and Induced by the Single Chain Gp120-CD4 Complex Subunit Vaccine is Associated with a Reduced Rate of Acquisition.

Figure 9:
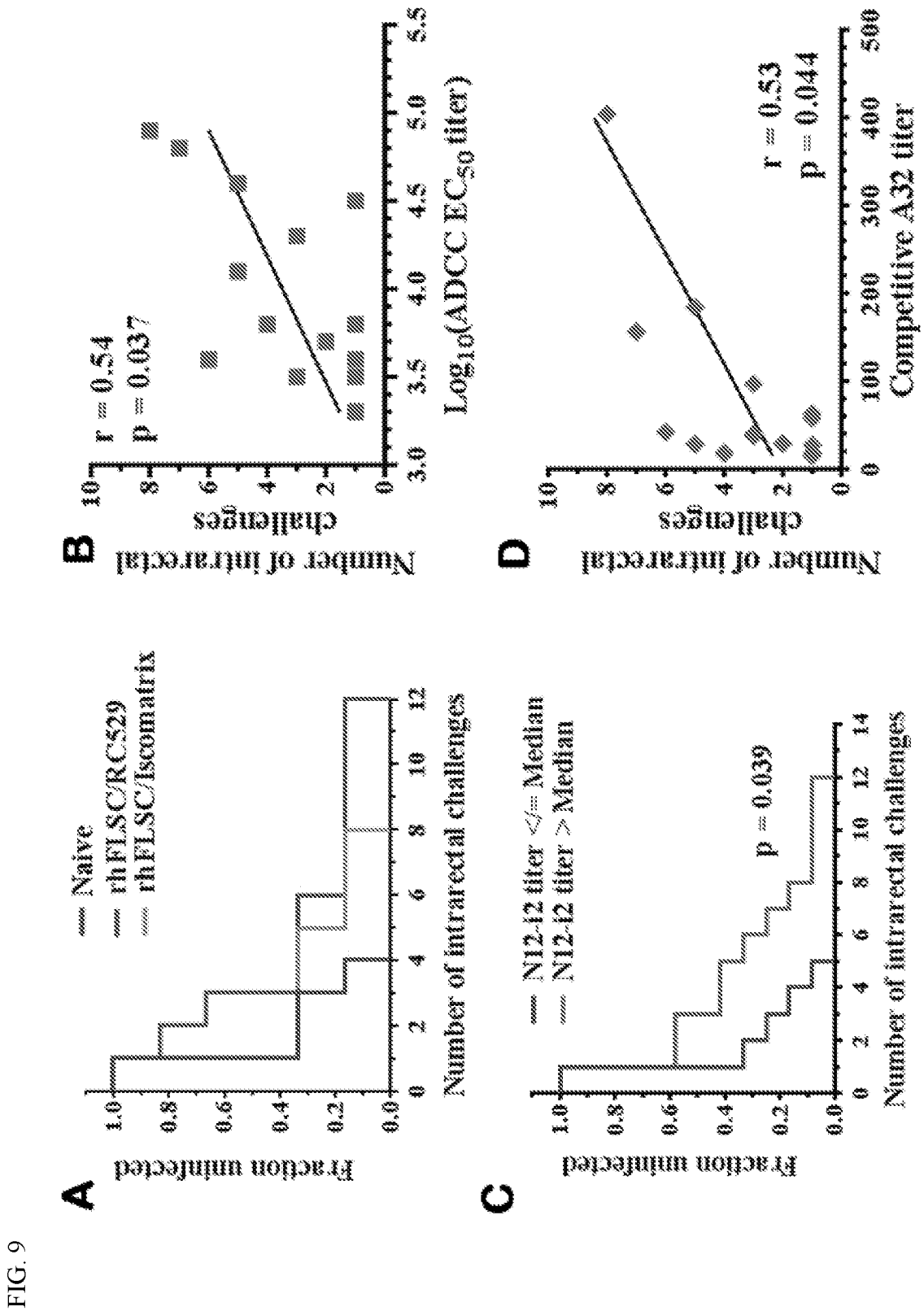

A single chain gp120-CD4 complex (rhFLSC) subunit vaccine was developed that comprises gp120 of the $HIV1_{BaL}$ isolate fused to the d1d2 domains of rhesus CD4. The vaccine was found to elicit protective immunity against a rectal challenge with $SHIV_{162p3}$. rhFLSC induced antibody responses to highly conserved domains of the envelope that become exposed only upon binding to CD4 [66, 67]. These include epitopes within/around the co-receptor binding site but also transitional epitopes associated with the N and C termini of gp120, including the A32 sub-region [66, 67]. These epitopes show poor immunogenicity in conventional gp120 based vaccines [60, 66, 67]. Parenteral immunization of rhesus macaques with rhFLSC allows the elite control of a single high-dose rectal $SHIV_{162p3}$ infection to undetectable levels in two studies, ([60, 81]. Apparent non-sterilizing protection of rhesus macaques against repeated low-dose challenges with $SHIV_{162p3}$ was observed in two additional rhFLSC immunization studies [81]. An example of one of the low-dose challenge studies is shown in FIG. 9. By the end of four challenges, all of the naïve animals were infected whereas two groups immunized with rhLFLSC showed a clear trend towards reduced acquisition (FIG. 9A).

In this study, as in all other cases of rhFLSC challenge studies, protection correlated with the titers of antibodies specific for epitopes selectively exposed on gp120 consequent to CD4 binding (CD4i epitopes, [60]) but not with conventional neutralizing antibodies. In all cases the control of SHIV replication afforded by rhFLSC immunizations correlated with ADCC [81]. As show in FIG. 9B, a strong correlation was apparent between the number of intrarectal challenges required to infect and ADCC $EC_{50}$ titer. Specificity analysis confirmed that protection was mediated by antibody responses directed to two CD4i epitope sub-regions: the co-receptor binding site (CoRBS) (FIG. 9C) and A32 sub-region (FIG. 9D). As shown in FIG. 9C, slower acquisition rates were observed in animals where the cumulative competitive epitope titers to mAb N12i2, a recently described CoRBS antibody [44], were above the median. A correlation was also apparent between the number of intrarectal challenges and competitive binding titers to A32 epitope (FIG. 9D). Whereas mAb N12i2 was shown to act through both direct neutralization and ADCC [44], mAb A32 is non-neutralizing and capable only of potent ADCC [39]. Taken together, these data show that ADCC is associated with a reduced rate of acquisition with challenge virus and that A32 sub-region (Cluster A region) is one of two specificities conferring protection in low-dose heterologous $SHIV_{162p3}$ challenge studies with rhFLSC. Interestingly, in all these studies a higher rate of infection was observed for animals that exhibited IL2 ELISPOTs counts above the mean, indicating that tightly balanced T cell help is needed to establish effective protective immunity [81].

3. Cluster A Antibodies Recognize Highly Conserved Epitope Surfaces within the Inner Domain of C1/C2 Regions of Gp120.

Next, x-ray crystallography was employed to map Cluster A epitopes at the atomic level [82,83]. Structures of complexes of antigen binding fragments (Fabs) with CD4-triggered gp120 cores of four A32-like antibodies were produced. These include: mAb N5i5 and N60i3, both isolated from a selected cohort [60-62]; mAb JR4, a recombinant hybridoma cell line clone of the rhesus macaque mAb 3.5B; mAb 2.2c, an antibody derived by Epstein-Barr virus (EBV) transformation of peripheral blood B cells from an HIV1-infected subject (RW/92/13) [44].

N5i5, N60i3 and JR4 Fabs were co-crystallized with Clade A/E $gp120_{93TH057}$ $core_e$ triggered with d1d2 domain CD4 (N5i5) or the CD4 peptide mimetic M48U1 or M48 (N60i3 and JR4, respectively). These mAbs cross-compete with each other and with mAb A32 for binding to monomeric gp120 as tested by ELISA ([44] and unpublished data). Structures of complexes were solved by molecular replacement approach at a resolution in a range of 1.8-3.5 Å [82,83]. 2.2c Fab was co-crystallized with Clade B $gp120_{YU2}$ $core_e$ and the CD4 mimetic peptide M48U1 and the structure was solved at 3.5 Å.

Figure 10:
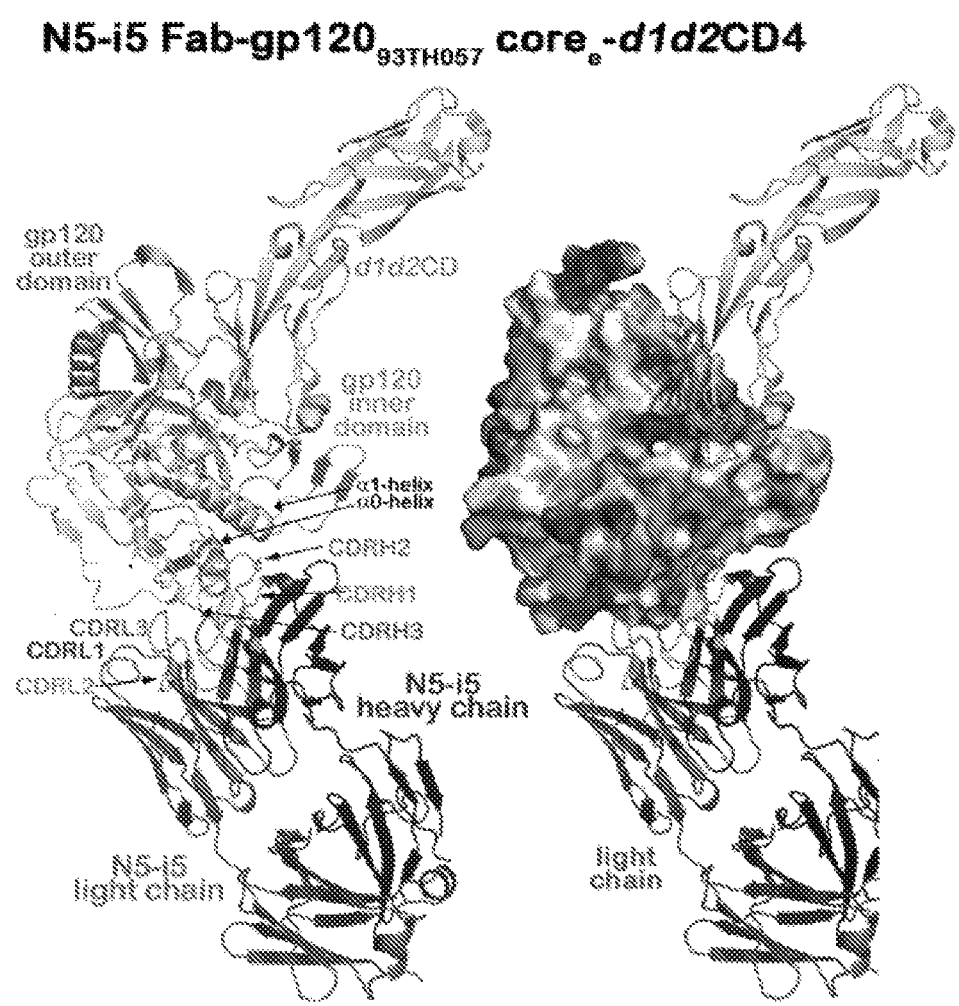
Figure 10:
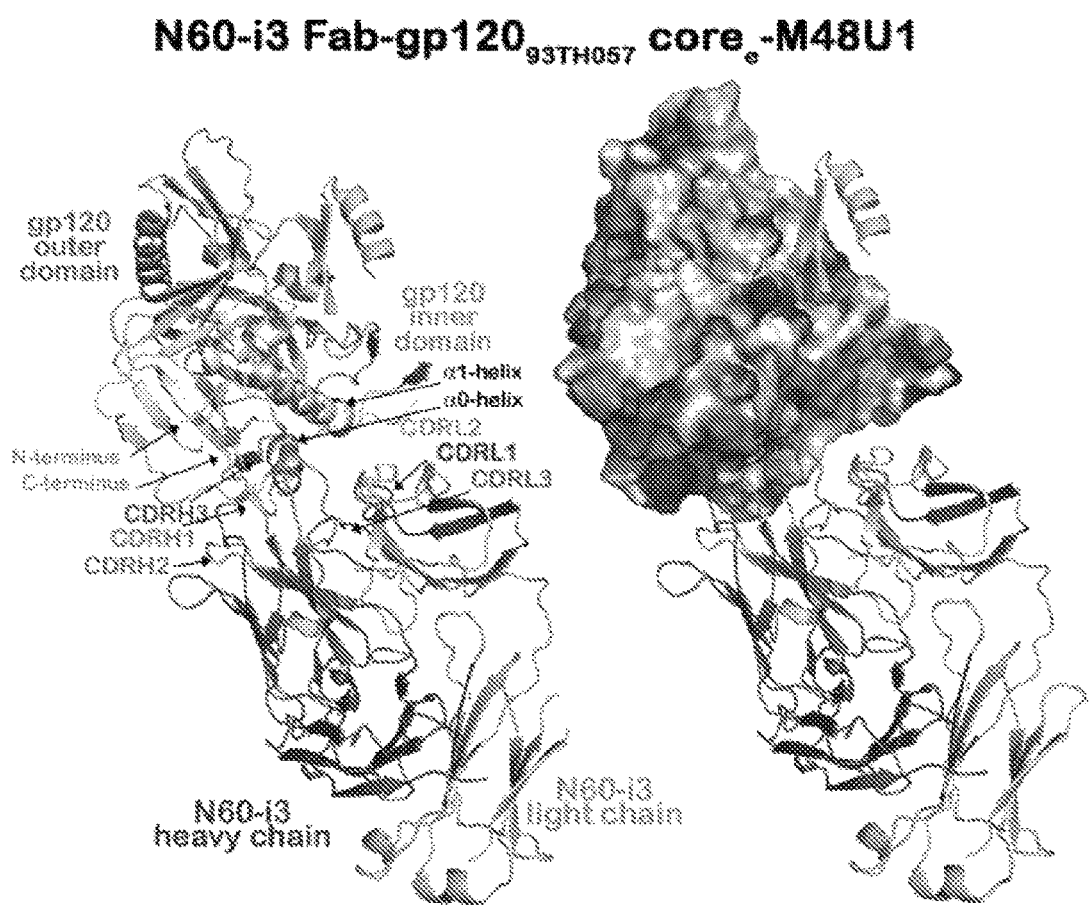
Figure 10:
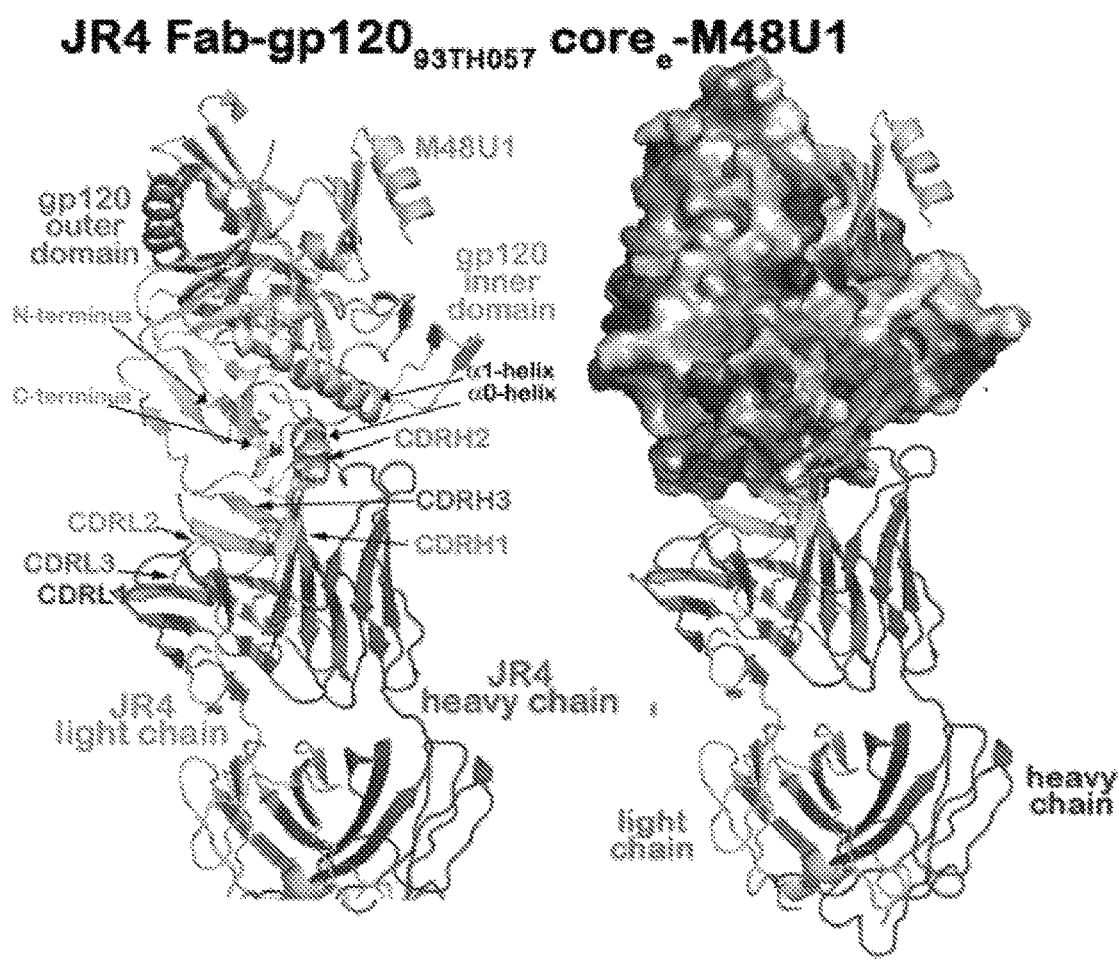
Figure 10:
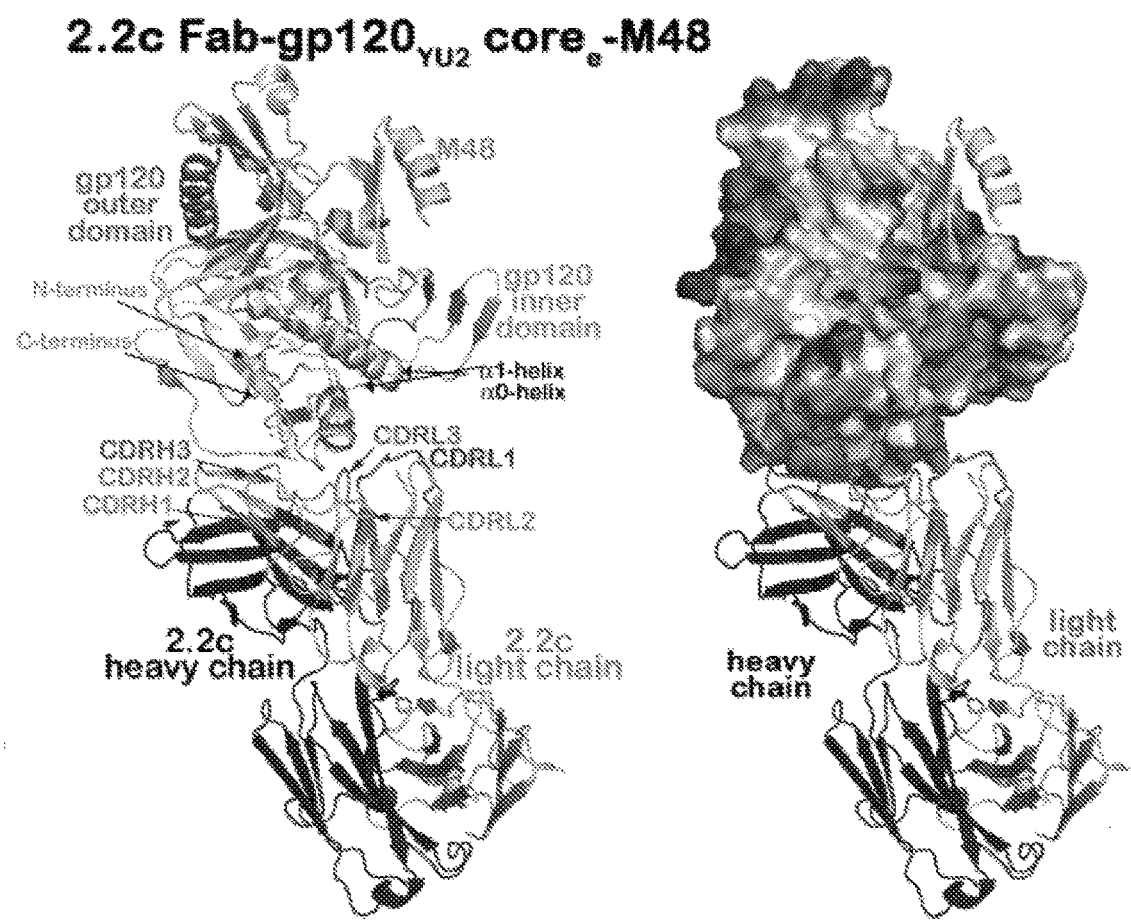

As shown in FIG. 10, mAbs N5i5, N60i3, JR4 and 2.2c bind to largely overlapping areas of gp120, proximal to the N- and C-terminal extensions. These mAbs approach gp120 from slightly different angles and target their epitopes by two binding modes as shown by a heavy and light chain variable region switch. The structures reveal precise complementarity between positively-charged Fab paratopes, contributed largely by CDR H2 and electronegative and glycan-free surfaces of the inner domain (FIG. 10). The epitope terrains contributed by short CDRH3s (10, 12, 14 and 11 residue long for N5i5, N60i3, JR4 and 2.2c, respectively) are relatively flat in all cases. The short CDRH3s in these mAbs are distinct from the extended CDRH3s that many broadly neutralizing mAbs often have [64, 65].

Analysis of CDR sequences of the entire Cluster A pool confirmed that mAbs in this group share the same characteristics of the antigen binding site with a moderate length of CDR H3 loops. In addition, a statistically significant inverse correlation was observed between CDRH3 length and ADCC activity (data not shown), confirming that effective ADCC potency of these antibodies is not associated with unique or unusual structural features such as a long CDR H3. It is also important to note that broadly neutralizing antibodies (bnAbs) typically exhibit high levels of somatic hypermutation (SHM) [66, 67], whereas Cluster A mAbs are only mutated modestly at averages of 5% to 10% at the protein level [82,83]. There is no correlation between the degree of $V_H$ affinity maturation and ADCC potency (data not shown). This underscores the view that if these epitopes are targets of protective antibodies in vivo, these relatively low levels of SHM can be readily attained with standard vaccination regimens.

Figure 11B:
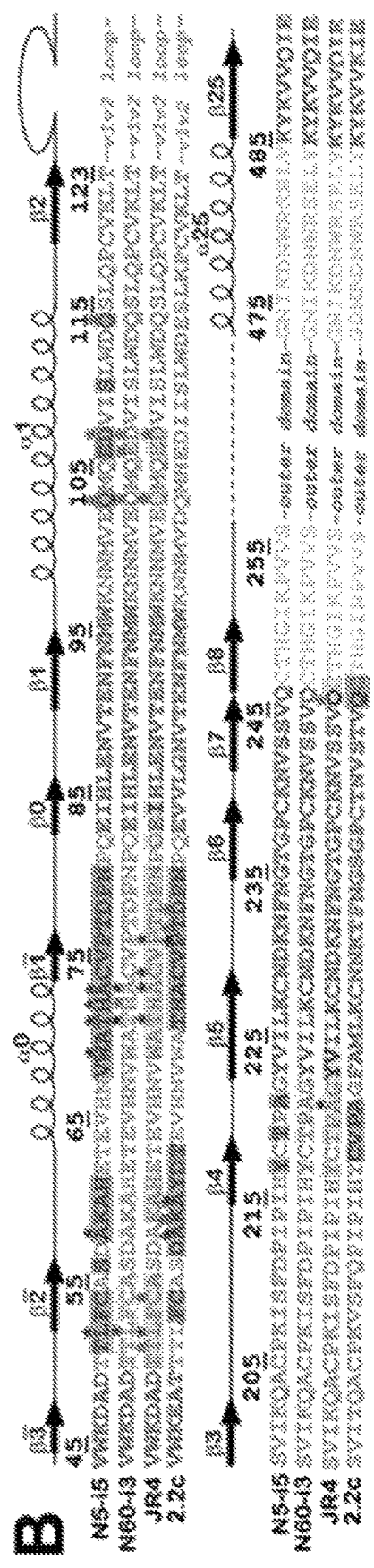
Figure 11C:
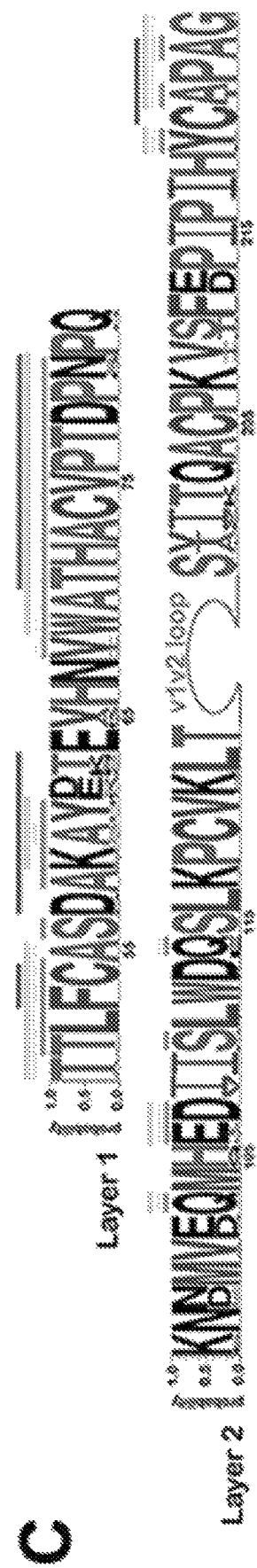

Detailed analysis of epitope footprints of N5i5, N60i3, JR4 and 2.2c within Env antigen (FIG. 11) indicates that they map exclusively to the inner domain of gp120 within the C1 and C2 regions (FIGS. 11A and 11B). N5i5, N60i3 and JR4 bind to layer 1 (β2, β1-strands, β2α0- and β1β0-connecting coils) and layer 2 (α1-helix, β4 strand and β4-β5-connecting coil) of C1/C2 region with an average of 70% of the epitope surface mapped to layer 1 (FIGS. 11A and 11B). mAbs N60i3 and JR4 make a few additional contacts with the 7-stranded β-sandwich and layer 3. mAb 2.2c targets mainly residues of layer 1 (94% of contact surface area) with few contacts within the β4-strand of layer 2 and no binding contacts to the α1-helix (FIGS. 11A and 11B). These epitope surfaces map to the highly conserved gp120 region with many single residue/residue motifs being strictly conserved as shown in FIG. 11C.

High conservation of Cluster A region suggests that it is functionally relevant. Indeed analysis of the Cluster A epitope footprints in context of the native untriggered virion-associated HIV-1 trimers [68] and structures of a cleaved, soluble SOSIP gp140 trimer [69, 70] indicate that they map to a region of gp120 that is buried within the trimer interface and engaged directly in interactions with the gp41 central helix (HR1) of the trimer (data not shown, [82,83]). In addition, mutagenesis studies confirm involvement of residues forming Cluster A epitopes (such as $Leu^{52}$, $Phe^{53}$, $Trp^{69}$, $His^{72}$, $Ala^{73}$ and $Asp^{107}$) in stabilization of the unliganded Env trimer or contribution to layer 1 and 2 functions in conformational transitions upon CD4 receptor binding [71-73]. Taken together, these findings indicate that potent A32-like entry targets localize to highly conserved epitope surface within the C1/C2 gp120 region, at the junction of the functional layer 1 and 2 of inner domain. These regions are known to interact with gp41 in untriggered trimeric Env thus are inaccessible for antibody recognition until interactions of Env with the host receptor CD4.

4. Stable Inner Domain Construct ID1 as Cluster A mAb Target.

Isolation of the Cluster A epitope into the smallest, stable structural unit of gp120 possible, and in one embodiment without epitopes recognized by neutralizing antibodies, was sought. Crystallographic analysis indicated that Cluster A mAbs bind to a conformationally-conserved surface, which is centered around β2, β1-strands and α0- and α1-helixes of layer 1 and 2 in the CD4-bound state and without involvement of the gp120 outer domain and variable loops (FIGS. 10 and 11). Based on this information, it was hypothesized that an inner domain (ID) immunogen with V1V2 loop deleted, preferentially stabilized in the CD4-bound conformation, would be a suitable minimal structure that could be evaluated without the complication of neutralization epitopes being present. The initial design was based on an observation that unliganded HIV-1 gp120 extended core ($core_e$) tended to spontaneously adopt the CD4-bound conformation. It was shown for several structures of unliganded gp120 $core_e$s of different HIV-1 clades that gp120 truncated to preserve its extended core resembles the CD4-bound conformation which represents a "ground state" for gp120 when variable loops are removed [77,78].

A stable inner domain construct of gp120 from HIV-1 clade A/E isolate 93TH057 (SEQ ID NO:55; "gp120" of FIG. 12B), which is composed of the gp120 $core_e$ sequence with the outer domain sequence (residues 258-472, HxBc2 numbering) replaced within inner domain Layer 3 by a simple -GG-dipeptide linker (FIG. 12) was prepared. The first design of the inner domain immunogen is referred to "ID1" (SEQ ID NO:56). A synthetic ID1 gene was fused to the signal peptide sequence, placed into pCMV6-A-puro vector, expressed by transient transfection of 293T cells (FreeStyle™ mammalian 293T and $GnTi^-$ 293 T Expression System (Invitrogen, Carlsbad, Calif.)) and purified from cell supernatants via N5-i5 IgG affinity and gel filtration chromatography. The typical production and purification procedure yielded 1-2 mg of ID1 per liter of culture. Shown in FIG. 13 is the final purified sample of ID1 analyzed by RP-HPLC, SDS-PAGE and gel filtration chromatography.

The ID1 construct contains eight cysteine residues and all eight are involved in disulfide bond formation (FIGS. 12A and 12B). A single RP-HPLC protein peak (FIG. 13A) indicates that the ID molecule, folded, fully oxidized and purified, consists of a homogeneous species in solution and not a mixture of different disulfide-bonded isomers. Purified ID1 protein has a molecular weight of ~31-32 kDa as determined by SDS-PAGE (FIG. 13B, line 1). This corresponds to the molecular weight of the protein backbone (MW of 21,886 Da as calculated on the basis of the average isotopic compositions of the protein) and 3 N-glycosyl groups attached to N88, N234 and N241. Removal of these groups with PNGF yielded a protein backbone of molecular weight in good agreement with the expected values calculated on the basis of the average isotopic compositions of the protein (FIG. 13B, line 2). Analysis of the ID sequence identified no new potential sites of N- or O-linked glycosylation in the newly exposed (after the outer domain removal) solvent accessible surface. Size-exclusion chromatography analyses indicate that un-liganded ID1 forms a monomer in solution (data not shown).

mAb A32 is capable of binding unliganded gp120 but CD4-triggering significantly enhances its exposure and stability in the context of full length protein [44, 79]. Binding of Cluster A mAbs, including mAb A32 and anti-Cluster A mAbs N5-i5, N60-i3, 2.2c and JR4 [44] to monomeric full length gp120 of BaL isolate ($gp120_{BaL}$) and to the single-chain $gp120_{BaL}$-sCD4 complex (FLSC) [46] was tested by surface plasmon resonance (SPR) on a Biacore T-100 (GE Healthcare) at 25° C. The kinetic constants were determined using a 1:1 Langmuir model of binding with the BIAevaluation software (GE Healthcare) and the results are shown in Table 5. All mAbs tested showed increased affinities for the gp120-CD4 complex as shown by a 8-32 fold lower affinity constant ($K_D$) for FLSC as compared to unliganded gp120 (Table 5). In all cases the increased affinity for the $gp120_{BaL}$-sCD4 complex resulted from the faster association rates and reduced dissociation rates confirming that the epitopes in the C1-C2 region is indeed inducible and stabilized in the context of monomeric gp120 by CD4 triggering. The same antibodies were used set to test how the C1-C2 region epitopes are preserved within the ID1 molecule. As shown in Table 5, ID1 binds effectively to each of five antibodies tested, with a $K_D$ value in a range of 1.1-9.3 nM thus with affinities comparable or slightly improved as compared to the full-length gp120 ($K_D$ value in a range of 2.0-12.0 nM). This indicates that the inner domain molecule ID1 preserves the antigenic properties of monomeric gp120 and is folded to effectively display A32-like epitopes within a minimal structural unit of gp120. ID1 represents a first stable construct of inner domain of gp120 expressed independently of the outer domain.

TABLE 5

Binding kinetics of mAb A32, N5-i5, N60-i3, JR4 and 2.2c to the FLSC, gp120 and ID1 as measured by SPR. The assay was run by passing the FLSC [45] monomeric full length gp120$_{BaL}$ or ID1 over the immobilized antibody at 0-200 nM concentrations. The binding kinetics (association rates ($k_a$), dissociation rates ($k_d$), and affinity constants ($K_D$)) were calculated with the BIAevaluation software. Standard deviations of $k_a$, $k_d$ and $K_D$ for two experiments are shown.

| | gp120$_{BaL}$ | FLSC | fold change | ID1 | fold change[1] | fold change[2] |
|---|---|---|---|---|---|---|
| mAb A32 | | | | | | |
| $K_D$ (M) × $10^{-9}$ | 3.2 ± 0.07 | 0.23 ± 0.01 | 13.9 | 9.30 ± 1.10 | 2.9 | 40.4 |
| $k_a$ (1/Ms) × $10^5$ | 1.39 ± 0.02 | 4.43 ± 0.01 | 3.2 | 0.85 ± 0.04 | 1.6 | 5.2 |
| $k_d$ (1/s) × $10^{-5}$ | 43.7 ± 0.99 | 10.2 ± 0.09 | 4.3 | 78.50 ± 5.20 | 1.8 | 7.7 |
| mAb N5-i5 | | | | | | |
| $K_D$ (M) × $10^{-9}$ | 5.03 ± 0.03 | 0.29 ± 0.14 | 17.3 | 1.10 ± 0.16 | 4.6 | 3.8 |
| $k_a$ (1/Ms) × $10^5$ | 0.72 ± 0.01 | 8.25 ± 2.50 | 11.5 | 4.50 ± 1.00 | 6.3 | 1.8 |
| $k_d$ (1/s) × $10^{-5}$ | 36.0 ± 0.28 | 23.8 ± 13.80 | 1.5 | 48.30 ± 4.30 | 1.3 | 2.0 |
| mAb N60-i3 | | | | | | |
| $K_D$ (M) × $10^{-9}$ | 2.03 ± 0.07 | 0.25 ± 0.01 | 8.0 | 3.50 ± 0.13 | 1.7 | 13.8 |
| $k_a$ (1/Ms) × $10^5$ | 2.53 ± 0.06 | 12.4 ± 0.00 | 4.9 | 4.30 ± 0.25 | 1.7 | 2.9 |
| $k_d$ (1/s) × $10^{-5}$ | 51.2 ± 0.50 | 31.4 ± 0.71 | 1.6 | 148 ± 2.70 | 2.9 | 4.7 |
| mAb JR4 | | | | | | |
| $K_D$ (M) × $10^{-9}$ | 2.34 ± 0.16 | 0.18 ± 0.01 | 13.0 | 6.00 ± 0.33 | 2.6 | 33.3 |
| $k_a$ (1/Ms) × $10^5$ | 2.62 ± 0.09 | 6.43 ± 0.06 | 2.5 | 1.60 ± 0.10 | 1.6 | 4 |
| $k_d$ (1/s) × $10^{-5}$ | 61.1 ± 1.80 | 11.6 ± 0.28 | 5.3 | 94.40 ± 0.60 | 1.5 | 8.1 |
| mAb 2.2c | | | | | | |
| $K_D$ (M) × $10^{-9}$ | 12.00 ± 0.07 | 0.50 ± 0.06 | 24.0 | 3.00 ± 0.30 | 4 | 6.0 |
| $k_a$ (1/Ms) × $10^5$ | 0.73 ± 0.01 | 11.5 ± 1.40 | 15.7 | 2.70 ± 0.16 | 3.7 | 4.3 |
| $k_d$ (1/s) × $10^{-5}$ | 87.5 ± 1.10 | 55.6 ± 14.40 | 1.6 | 80.30 ± 2.40 | 1.1 | 1.4 |

[1] fold change relative to gp120,
[2] fold change relative to FLSC

5. Structure Based Design of ID2 and Evaluation of its Antigenic Properties

Figure 12A:
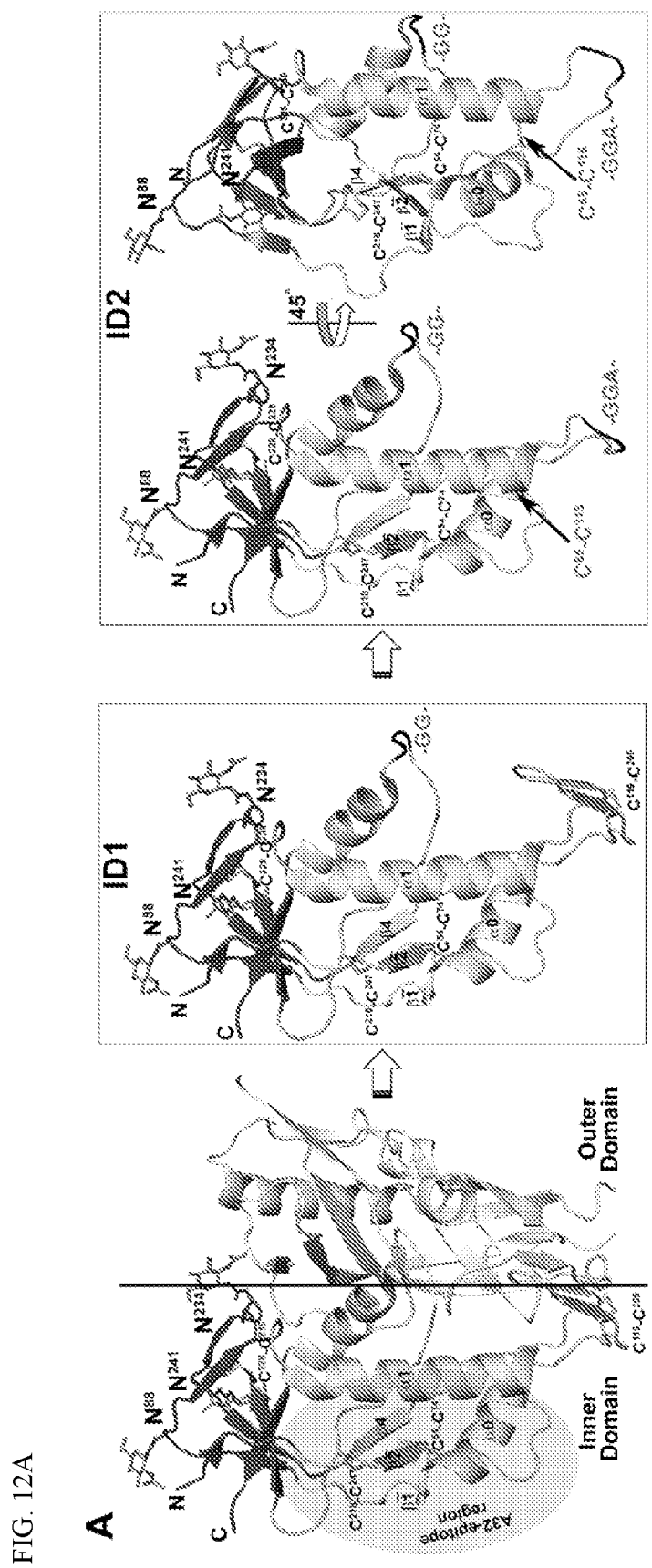
Figure 12B:
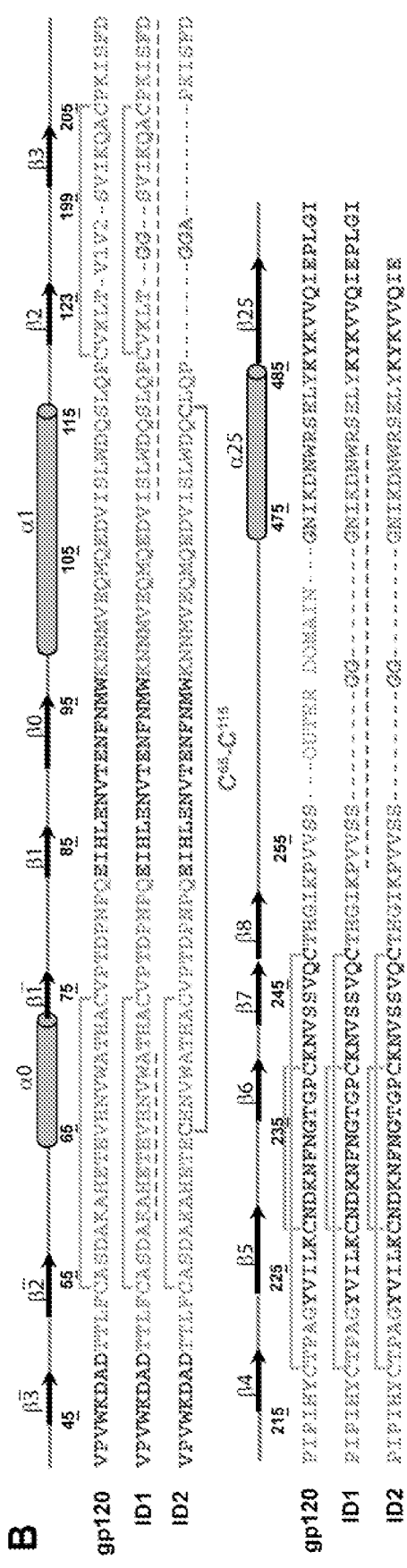
Figure 13A:
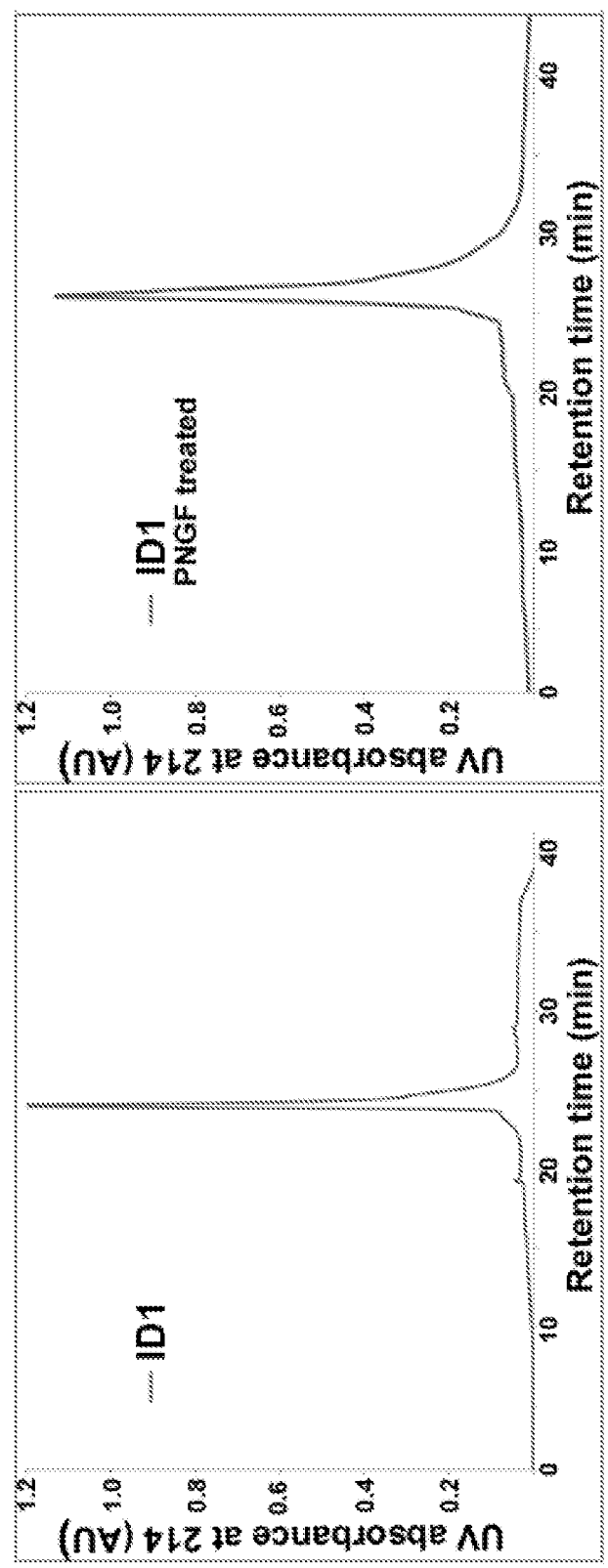
Figure 13B:
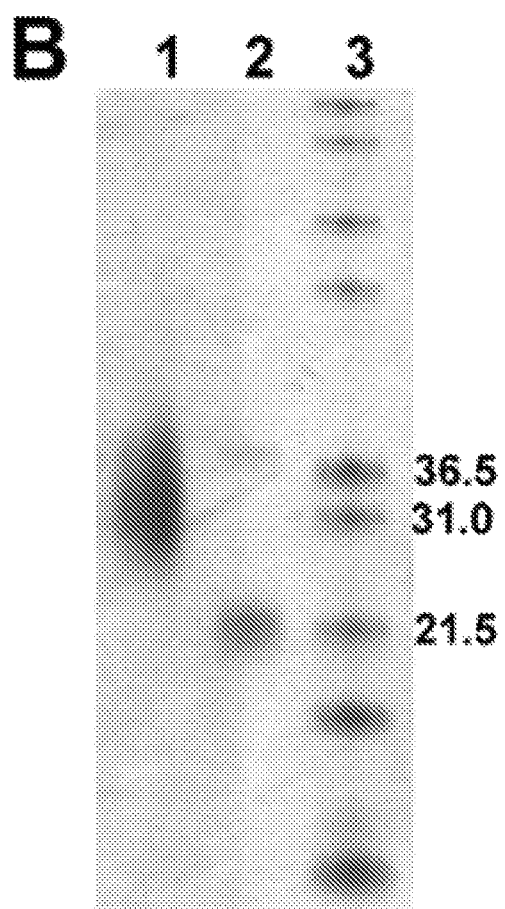

Structural analysis of ID1 complexed with the Fab of JR4, a C1-C2 specific mAb recognizing the A32-C11 mixed epitope within Cluster A region [83] revealed that conformational CD4i epitopes of the A32-like region are not fully formed within ID1 design with regions around V1V2 stem and α0-helix flexible and not contributing to anti-Cluster A mAb binding. In gp120 core$_e$ structures, the shortened V1V2 loop forms half of the bridging sheet, but in ID1 it forms a flexible loop that probably contributes to the disorder seen in layers 1 and 2 (FIG. 12). Therefore, a second inner domain immunogen was designed to remove this disorder with 12 additional residues of the V1V2 loop removed as shown in FIG. 12. This initial revision of the inner domain which had C119-C205 disulfide bond at the base of the V1V2 loop removed expressed well but showed a reduced affinity for A32-like antibodies as measured by SPR (data not shown). It was hypothesized that adding a disulfide bond at the bases of α0- and α1-helix could restore and preserve CD4i epitopes in this region (FIG. 12). Therefore, positions $V_{65}$ and $S_{115}$ were mutated to cysteines to form a single disulfide bond at the α0- and α1-helix junction. Similar mutations have been shown to increase CD4i epitope exposure in context of full length gp120 [75]. This revised second independent inner domain molecule design with V1/V2 stem removed and stabilized by C65-C115 disulfide bond was designated "ID2". ID2 was expressed in mammalian cells and purified. ID2 protein (SEQ ID NO:57) similar to ID1 contains 8 cysteines forming four disulfide bonds and folds into one disulfide-bonded form with no additional misfolded/different disulfide isomers. Expression yields of ID2 in 293T cells were typically comparable with ID1 expression with 1-2 mg of protein per liter of culture. The affinity of ID2 for the panel of anti-Cluster A mAbs was tested using SPR (FIG. 14, Table 6).

TABLE 6

Binding kinetics of mAb A32, N5-i5, N60-i3, JR4 and 2.2c to the FLSC, gp120 and ID2 as measured by SPR. The assay was run by passing the FLSC [45] monomeric full length gp120$_{BaL}$ or ID2 over the immobilized antibody at 0-200 nM concentrations. The binding kinetics (association rates ($k_a$), dissociation rates ($k_d$), and affinity constants ($K_D$)) were calculated with the BIAevaluation software. Standard deviations of $k_a$, $k_d$ and $K_D$ for two experiments are shown.

| 93TH057 | gp120$_{BaL}$ | FLSC | fold change | ID2 $C_{65}$-$C_{115}$ | fold change[1] | fold change[2] |
|---|---|---|---|---|---|---|
| mAb A32 | | | | | | |
| $K_D$ (M) × $10^{-9}$ | 3.2 ± 0.07 | 0.23 ± 0.01 | 13.9 | 0.17 ± 0.01 | 18.8 | 1.4 |
| $k_a$ (1/Ms) × $10^5$ | 1.39 ± 0.02 | 4.43 ± 0.01 | 3.2 | 16.5 ± 0.6 | 11.9 | 3.7 |
| $k_d$ (1/s) × $10^{-5}$ | 43.7 ± 0.99 | 10.2 ± 0.09 | 4.3 | 27.5 ± 2.0 | 1.6 | 2.7 |

TABLE 6-continued

Binding kinetics of mAb A32, N5-i5, N60-i3, JR4 and 2.2c to the FLSC, gp120 and ID2 as measured by SPR. The assay was run by passing the FLSC [45] monomeric full length gp120$_{BaL}$ or ID2 over the immobilized antibody at 0-200 nM concentrations. The binding kinetics (association rates ($k_a$), dissociation rates ($k_d$), and affinity constants ($K_D$)) were calculated with the BIAevaluation software. Standard deviations of $k_a$, $k_d$ and $K_D$ for two experiments are shown.

| 93TH057 | gp120$_{BaL}$ | FLSC | fold change | ID2 C$_{65}$-C$_{115}$ | fold change[1] | fold change[2] |
|---|---|---|---|---|---|---|
| mAb N5-i5 | | | | | | |
| $K_D$ (M) × 10$^{-9}$ | 5.03 ± 0.03 | 0.29 ± 0.14 | 17.3 | 0.14 ± 0.01 | 35.9 | 2.1 |
| $k_a$ (1/Ms) × 10$^5$ | 0.72 ± 0.01 | 8.25 ± 2.50 | 11.5 | 8.1 ± 0.2 | 11.3 | 1.0 |
| $k_d$ (1/s) × 10$^{-5}$ | 36.0 ± 0.28 | 23.8 ± 13.80 | 1.5 | 11.6 ± 0.4 | 3.1 | 2.1 |
| mAb N60-i3 | | | | | | |
| $K_D$ (M) × 10$^{-9}$ | 2.03 ± 0.07 | 0.25 ± 0.01 | 8.0 | 0.55 ± 0.01 | 3.7 | 2.2 |
| $k_a$ (1/Ms) × 10$^5$ | 2.53 ± 0.06 | 12.4 ± 0.00 | 4.9 | 8.9 ± 0.1 | 3.5 | 1.4 |
| $k_d$ (1/s) × 10$^{-5}$ | 51.2 ± 0.50 | 31.4 ± 0.71 | 1.6 | 49.1 ± 0.8 | 1.0 | 1.6 |
| mAb JR4 | | | | | | |
| $K_D$ (M) × 10$^{-9}$ | 2.34 ± 0.16 | 0.18 ± 0.01 | 13.0 | 2.9 ± 0.1 | 1.2 | 16.1 |
| $k_a$ (1/Ms) × 10$^5$ | 2.62 ± 0.09 | 6.43 ± 0.06 | 2.5 | 6.5 ± 0.6 | 2.5 | 1.0 |
| $k_d$ (1/s) × 10$^{-5}$ | 61.1 ± 1.80 | 11.6 ± 0.28 | 5.3 | 190.0 ± 9.9 | 3.1 | 16.4 |
| mAb 2.2c | | | | | | |
| $K_D$ (M) × 10$^{-9}$ | 12.00 ± 0.07 | 0.50 ± 0.06 | 24.0 | 0.19 ± 0.02 | 63.1 | 2.6 |
| $k_a$ (1/Ms) × 10$^5$ | 0.73 ± 0.01 | 11.5 ± 1.40 | 15.7 | 8.8 ± 0.28 | 12.1 | 1.3 |
| $k_d$ (1/s) × 10$^{-5}$ | 87.5 ± 1.10 | 55.6 ± 14.40 | 1.6 | 17.0 ± 2.6 | 5.1 | 3.3 |

[1]fold change relative to gp120,
[2]fold change relative to FLSC

Figure 14A:
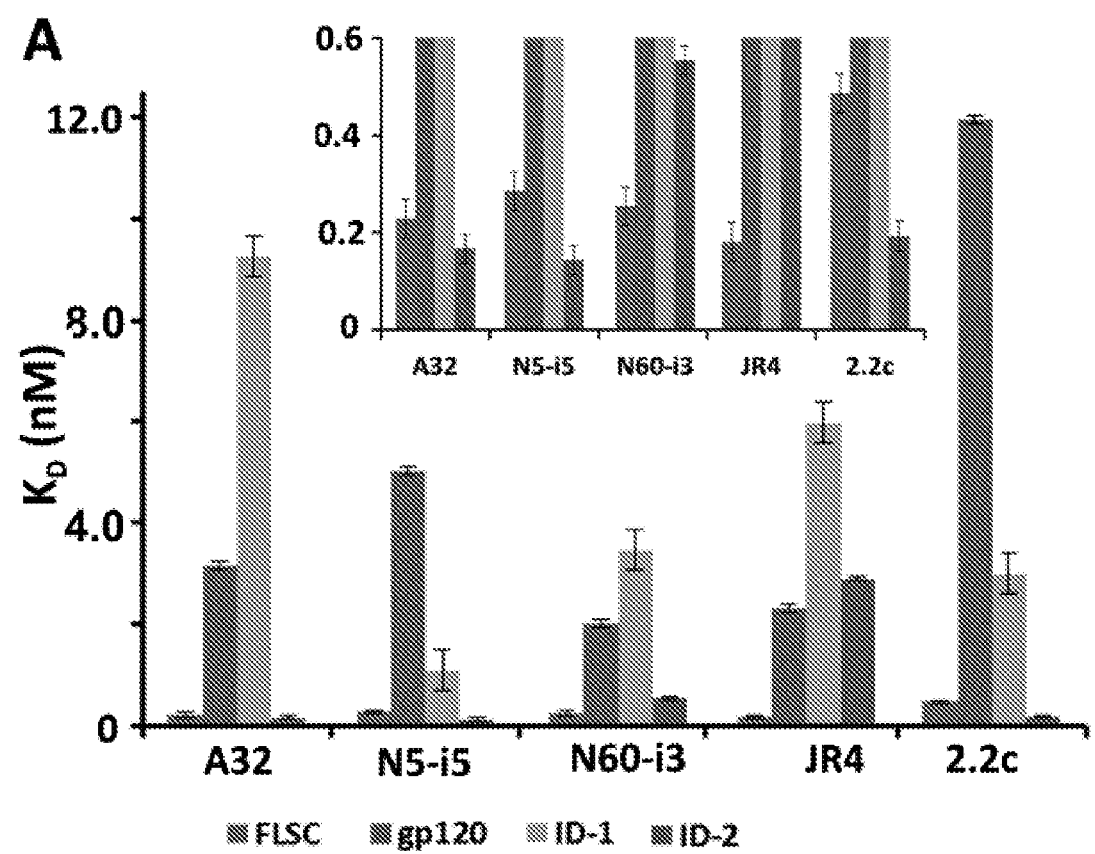
Figure 14B:
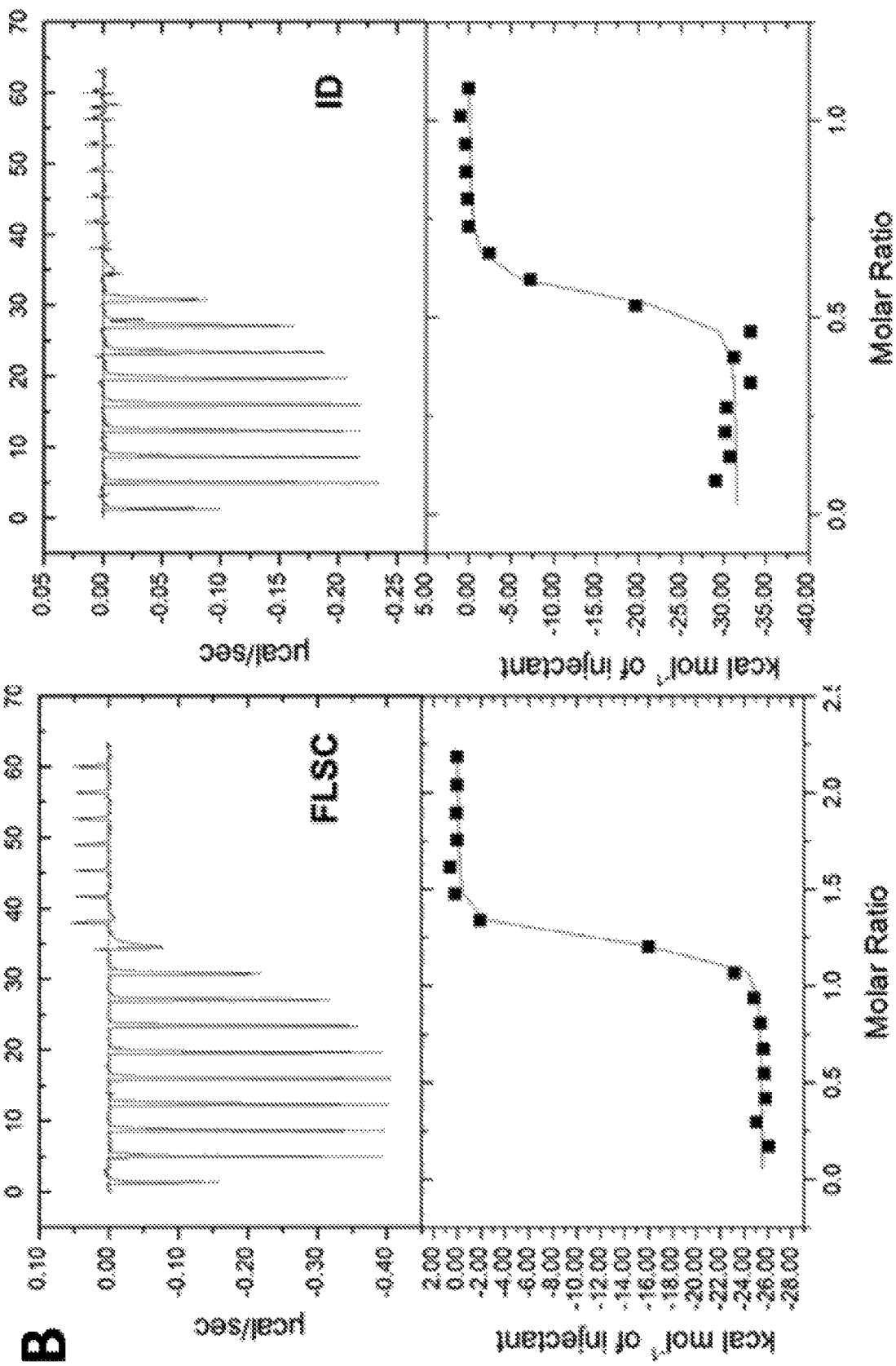

As can be seen, ID2 bound the panel of mAbs tested with an average of 17-fold tighter affinities that ID1, and similar or higher than those of FLSC (FIG. 14A). The increase in affinity was largely attributable to an increase in $k_a$ for the complex and to a lesser extent a decrease in $k_d$ suggesting that ID2 more closely resembles the CD4-triggered conformation of gp120 recognized by these antibodies. To additionally test if indeed ID2 is folded to stably present A32-like epitopes in solution, the binding of mAb A32 to ID2 was tested by Isothermal Titration calorimetry (ITC) and compared it to mAb A32 interaction with FLSC (FIG. 14B). These data clearly indicated that ID2 adopts the CD4-bound conformation in solution which closely resembles the presentation of A32-epitope as in context of CD4-triggered gp120. The binding kinetics of mAb A32 to ID2 and FLSC are very similar with $K_D$ value of 9.0 and 11.5 nM and ΔH of −2.553 (±0.18) and −3.15 (±0.69) kcal/mol for mAb A32-ID2 and mAb A32-FLSC interaction, respectively. All together these studies indicate that ID2 stably present the desired epitopes within the C1-C2 gp120 region and shows the antigenicity profile of the CD4-triggered gp120. ID2 represents the first stable design of inner domain expressed independently of outer domain and stabilized in CD4 bound confirmation to exclusively express the non-neutralizing ADCC epitopes of the C1-C2 region.

To additionally test if ID2 engrafts epitopes involved in ADCC function to the C1-C2 region, an ADCC competition assay was performed in which ADCC activities of anti-Cluster A mAbs against gp120 coated cells at the effective given concentration of 0.67 nM were tested in presence of increasing concentrations of ID2. ADCC measurements were performed using an RFADCC assay which is based on the rapid fluorimetric ADCC assay [84] optimized for high throughput efficiency. EGFP-CEM-NKr-CCR5-SNAP target cells (Orlandi C. et al., in preparation) were stained with SNAP-Surface Alexa Fluor 647 (BioLabs Cat. 591365) for 20 min at 37° C. with or without HIV-1$_{BaL}$gp120 (50 ug/ml). gp120-sensitized targets were then washed once with R10 medium and added to a 96-well V-bottom plate (5,000 cells/well).

Figure 15A:
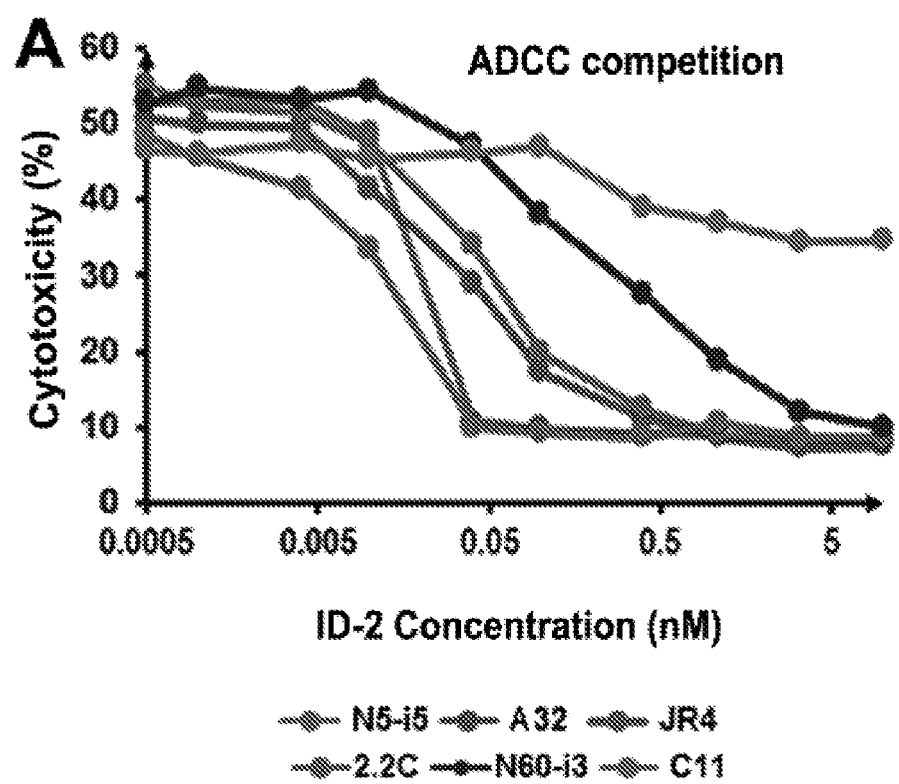

The results show that ID2 completely inhibited ADCC of all of the A32-like mAbs as well as the mixed A32-C11 mAb JR4 at a concentration range of 0.04-3 µg/ml (FIG. 15A). The ADCC activity of mAb C11 which recognizes an epitope involving residues of N- and C-termini and 7-stranded β-sandwich of gp120 not present within the ID design, is not affected. This indicates that ID2 is folded to stably display functional A32-like and mixed A32-C11-like epitopes recognized by anti-Cluster A mAbs capable of potent ADCC function.

Figure 15B:
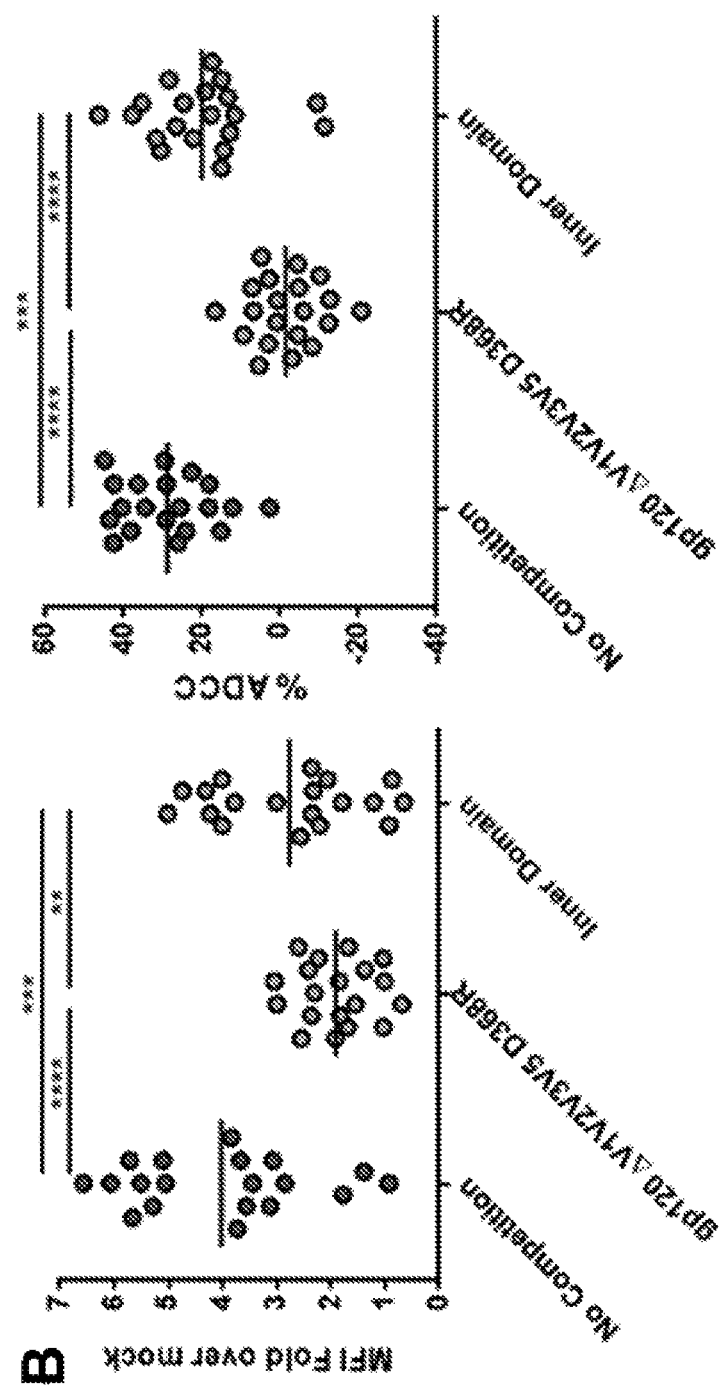

Next, whether ID2 could compete the ADCC activities of antibodies present in the sera of HIV-1 infected individuals was tested. It was shown previously that infected individuals frequently elicit antibodies specific for A32-like epitopes [41, 42, 43, 44, 48] and the predominant fraction of ADCC response in sera from HIV-1-infected individuals is directed at epitopes exposed on the CD4-triggered gp120 core including A32 sub-region [41,43]. Whether ID2 could bind to and block ADCC activity of antibodies present in sera of HIV-1 infected individuals was tested (FIG. 15B). Sera dilutions were pre-incubated with either purified soluble D368R gp120 dV1V2V3V5 as described in [41] and ID2 protein before being assayed for their ability to bind to CEM.NKr cells infected with Nef-Vpu-NL4.3 virus (FIG. 15B, left panel) and to mediate ADCC (FIG. 15B, right panel). ID2 specifically binds antibodies present in HIV-1 individuals and adsorbs on average approximately 30.5% of ADCC activity mediated by sera. This indicates that ID2 stably engrafts the CD4i epitopes recognized by antibodies involved in ADCC function present in sera of infected individuals.

6. Evaluation of Humoral Immune Response Induced by ID2 in Rabbits.

A group of three rabbits was immunized on weeks 0, 4 and 12 with 300 ug/dose of ID2 protein in IDRI-EM098 Emulsion with 0.04 mg/ml TLR4 agonist as adjuvant. Serum samples collected before (preimmune) and week 4, 8 and 15 were evaluated in ELISA to determine the elicitation of antibody against ID2 protein. Briefly, plates were coated with ID2 (1 µg/mL) in TBS at 4° C. overnight. After blocking for 1 hr with blocking buffer (5% dry milk and 0.1% Nonidet P-40 in TBS), 10-fold dilutions of rabbit sera starting at 1:10 were added to the plates. After washing with TBS-T buffer (TBS with 1% Tween-20), alkaline phosphatase (AP)-goat anti-rabbit IgG (H+L) (Southern Biotech; catalog no.) was added to the plates at a 1:1000 dilution and then detected with Blue Phos Microwell Phosphatase Substrate System (KPL 50-88-00). After 15 min, the reaction was stopped and plates were read at 620 nm. Reactions were considered positive when the optical density (OD) measured by the ELISA was higher than the O.D.+3SD of the same dilution of pre-immunization sera.

Figure 16:
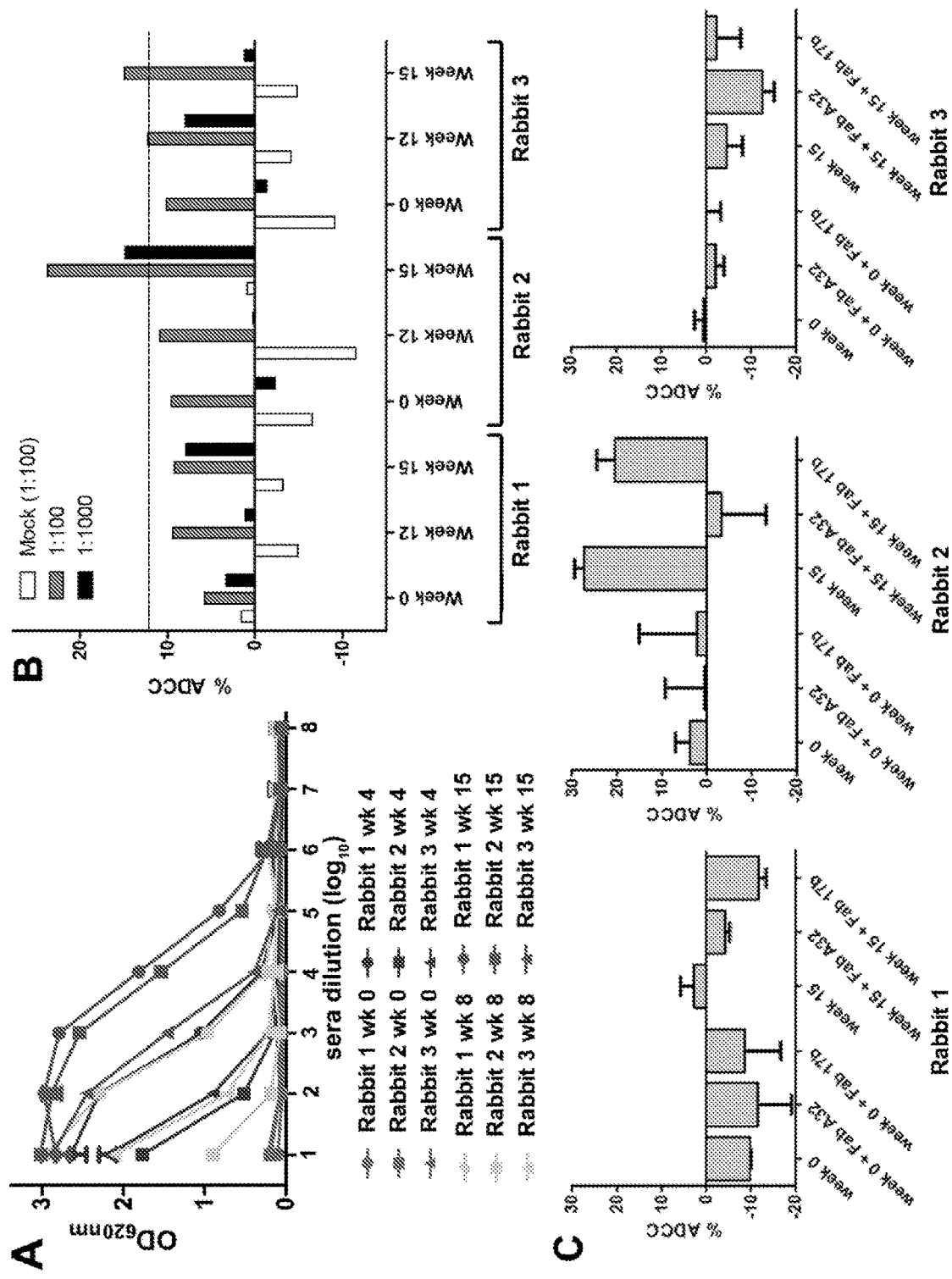

All three rabbits showed anti-ID2 specific antibodies already after the first immunization with titers ranging from 1:100 (Rabbit 2 and 3) to 1:10.000 (Rabbit 1). At week 15, after 3 immunizations, animals showed two log increase in anti-ID2 specific antibodies titers (titers of 1:100.000 and 1:10.000 for Rabbit 1/Rabbit 2 and 3 respectively). The increase in antibodies titer was statistically significant for all 3 animals as determined by unpaired t test ($p<0.005$ for Rabbit 1 and $p<0.05$ for Rabbit 2 and 3). Although all three rabbits mounted anti-ID2 response, only sera of two (rabbit 2 and 3) after three immunizations had antibodies directed at the desired CD4i Cluster A gp120 epitopes. As shown in FIG. 16B, sera from immunized rabbit 2 and 3 at week 15 were able to effectively recognize and bind to the HIV-1 gp120$_{YU2}$-coated CEM.NKr cells, cells developed to express the target cell-bound gp120 Env epitopes and used as suitable targets to evaluate ADCC response specific for CD4-bound conformation of HIV-1 [80].

Figure 17:
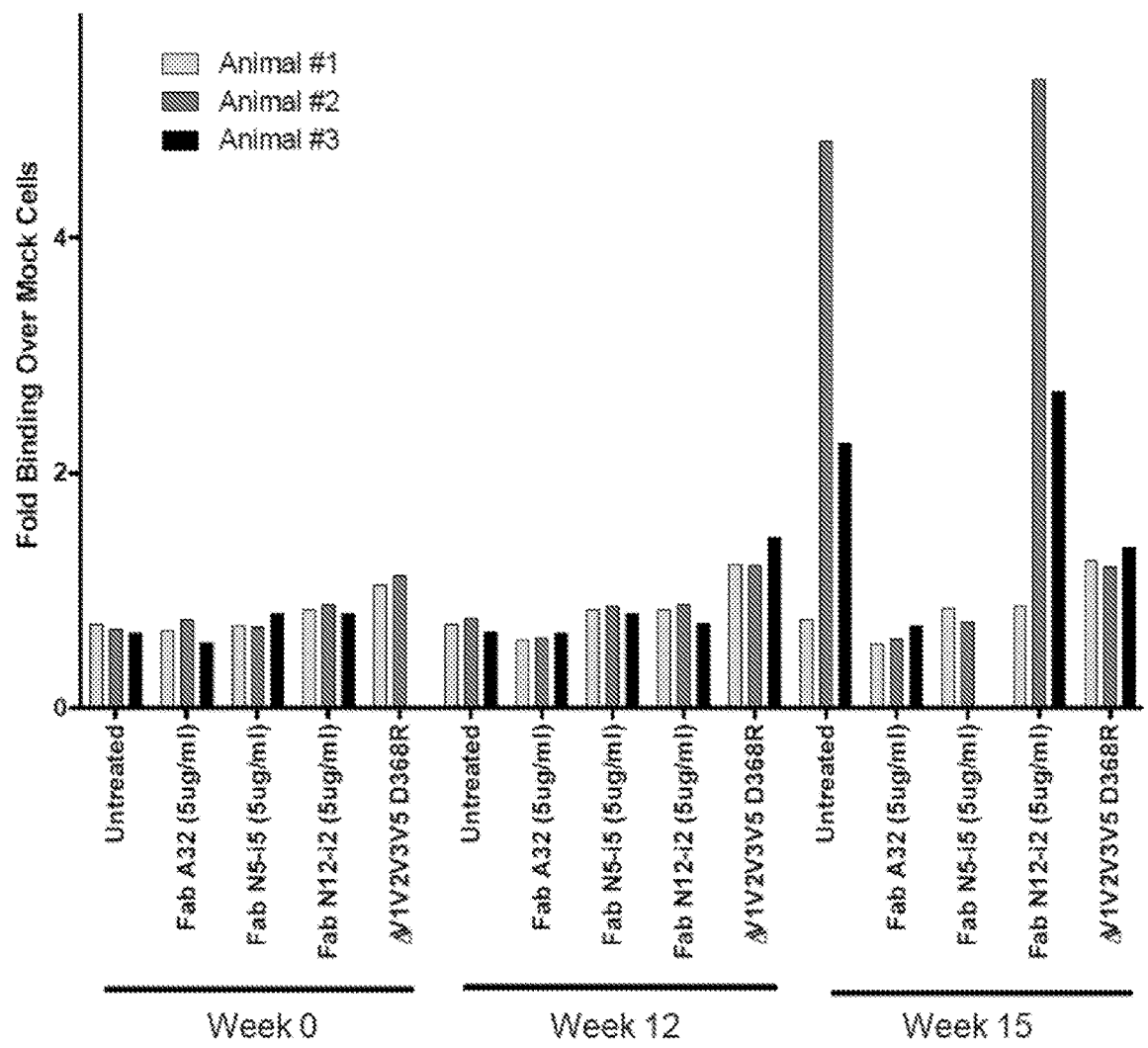

In addition, antibodies elicited in these two rabbits were directed specifically against the epitopes in the Cluster A region. As shown in FIG. 17, the sera binding to HIV-1 gp120$_{YU2}$-coated CEM.NKr cells was abrogated entirely by ΔV1V2V3V5 D368R gp120, a gp120 core protein stabilized in CD4 bound conformation [41] and Fabs of either of two anti-Cluster A mAbs tested, mAb A32 or N5-i5 [44]. In contrast, the binding was not affected by pre-treating of gp120-coated cells with Fab of mAb N12-i2, CD4i antibody recognizing epitope in the co-receptor binding side region [44]. Finally, the overall ADCC activity potential in the 15$^{th}$-week sera of immunized rabbits was tested using the previously described fluorescence-activated cell sorting (FACS)-based ADCC assay [48,80] against CEM.NKr cells coated with HIV-1 gp120$_{YU2}$ or infected with HIV-1 lacking Nef and Vpu (N-U-) (FIGS. 16C and D). The cells infected with a virus lacking both accessory proteins Nef and Vpu were shown previously to be unable to down-regulate CD4 on the target cell surface thus more susceptible to ADCC killing by CD4i antibodies [41]. Sera of both animal 2 and 3 was capable of ADCC against gp120$_{YU2}$-coated coated cells (FIG. 16C) with animal 2 sera showing ADCC potencies comparable with ADCC mediated by sera from HIV-infected individuals [41]. Furthermore, sera of rabbit 2 showed effective ADCC killing of cells infected with HIV-1 lacking Nef and Vpu. Moreover, although by design ID2 is not bearing known neutralizing epitopes, neutralizing activity of sera from pre- and post-3th immunization was tested against easy-to-neutralize tier 1 virus, SF162.LS MN.3 As expected (results not shown), no neutralizing activity was detected in any of sample sera. These results indicate that ID2 is immunogenic in an animal host, capable of inducing specific FcR-mediated humoral response directed at the desired A32 epitope sub-region without neutralizing activities.

7. Design of Additional ID Immunogens.

Based on the results from the earlier studies, additional ID immunogens were prepared that comprise the gp120 core sequence with the following additional features:
1) 11-amino acid deletion (residues 31-42 according to gp120 sequence numbering of HXBc2 isolate; SEQ ID NO:2) at the N-terminus;
2) Cys point mutations at position 65 and 115 (numbering according to gp120 sequence of HXBc2 isolate; SEQ ID NO:2) introducing extra $C_{65}$-$C_{115}$ disulfide;
3) -GlyGly-dipeptide linker replacing residues 258-472 (numbering according to gp120 sequence of HXBc2 isolate; SEQ ID NO:2) of outer domain; and, in some cases,
4) -GlyGlyAla-linker encoding for residues 119-205 (numbering according to gp120 sequence of HXBc2 isolate; SEQ ID NO:2) in V1V2 loop.

The design was applied to gp120 from a number of different HIV-1 clades and strains. In Table 5, the first column provides the clade, the second column provides the strain, the third column provides those features defined in the paragraphs above found in the immunogen, and the fourth column provides the sequence identifier for the immunogen in the sequence listing.

TABLE 5

| Clade | Strain | Features | Sequence Identifier |
|---|---|---|---|
| A1_VIV2 | N/A | 1)-3) | SEQ ID NO: 3 |
| A2_VIV2 | N/A | 1)-3) | SEQ ID NO: 4 |
| B_VIV2 | N/A | 1)-3) | SEQ ID NO: 5 |
| C_VIV2 | N/A | 1)-3) | SEQ ID NO: 6 |
| D_VIV2 | N/A | 1)-3) | SEQ ID NO: 7 |
| F1_VIV2 | N/A | 1)-3) | SEQ ID NO: 8 |
| F2_VIV2 | N/A | 1)-3) | SEQ ID NO: 9 |
| G_VIV2 | N/A | 1)-3) | SEQ ID NO: 10 |
| H_VIV2 | N/A | 1)-3) | SEQ ID NO: 11 |
| 01_AE_VIV2 | N/A | 1)-3) | SEQ ID NO: 12 |
| 02_AG_VIV2 | N/A | 1)-3) | SEQ ID NO: 13 |
| 03_AB_VIV2 | N/A | 1)-3) | SEQ ID NO: 14 |
| 04_CPX_VIV2 | N/A | 1)-3) | SEQ ID NO: 15 |
| 06_CPX_VIV2 | N/A | 1)-3) | SEQ ID NO: 16 |
| 08_BC_VIV2 | N/A | 1)-3) | SEQ ID NO: 17 |
| 10_CD_VIV2 | N/A | 1)-3) | SEQ ID NO: 18 |
| 11_CPX_VIV2 | N/A | 1)-3) | SEQ ID NO: 19 |
| 12_BF_VIV2 | N/A | 1)-3) | SEQ ID NO: 20 |

TABLE 5-continued

| Clade | Strain | Features | Sequence Identifier |
|---|---|---|---|
| 14_BG_VIV2 | N/A | 1)-3) | SEQ ID NO: 21 |
| CON_OF_CONS_VIV2 | N/A | 1)-3) | SEQ ID NO: 22 |
| A | AB097872_VIV2 | 1)-3) | SEQ ID NO: 23 |
| A | AB052867_VIV2 | 1)-3) | SEQ ID NO: 24 |
| B | yu2gp120_VIV2 | 1)-3) | SEQ ID NO: 25 |
| B | HXB2_VIV2 | 1)-3) | SEQ ID NO: 26 |
| C | HM623558_VIV2 | 1)-3) | SEQ ID NO: 27 |
| C | DQ404010_VIV2 | 1)-3) | SEQ ID NO: 28 |
| A1 | N/A | 1)-4) | SEQ ID NO: 29 |
| A2 | N/A | 1)-4) | SEQ ID NO: 30 |
| B | N/A | 1)-4) | SEQ ID NO: 31 |
| C | N/A | 1)-4) | SEQ ID NO: 32 |
| D | N/A | 1)-4) | SEQ ID NO: 33 |
| F1 | N/A | 1)-4) | SEQ ID NO: 34 |
| F2 | N/A | 1)-4) | SEQ ID NO: 35 |
| G | N/A | 1)-4) | SEQ ID NO: 36 |
| H | N/A | 1)-4) | SEQ ID NO: 37 |
| 01_AE | N/A | 1)-4) | SEQ ID NO: 38 |
| 02_AG | N/A | 1)-4) | SEQ ID NO: 39 |
| 03_AB | N/A | 1)-4) | SEQ ID NO: 40 |
| 04_CPX | N/A | 1)-4) | SEQ ID NO: 41 |
| 06_CPX | N/A | 1)-4) | SEQ ID NO: 42 |
| 08_BC | N/A | 1)-4) | SEQ ID NO: 43 |
| 10_CD | N/A | 1)-4) | SEQ ID NO: 44 |
| 11_CPX | N/A | 1)-4) | SEQ ID NO: 45 |
| 12_BF | N/A | 1)-4) | SEQ ID NO: 46 |
| 14_BG | N/A | 1)-4) | SEQ ID NO: 47 |
| CON_OF_CONS | N/A | 1)-4) | SEQ ID NO: 48 |
| A | AB097872 | 1)-4) | SEQ ID NO: 49 |
| A | AB052867 | 1)-4) | SEQ ID NO: 50 |
| B | yu2gp120 | 1)-4) | SEQ ID NO: 51 |
| B | HXB2 | 1)-4) | SEQ ID NO: 52 |
| C | HM623558 | 1)-4) | SEQ ID NO: 53 |
| C | DQ404010 | 1)-4) | SEQ ID NO: 54 |

The Δ11 deletion at the inner domain N-terminus was introduced initially to follow up with the previously reported data on overall enhanced antigenicity and immunogenicity (also to the gp120 C1 region) of the RV144 A244 gp120 immunogen which was modified by the same N-terminal deletion [74]. In addition, a group of the immunogens was designed to contain deletion of V1V2 loop and 'locked' in a CD4 bound state by a single $C_{65}$-$C_{115}$ disulfide bond, which brings together layer 1 and 2 within the C1/C2 epitope surface. It was shown previously that $C_{65}$-$C_{115}$ disulfide locks monomeric gp120 in CD4 bound state [75]. Rabbits immunized with $C_{65}$-$C_{115}$ disulfide-stabilized monomeric gp120 elicit a higher proportion of antibodies directed against both CD4i and CD4 binding site epitopes than the wild-type protein [75].

While the invention has been described with reference to certain particular embodiments thereof, those skilled in the art will appreciate that various modifications may be made without departing from the spirit and scope of the invention. The scope of the appended claims is not to be limited to the specific embodiments described.

REFERENCES

All patents and publications mentioned in this specification are indicative of the level of skill of those skilled in the art to which the invention pertains. Each cited patent and publication is incorporated herein by reference in its entirety. All of the following references have been cited in this application:

1. Willey S & AasaChapman M M (2008) Humoral immunity to HIV1: neutralisation and antibody effector functions. *Trends Microbiol* 16(12):596-604.
2. Takai T (2002) Roles of Fc receptors in autoimmunity. *Nat Rev Immunol* 2(8):580-592.
3. Nimmerjahn F & Ravetch J V (2008) Analyzing antibody Fc-receptor interactions. *Methods Mol Biol* 415:151-162.
4. Sulica A, Morel P, Metes D, & Herberman RB (2001) Ig-binding receptors on human NK cells as effector and regulatory surface molecules. *Int Rev Immunol* 20(34): 371-414.
5. Mikell I, et al. (2011) Characteristics of the earliest crossneutralizing antibody response to HIV1. *PLoS Pathog* 7(1):e1001251.
6. Florese R H, et al. (2009) Contribution of nonneutralizing vaccine-elicited antibody activities to improved protective efficacy in rhesus macaques immunized with Tat/Env compared with multigenic vaccines. *J Immunol* 182(6): 3718-3727.
7. Sawyer L A, et al. (1990) Possible beneficial effects of neutralizing antibodies and antibody-dependent, cell-mediated cytotoxicity in human immunodeficiency virus infection. *AIDS Res Hum Retroviruses* 6(3):341-356.
8. Richman D D, Wrin T, Little S J, & Petropoulos C J (2003) Rapid evolution of the neutralizing antibody response to HIV type 1 infection. *Proc Natl Acad Sci USA* 100(7):4144-4149.
9. Permar S R, et al. (2010) Limited contribution of mucosal IgA to Simian immunodeficiency virus (SIV)specific neutralizing antibody response and virus envelope evolution in breast milk of SIV-infected, lactating rhesus monkeys. *J Virol* 84(16):8209-8218.
10. Sun Y, et al. (2011) Antibody-dependent cell-mediated cytotoxicity in simian immunodeficiency virus-infected rhesus monkeys. *J Virol* 85(14):6906-6912.
11. Asmal M, et al. (2011) Antibody-dependent cell-mediated viral inhibition emerges after simian immunodeficiency virus SIVmac251 infection of rhesus monkeys coincident with gp140-binding antibodies and is effective against neutralization-resistant viruses. *J Virol* 85(11): 5465-5475.

12. Pollara J J, Laster S M, & Petty I T (2010) Inhibition of poxvirus growth by Terameprocol, a methylated derivative of nordihydroguaiaretic acid. *Antiviral Res* 88(3): 287-295.
13. Koup R A, et al. (1991) Antibody-dependent cell-mediated cytotoxicity directed by a human monoclonal antibody reactive with gp120 of HIV1. *Aids* 5(11):1309-1314.
14. Lyerly H K, et al. (1987) Anti-GP 120 antibodies from HIV seropositive individuals mediate broadly reactive anti-HIV ADCC. *AIDS Res Hum Retroviruses* 3(4):409-422.
15. Baum L L, et al. (1996) HIV1 gp120-specific antibodydependent cell-mediated cytotoxicity correlates with rate of disease progression. *J Immunol* 157(5):2168-2173.
16. Wren L H, et al. (2013) Specific antibodydependent cellular cytotoxicity responses associated with slow progression of HIV infection. *Immunology* 138(2):116-123.
17. Jia M, et al. (2013) Impaired natural killer cell-induced antibody-dependent cell-mediated cytotoxicity is associated with human immunodeficiency virus-1 disease progression. *Clin Exp Immunol* 171(1):107-116.
18. Fouda G G, et al. (2011) HIV-specific functional antibody responses in breast milk mirror those in plasma and are primarily mediated by IgG antibodies. *Journal of virology* 85(18):9555-9567.
19. Lambotte O, et al. (2009) Heterogeneous neutralizing antibody and antibody-dependent cell cytotoxicity responses in HIV1 elite controllers. *AIDS* 23(8):897-906.
20. Mabuka J, Nduati R, OdemDavis K, Peterson D, & Overbaugh J (2012) HIV-specific antibodies capable of ADCC are common in breastmilk and are associated with reduced risk of transmission in women with high viral loads. *PLoS Pathog* 8(6):e1002739.
21. Forthal D N, Gilbert P B, Landucci G, & Phan T (2007) Recombinant gp120 vaccine-induced antibodies inhibit clinical strains of HIV1 in the presence of Fc receptor-bearing effector cells and correlate inversely with HIV infection rate. *J Immunol* 178(10):6596-6603.
22. Banks N D, Kinsey N, Clements J, & Hildreth J E (2002) Sustained antibody-dependent cell-mediated cytotoxicity (ADCC) in SIV-infected macaques correlates with delayed progression to AIDS. *AIDS Res Hum Retroviruses* 18(16):1197-1205.
23. He X, et al. (2013) Compromised NK Cell-Mediated Antibody-Dependent Cellular Cytotoxicity in Chronic SIV/SHIV Infection. *PLoS One* 8(2):e56309.
24. GomezRoman V R, et al. (2005) Vaccine-elicited antibodies mediate antibody-dependent cellular cytotoxicity correlated with significantly reduced acute viremia in rhesus macaques challenged with SIVmac251. *J Immunol* 174(4):2185-2189.
25. Hidajat R, et al. (2009) Correlation of vaccine-elicited systemic and mucosal non-neutralizing antibody activities with reduced acute viremia following intrarectal simian immunodeficiency virus SIVmac251 challenge of rhesus macaques. *J Virol* 83(2):791-801.
26. Xiao P, et al. (2010) Multiple vaccine-elicited non-neutralizing anti-envelope antibody activities contribute to protective efficacy by reducing both acute and chronic viremia following simian/human immunodeficiency virus SHIV89.6P challenge in rhesus macaques. *J Virol* 84(14): 7161-7173.
27. Alpert M D, et al. (2012) ADCC Develops Over Time during Persistent Infection with Live-Attenuated SIV and Is Associated with Complete Protection against SIV(mac) 251 Challenge. *PLoS Pathog* 8(8):e1002890.
28. BroccaCofano E, et al. (2011) Vaccine-elicited SIV and HIV envelope-specific IgA and IgG memory B cells in rhesus macaque peripheral blood correlate with functional antibody responses and reduced viremia. *Vaccine* 29(17): 3310-3319.
29. Hessell A J, et al. (2007) Fc receptor but not complement binding is important in antibody protection against HIV. *Nature* 449(7158):101-104.
30. Hessell A J, et al. (2009) Effective, low-titer antibody protection against low-dose repeated mucosal SHIV challenge in macaques. *Nat Med* 15(8):951-954.
31. Moog C, et al. (2014) Protective effect of vaginal application of neutralizing and non-neutralizing inhibitory antibodies against vaginal SHIV challenge in macaques. *Mucosal immunology* 7(1):46-56.
32. RerksNgarm S, et al. (2009) Vaccination with ALVAC and AIDSVAX to prevent HIV1 infection in Thailand. *N Engl J Med* 361(23):2209-2220.
33. Haynes B F, et al. (2012) Immune-correlates analysis of an HIV1 vaccine efficacy trial. *N Engl J Med* 366(14): 1275-1286.
34. Yates N L, et al. (2014) Vaccine-Induced Env V1V2 IgG3 Correlates with Lower HIV1 Infection Risk and Declines Soon After Vaccination. *PLoS One* 9(2):e87572.
35. Chung A W, et al. (2014) Polyfunctional Fc-Effector Profiles Mediated by IgG Subclass Selection Distinguish RV144 and VAX003 Vaccines. *Science Translational Medicine* 6(228):228ra238.
36. Bonsignori M, et al. (2012) Antibody-dependent cellular cytotoxicity-mediating antibodies from an HIV1 vaccine efficacy trial target multiple epitopes and preferentially use the VH1 gene family. *J Virol* 86(21):11521-11532.
37. Liao H X, et al. (2013) Vaccine Induction of Antibodies against a Structurally Heterogeneous Site of Immune Pressure within HIV1 Envelope Protein Variable Regions 1 and 2. *Immunity* 38(1):176-186.
38. Liu P, et al. (2013) Infectious Virion Capture by HIV1 gp120 Specific IgG from RV144 Vaccinees. *J Virol.* 87(14):7828-36.
39. Bonsignori M, et al. (2012) ADCC-Mediating Antibodies from an HIV1 Vaccine Efficacy Trial Target Multiple Epitopes and Preferentially Use the VH1 Gene Family. *J Virol* 86(21):11521-11532.
40. Tomaras G D, et al. (2013) Vaccine-induced plasma IgA specific for the C1 region of the HIV1 envelope blocks binding and effector function of IgG. *Proc Natl Acad Sci USA* 110(22):9019-9024.
41. Veillette M, Coutu M, Richard J, Batraville L A, Dagher O, Bernard N, Tremblay C, Kaufmann D E, Roger M, Finzi A. 2015. The HIV-1 gp120 CD4-bound conformation is preferentially targeted by antibody-dependent cellular cytotoxicity-mediating antibodies in sera from HIV-1-infected individuals. Journal of Virology 89:545-551.
42. Ampol S, Pattanapanyasat K, Sutthent R, Permpikul P, & Kantakamalakul W (2012) Comprehensive investigation of common antibody-dependent cell-mediated cytotoxicity antibody epitopes of HIV1 CRF01_AE gp120. AIDS Res Hum Retroviruses 28:1250-1258.
43. Ferrari G, Pollara J, Kozink D, Harms T, Drinker M, Freel S, Moody M A, Alam S M, Tomaras G D, Ochsenbauer C, Kappes J C, Shaw G M, Hoxie J A, Robinson J E, Haynes B F. 2011. An HIV-1 gp120 envelope human monoclonal antibody that recognizes a C1 conformational 44. Guan Y, et al. (2013) Diverse specificity and effector function among human antibodies to HIV1 envelope glycoprotein epitopes exposed by CD4 binding. *Proc Natl Acad Sci U S A* 110(1):E69-78.
45. York J, Nunberg J H. 2004. Role of hydrophobic residues in the central ectodomain of gp41 in maintaining the association between human immunodeficiency virus type 1 envelope glycoprotein subunits gp120 and gp41. Journal of virology 78:4921-4926.
46. Fouts T R, Tuskan R, Godfrey K, Reitz M, Hone D, Lewis G K, DeVico A L. 2000. Expression and characterization of a single-chain polypeptide analogue of the human immunodeficiency virus type 1 gp120-CD4 receptor complex. Journal of virology 74:11427-11436.
47. Lewis G K, et al. (2014) Epitope target structures of Fc-mediated effector function during HIV1 acquisition. *Curr Opin HIV AIDS* 9(3):263-70.
48. Veillette M, et al. (2014) Interaction with Cellular CD4 Exposes HIV1 Envelope Epitopes Targeted by Antibody-Dependent Cell-Mediated Cytotoxicity. *J Virol* 88(5): 2633-2644.
49. Pham T N, Lukhele S, Hajjar F, Routy J P, & Cohen E A (2014) HIV Nef and Vpu protect HIVinfected CD4+ T cells from antibody-mediated cell lysis through down-modulation of CD4 and BST2. *Retrovirology* 11(1):15.
50. Lewis G K (2013) Qualitative and quantitative variables that affect the potency of Fc mediated effector function in vitro and in vivo: considerations for passive immunization using non-neutralizing antibodies. *Curr HIV Res* 11(5): 354-364.
51. Pollara J, et al. (2013) Epitope specificity of human immunodeficiency virus1 antibody dependent cellular cytotoxicity [ADCC] responses. *Curr HIV Res* 11(5):378-387.
52. Finnegan C M, Berg W, Lewis G K, & DeVico A L (2001) Antigenic properties of the human immunodeficiency virus envelope during cell-cell fusion. *J Virol* 75(22):11096-11105.
53. Finnegan C M, Berg W, Lewis G K, & DeVico A L (2002) Antigenic properties of the human immunodeficiency virus transmembrane glycoprotein during cell-cell fusion. *J Virol* 76(23):12123-12134.
54. Finnegan C M, Berg W, Lewis G K, & DeVico A L (2001) Antigenic properties of the human immunodeficiency virus envelope during cell-cell fusion. *J Virol* 75(22):11096-11105.
55. Finnegan C M, Berg W, Lewis G K, & DeVico A L (2002) Antigenic properties of the human immunodeficiency virus transmembrane glycoprotein during cell-cell fusion. *J Virol* 76(23):12123-12134.
56. Nishimura Y, et al. (2003) Transfer of neutralizing IgG to macaques 6 h but not 24 h after SHIV infection confers sterilizing protection: implications for HIV1 vaccine development. *Proc Natl Acad Sci USA* 100(25):15131-15136.
57. Lewis G K (2010) Challenges of antibodymediated protection against HIV1. *Expert Rev Vaccines* 9(7):683-687.
58. Kim S Y, Byrn R, Groopman J, & Baltimore D (1989) Temporal aspects of DNA and RNA synthesis during human immunodeficiency virus infection: evidence for differential gene expression. *J Virol* 63(9):3708-3713.
59. Klotman M E, et al. (1991) Kinetics of expression of multiply spliced RNA in early human immunodeficiency virus type 1 infection of lymphocytes and monocytes. *Proc Natl Acad Sci USA* 88(11):5011-5015.
60. Sajadi M M, et al. (2011) Correlation between circulating HIV1 RNA and broad HIV1 neutralizing antibody activity. *J Acquir Immune Defic Syndr* 57(1):915.
61. Sajadi M M, Heredia A, Le N, Constantine N T, & Redfield R R (2007) HIV1 natural viral suppressors: control of viral replication in the absence of therapy. *Aids* 21(4):517-519.
62. Sajadi M M, et al. (2009) Epidemiologic characteristics and natural history of HIV1 natural viral suppressors. *J Acquir Immune Defic Syndr* 50(4):403-408.
63. GomezRoman V R, et al. (2006) A simplified method for the rapid fluorometric assessment of antibody-dependent cell-mediated cytotoxicity. *J Immunol Methods* 308(12): 53-67.
64. Prabakaran P, et al. (2012) Origin, diversity, and maturation of human antiviral antibodies analyzed by high-throughput sequencing. *Frontiers in microbiology* 3:277.
65. Briney B S, Willis J R, & Crowe J E, Jr. (2012) Human peripheral blood antibodies with long HCDR3s are established primarily at original recombination using a limited subset of germline genes. *PLoS One* 7(5):e36750.
66. Verkoczy L, Kelsoe G, Moody M A, & Haynes B F (2011) Role of immune mechanisms in induction of HIV1 broadly neutralizing antibodies. *Curr Opin Immunol* 23(3):383-390.
67. von Bubnoff A (2010) Vaccines to antibodies: grow up! *IAVI Rep* 14(4):49.
68. Liu J, Bartesaghi A, Borgnia M J, Sapiro G, & Subramaniam S (2008) Molecular architecture of native HIV1 gp120 trimers. *Nature* 455(7209):109-113.
69. Julien J P, et al. (2013) Crystal structure of a soluble cleaved HIV1 envelope trimer. *Science* 342(6165):1477-1483.
70. Lyumkis D, et al. (2013) CryoEM structure of a fully glycosylated soluble cleaved HIV1 envelope trimer. *Science* 342(6165):1484-1490.
71. Desormeaux A, et al. (2013) The Highly Conserved Layer3 Component of the HIV1 gp120 Inner Domain Is Critical for CD4-Required Conformational Transitions. *J Virol* 87(5):2549-2562.
72. Finzi A, et al. (2010) Topological layers in the HIV1 gp120 inner domain regulate gp41 interaction and CD4-triggered conformational transitions. *Mol Cell* 37(5):656-667.
73. Finzi A, et al. (2012) Lineage-specific differences between human and simian immunodeficiency virus regulation of gp120 trimer association and CD4 binding. *J Virol* 86(17):8974-8986.
74. Alam S M, et al. (2013) Antigenicity and immunogenicity of RV144 vaccine AIDSVAX clade E envelope immunogen is enhanced by a gp120 N-terminal deletion. *Journal of virology* 87(3):1554-1568.
75. Kassa A, et al. (2013) Stabilizing exposure of conserved epitopes by structure guided insertion of disulfide bond in HIV1 envelope glycoprotein. *PLoS One* 8(10):e76139.
76. Moore P L, et al. (2006) Nature of nonfunctional envelope proteins on the surface of human immunodeficiency virus type 1. *Journal of virology* 80(5):2515-2528.
77. Kwon Y D, Finzi A, Wu X, Dogo-Isonagie C, Lee L K, Moore L R, Schmidt S D, Stuckey J, Yang Y, Zhou T, Zhu J, Vicic D A, Debnath A K, Shapiro L, Bewley C A, Mascola J R, Sodroski J G, Kwong P D. 2012. Unliganded HIV-1 gp120 core structures assume the CD4-bound conformation with regulation by quaternary interactions and variable loops. Proc Natl Acad Sci USA 109:5663-5668.
78. Dey B, Svehla K, Xu L, Wycuff D, Zhou T, Voss G, Phogat A, Chakrabarti B K, Li Y, Shaw G, Kwong P D, Nabel G J, Mascola J R, Wyatt R T. 2009. Structure-based stabilization of HIV-1 gp120 enhances humoral immune responses to the induced co-receptor binding site. PLoS Pathog 5:e1000445.
79. Coutu M, Finzi A. 2015. HIV-1 gp120 dimers decrease the overall affinity of gp120 preparations for CD4-induced ligands. Journal of virological methods 215-216: 37-44.
80. Richard J, Veillette M, Batraville L A, Coutu M, Chapleau J P, Bonsignori M, Bernard N, Tremblay C, Roger M, Kaufmann D E, Finzi A. 2014. Flow cytometry-based assay to study HIV-1 gp120 specific antibody-dependent cellular cytotoxicity responses. Journal of virological methods 208:107-114.
81. Fouts et al. 2015. Balance of cellular and humoral immunity determines the level of protection by HIV vaccines in rhesus macaque models of HIV infection. Proc Natl Acad Sci USA 112(9):E992-9.
82. Acharya et al. 2014. Structural definition of an antibody-dependent cellular cytotoxicity response implicated in reduced risk for HIV-1 infection. J Virol. 88(21):12895-906.
83. Gohain et al. 2015. Cocrystal Structures of Antibody N60-i3 and Antibody JR4 in Complex with gp120 Define More Cluster A Epitopes Involved in Effective Antibody-Dependent Effector Function against HIV-1. J Virol. 2015 89(17):8840-54.
84. Gomez-Roman et al. 2006. A simplified method for the rapid fluorometric assessment of antibody-dependent cell-mediated cytotoxicity. J Immunol Methods. 308(1-2):53-67
85. Ausubel et al, eds. 1994. Current Protocols in Molecular Biology, Vol. 1, John Wiley & Sons, Inc., New York.

What is claimed is:

1. A HIV-1 gp120 inner domain (ID) immunogen, where the ID immunogen comprises:
    (a) a mature human immunodeficiency virus 1 (HIV-1) gp120 polypeptide having features (i)-(iv):
        (i) deletion of amino acids 1-11 of the N-terminus,
        (ii) cysteine residues at amino acids positions 65 and 115,
        (iii) deletion of amino acids 258-472 of the outer domain region and replacement by a GlyGly dipeptide linker, and
        (iv) deletion of amino acids 119-205 of the V1V2 loop and replacement by a GlyGlyAla tripeptide linker, wherein the amino acid numbering corresponds to the amino acid sequence set forth in SEQ ID NO:1; or
    (b) a variant of (a) having an amino acid sequence set forth in SEQ ID NO:60 or SEQ ID NO:61 and having the property of inducing a humoral Fc-mediated effector response to C1/C2 or combined C1/C2 and V1/V2 regions of HIV-1 gp120.

2. A HIV-1 gp120 ID immunogen comprising an amino acid sequence set forth in any one of SEQ ID NOs:3-54.

3. The ID immunogen of claim 1, wherein the immunogen has a $C_{65}$-$C_{115}$ disulfide bond.

4. An immunogenic composition comprising one or more ID immunogens and a pharmaceutically-acceptable carrier or diluent, wherein the ID immunogens are selected from those set forth in claim 1.

5. The immunogenic composition of claim 4, wherein the composition comprises one specific ID immunogen.

6. The immunogenic composition of claim 4, wherein the composition comprises two or more different ID immunogens.

7. The immunogenic composition of claim 4, wherein the composition comprises one or more ID immunogens set forth in SEQ ID NOs:3-54.

8. A method of inducing an immune response to an ID immunogen in a subject, comprising administering to a subject an immunogenic amount of an immunogenic composition of claim 4, thereby inducing an immune response in the subject.

9. A method of inducing an immune response to an ID immunogen in a subject, comprising administering to a subject an immunogenic amount of an immunogenic composition of claim 7, thereby inducing an immune response in the subject.

10. The ID immunogen of claim 2, wherein the immunogen has a $C_{65}$-$C_{115}$ disulfide bond.

11. The ID immunogen of claim 2, wherein the ID immunogen is ID2 set forth in SEQ ID NO:57.

12. The ID immunogen of claim 3, wherein the ID immunogen is ID2 set forth in SEQ ID NO:57.

13. An immunogenic composition comprising one or more ID immunogens and a pharmaceutically-acceptable carrier or diluent, wherein the ID immunogens are selected from those set forth in claim 2.

14. The immunogenic composition of claim 13, wherein the composition comprises one or more ID immunogens set forth in SEQ ID NOs:3-54.

15. A method of inducing an immune response to an ID immunogen in a subject, comprising administering to a subject an immunogenic amount of an immunogenic composition of claim 14, thereby inducing an immune response in the subject.

* * * * *